United States Patent
Mao et al.

(10) Patent No.: US 10,802,021 B2
(45) Date of Patent: Oct. 13, 2020

(54) SYNTHETIC HYBRID RECEPTOR AND GENETIC CIRCUIT IN BACTERIA TO DETECT ENTERIC PATHOGENIC MICROORGANISMS

(71) Applicants: Massachusetts Institute of Technology, Cambridge, MA (US); Trustees of Boston University, Boston, MA (US)

(72) Inventors: Ning Mao, Cambridge, MA (US); Douglas Ewen Cameron, Brookline, MA (US); James Collins, Newton, MA (US)

(73) Assignees: Massachusetts Institute of Technology, Cambridge, MA (US); Trustees of Boston University, Boston, MA (US)

( * ) Notice: Subject to any disclaimer, the term of this patent is extended or adjusted under 35 U.S.C. 154(b) by 310 days.

(21) Appl. No.: 15/580,845

(22) PCT Filed: Jun. 9, 2016

(86) PCT No.: PCT/US2016/036703
§ 371 (c)(1),
(2) Date: Dec. 8, 2017

(87) PCT Pub. No.: WO2016/201106
PCT Pub. Date: Dec. 15, 2016

(65) Prior Publication Data
US 2018/0328923 A1 Nov. 15, 2018
US 2020/0173993 A9 Jun. 4, 2020

Related U.S. Application Data

(60) Provisional application No. 62/172,971, filed on Jun. 9, 2015.

(51) Int. Cl.
*G01N 33/569* (2006.01)
*C07K 14/28* (2006.01)
*C07K 14/195* (2006.01)
*C12N 9/12* (2006.01)
*A61K 35/744* (2015.01)
*C12N 15/62* (2006.01)

(52) U.S. Cl.
CPC ...... *G01N 33/56911* (2013.01); *A61K 35/744* (2013.01); *C07K 14/195* (2013.01); *C07K 14/28* (2013.01); *C12N 9/12* (2013.01); *C12N 15/62* (2013.01); *C12N 15/625* (2013.01); *C12Y 305/02006* (2013.01); *G01N 2333/28* (2013.01); *G01N 2800/26* (2013.01); *Y02A 50/52* (2018.01)

(58) Field of Classification Search
None
See application file for complete search history.

(56) References Cited

U.S. PATENT DOCUMENTS

2012/0027786 A1* 2/2012 Gupta .................. C07K 14/21
424/184.1

OTHER PUBLICATIONS

Higgins et al., The major Vibrio cholerae autoinducer and its role in virulence factor production. Nature. Dec. 6, 2007;450(7171):883-6. Epub Nov. 14, 2007.
Ke et al., CqsA-CqsS quorum-sensing signal-receptor specificity in Photobacterium angustum. Mol Microbiol. Feb. 2014;91(4):821-33. doi: 10.1111/mmi.12502. Epub Jan. 14, 2014.
Mascher et al., Stimulus Perception in Bacterial Signal-Transducing Histidine Kinases. Microbiol Mol Biol Rev. Dec. 2006; 70(4): 910-938. doi: 10.1128/MMBR.00020-06.
Mierau et al., 10 Years of the nisin-controlled gene expression system (NICE) in Lactococcus lactis. App Microbiol Biotechnol. Nov. 2005;68(6):705-17. doi: 10.1007/s00253-005-0107-6.
Ng et al., Signal production and detection specificity in Vibrio CqsA/CqsS quorum-sensing systems. Mol Microbiol. Mar. 2011;79(6):1407-17. doi: 10.1111/j.1365-2958.2011.07548.x. Epub Jan. 26, 2011.
Stock et al., Two-component signal transduction. Annu Rev Biochem. 2000;69:183-215.

* cited by examiner

*Primary Examiner* — Brian Gangle
(74) *Attorney, Agent, or Firm* — Wolf, Greenfield & Sacks, P.C.

(57) ABSTRACT

Provided herein are microorganisms engineered with hybrid receptors and genetic circuits. Also provided are hybrid receptors having a CqsS polypeptide and a heterologous histidine kinase domain of a two-component system. Methods for using engineered microorganisms to sense and destroy pathogens (e.g., *Vibrio cholerae*) are also provided.

20 Claims, 10 Drawing Sheets

Specification includes a Sequence Listing.

FIG. 3A BASIC CIRCUIT
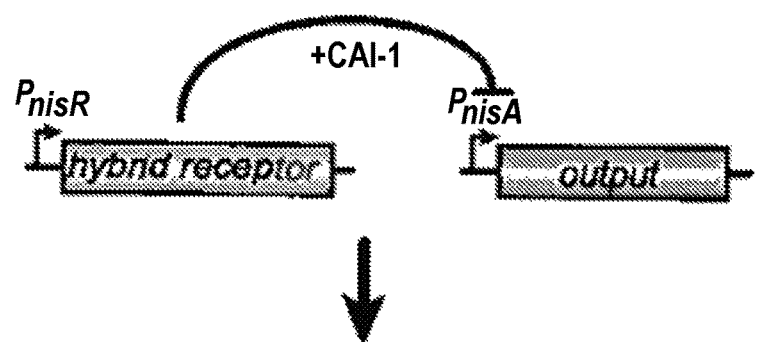
FIG. 3B SIGNAL INVERTER
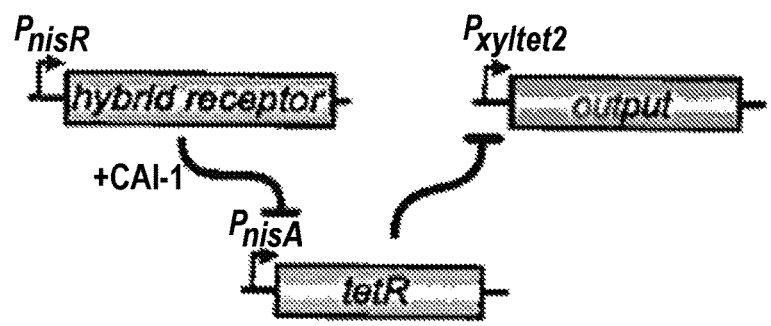

SEQUENCE LISTING

```
<160> NUMBER OF SEQ ID NOS: 51

<210> SEQ ID NO 1
<211> LENGTH: 403
<212> TYPE: PRT
<213> ORGANISM: Artificial Sequence
<220> FEATURE:
<223> OTHER INFORMATION: Synthetic Polypeptide

<400> SEQUENCE: 1

Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
```

```
                    100                 105                 110
Phe Leu His Ile Leu Leu Val His Asp Thr Arg Val Met Ala Leu Gln
            115                 120                 125
Ala Leu Phe Ser Val Leu Val Ala Tyr Leu Ala Val Tyr Gly Leu Thr
            130                 135                 140
Asp Phe His Pro Thr Thr Leu Ile Glu Trp Gln Tyr Ile Pro Ile Phe
145                 150                 155                 160
Leu Phe Thr Tyr Val Phe Gly Asn Leu Cys Phe Phe Arg Asn Gln Ile
                165                 170                 175
Ser Ala Glu Arg His Gly Lys His Asp Leu Ser Phe Gln Val Ala Ala
            180                 185                 190
Leu Ser His Asp Val Lys Thr Pro Leu Thr Val Leu Lys Gly Asn Ile
            195                 200                 205
Glu Leu Leu Glu Met Thr Glu Val Asn Glu Gln Gln Ala Asp Phe Ile
            210                 215                 220
Glu Ser Met Lys Asn Ser Leu Thr Val Phe Asp Lys Tyr Phe Asn Thr
225                 230                 235                 240
Met Ile Ser Tyr Thr Lys Leu Leu Asn Asp Glu Asn Asp Tyr Lys Ala
                245                 250                 255
Ile Ile Ser Leu Glu Asp Phe Leu Ile Asp Leu Ser Val Glu Leu Glu
            260                 265                 270
Glu Leu Ser Thr Thr Tyr Gln Val Asp Tyr Gln Leu Val Lys Lys Thr
            275                 280                 285
Asp Leu Thr Thr Phe Tyr Gly Asn Thr Leu Ala Leu Ser Arg Ala Leu
            290                 295                 300
Ile Asn Ile Phe Val Asn Ala Cys Gln Tyr Ala Lys Glu Gly Glu Lys
305                 310                 315                 320
Ile Val Ser Leu Ser Ile Tyr Asp Asp Glu Lys Tyr Leu Tyr Phe Glu
                325                 330                 335
Ile Trp Asn Asn Gly His Pro Phe Ser Glu Gln Ala Lys Lys Asn Ala
            340                 345                 350
Gly Lys Leu Phe Phe Thr Glu Asp Thr Gly Arg Ser Gly Lys His Tyr
            355                 360                 365
Gly Ile Gly Leu Ser Phe Ala Gln Gly Val Ala Leu Lys His Gln Gly
            370                 375                 380
Asn Leu Ile Leu Ser Asn Pro Gln Lys Gly Gly Ala Glu Val Ile Leu
385                 390                 395                 400
Lys Ile Lys

<210> SEQ ID NO 2
<211> LENGTH: 177
<212> TYPE: PRT
<213> ORGANISM: Artificial Sequence
<220> FEATURE:
<223> OTHER INFORMATION: Synthetic Polypeptide

<400> SEQUENCE: 2

Met Ile Val Ser Met Asp Val Ile Lys Arg Val Tyr Gln Tyr Ala Glu
1               5                   10                  15
Pro Asn Leu Ser Leu Val Gly Trp Met Gly Met Leu Gly Phe Pro Ala
            20                  25                  30
Tyr Tyr Phe Ile Trp Glu Tyr Trp Phe Pro Gln Ser Tyr Glu Asn Leu
            35                  40                  45
Gly Leu Arg Cys Ala Ala Ala Val Leu Phe Gly Gly Leu Val Phe Arg
        50                  55                  60
```

```
Asp Ser Met Pro Lys Lys Trp Gln Arg Tyr Met Pro Gly Tyr Phe Leu
 65                  70                  75                  80

Phe Thr Ile Gly Phe Cys Leu Pro Phe Phe Ala Phe Met Met Leu
             85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
            115                 120                 125

Ala Leu Phe Ser Val Leu Val Ala Tyr Leu Ala Val Tyr Gly Leu Thr
            130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Ser

<210> SEQ ID NO 3
<211> LENGTH: 227
<212> TYPE: PRT
<213> ORGANISM: Artificial Sequence
<220> FEATURE:
<223> OTHER INFORMATION: Synthetic Polypeptide

<400> SEQUENCE: 3

Ala Glu Arg His Gly Lys His Asp Leu Ser Phe Gln Val Ala Ala Leu
  1               5                  10                  15

Ser His Asp Val Lys Thr Pro Leu Thr Val Leu Lys Gly Asn Ile Glu
                 20                  25                  30

Leu Leu Glu Met Thr Glu Val Asn Glu Gln Gln Ala Asp Phe Ile Glu
             35                  40                  45

Ser Met Lys Asn Ser Leu Thr Val Phe Asp Lys Tyr Phe Asn Thr Met
         50                  55                  60

Ile Ser Tyr Thr Lys Leu Leu Asn Asp Glu Asn Asp Tyr Lys Ala Ile
 65                  70                  75                  80

Ile Ser Leu Glu Asp Phe Leu Ile Asp Leu Ser Val Glu Leu Glu Glu
                 85                  90                  95

Leu Ser Thr Thr Tyr Gln Val Asp Tyr Gln Leu Val Lys Lys Thr Asp
            100                 105                 110

Leu Thr Thr Phe Tyr Gly Asn Thr Leu Ala Leu Ser Arg Ala Leu Ile
            115                 120                 125

Asn Ile Phe Val Asn Ala Cys Gln Tyr Ala Lys Glu Gly Glu Lys Ile
            130                 135                 140

Val Ser Leu Ser Ile Tyr Asp Asp Glu Lys Tyr Leu Tyr Phe Glu Ile
145                 150                 155                 160

Trp Asn Asn Gly His Pro Phe Ser Glu Gln Ala Lys Lys Asn Ala Gly
                165                 170                 175

Lys Leu Phe Phe Thr Glu Asp Thr Gly Arg Ser Gly Lys His Tyr Gly
            180                 185                 190

Ile Gly Leu Ser Phe Ala Gln Gly Val Ala Leu Lys His Gln Gly Asn
            195                 200                 205

Leu Ile Leu Ser Asn Pro Gln Lys Gly Gly Ala Glu Val Ile Leu Lys
            210                 215                 220

Ile Lys Lys
225
```

```
<210> SEQ ID NO 4
<211> LENGTH: 686
<212> TYPE: PRT
<213> ORGANISM: Vibrio cholerae

<400> SEQUENCE: 4

Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
        115                 120                 125

Ala Leu Phe Ser Val Leu Val Ala Tyr Leu Ala Val Tyr Gly Leu Thr
    130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Ser His Glu Thr Lys Val Ser Ile Ala Lys Thr Phe Gly Ala Gly Ile
            180                 185                 190

Ala His Glu Met Arg Asn Pro Leu Ser Ala Leu Lys Thr Ser Ile Asp
        195                 200                 205

Val Val Arg Thr Met Ile Pro Lys Pro Gln Thr Ala Ala His Thr Asp
    210                 215                 220

Tyr Ser Leu Asp Ala Gln Glu Leu Asp Leu Leu His Gln Ile Leu Asn
225                 230                 235                 240

Glu Ala Asp Asp Val Ile Tyr Ser Gly Asn Asn Ala Ile Asp Leu Leu
                245                 250                 255

Leu Thr Ser Ile Asp Glu Asn Arg Val Ser Pro Ala Ser Phe Lys Lys
            260                 265                 270

His Ser Val Val Asp Val Ile Glu Lys Ala Val Lys Thr Phe Pro Tyr
        275                 280                 285

Lys Asn Ala Ala Asp Gln Ser Val Glu Leu Glu Val His Gln Pro
    290                 295                 300

Phe Asp Phe Phe Gly Ser Asp Thr Leu Leu Thr Tyr Ala Leu Phe Asn
305                 310                 315                 320

Leu Leu Lys Asn Ala Phe Tyr Tyr Gln Lys Glu His Phe Ser Val Arg
                325                 330                 335

Ile Ser Ile Glu Gln Thr Ile Glu Tyr Asn Leu Ile Arg Val Arg Asp
            340                 345                 350

Asn Gly Val Gly Ile Ala Pro Glu Met Leu Glu Asp Ile Phe Arg Asp
        355                 360                 365

Phe Tyr Thr Phe Gly Lys Asn Gly Ser Tyr Gly Leu Gly Leu Pro Phe
    370                 375                 380
```

```
Cys Arg Lys Val Met Thr Ala Phe Gly Gly Thr Ile Arg Cys Ala Ser
385                 390                 395                 400

Gln Gln Gly Gln Trp Thr Glu Phe Val Leu Ser Phe Pro Arg Tyr Asp
            405                 410                 415

Ser Asp Thr Val Asn Glu Ile Lys Thr Glu Leu Leu Lys Thr Lys Ser
        420                 425                 430

Leu Ile Tyr Ile Gly Ser Asn Gln Ala Ile Val Arg Glu Leu Asn Gln
    435                 440                 445

Leu Ala Val Glu Asp Glu Phe Gly Phe Thr Ala Ile Ser Ala Gln Gln
450                 455                 460

Ala Val Arg Arg Gln Asp Tyr Glu Phe Glu Phe Asp Leu Ile Leu Leu
465                 470                 475                 480

Asp Leu Asp Asp Ala Thr Ala Gln Gly Glu Leu Leu Pro Lys Leu Glu
            485                 490                 495

Gly Thr Leu Ser Phe Ala Glu Gly Cys Ile Gly Tyr Val Tyr Asp Pro
                500                 505                 510

Gly Lys Thr Tyr Ala Val Asn Ile Asn Arg Tyr Leu Arg Ile Gln Pro
            515                 520                 525

Ile Ser Ile His Ser Ile Leu Arg Lys Pro Arg Lys Ile Ile Glu Arg
    530                 535                 540

Leu Leu Phe Glu Gln Glu Ser Leu Ser Met Asn Arg Asn Val Ile Pro
545                 550                 555                 560

Leu Gln Lys Ser Arg His Glu Arg Arg Ile Leu Val Val Asp Asp Asn
            565                 570                 575

Gln Ser Ile Arg Thr Phe Thr Ala Ile Leu Leu Glu Gln Gln Gly Tyr
                580                 585                 590

Glu Val Val Gln Ala Asn Asp Gly Ser Glu Val Leu Lys His Met Glu
            595                 600                 605

Ser Gln Asn Ile Asp Leu Val Leu Met Asp Ile Glu Met Pro Asn Val
610                 615                 620

Gly Gly Leu Glu Ala Thr Arg Leu Ile Arg Asp Ser Glu His Glu Tyr
625                 630                 635                 640

Lys Asn Ile Pro Ile Ile Gly Tyr Thr Gly Asp Asn Ser Pro Lys Thr
                645                 650                 655

Leu Ala Leu Val Gln Thr Ser Gly Met Asn Asp Phe Ile Val Lys Pro
            660                 665                 670

Ala Asp Arg Asp Val Leu Leu Asn Lys Val Ala Ala Trp Val
675                 680                 685

<210> SEQ ID NO 5
<211> LENGTH: 447
<212> TYPE: PRT
<213> ORGANISM: Lactococcus lactis

<400> SEQUENCE: 5

Met Gly Lys Lys Tyr Ser Met Arg Arg Ile Trp Gln Ala Val Ile
1               5                   10                  15

Glu Ile Ile Ile Gly Thr Cys Leu Leu Ile Leu Leu Leu Gly Leu
                20                  25                  30

Thr Phe Phe Leu Arg Gln Ile Gly Gln Ile Ser Gly Ser Glu Thr Ile
            35                  40                  45

Arg Leu Ser Leu Asp Ser Asp Asn Leu Thr Ile Ser Asp Ile Glu Arg
    50                  55                  60

Asp Met Lys His Tyr Pro Tyr Asp Tyr Ile Ile Phe Asp Asn Asp Thr
```

65                  70                  75                  80
        Ser Lys Ile Leu Gly Gly His Tyr Val Lys Ser Asp Val Pro Ser Phe
                        85                  90                  95

Val Ala Ser Lys Gln Ser Ser His Asn Ile Thr Glu Gly Glu Ile Thr
                        100                 105                 110

Tyr Thr Tyr Ser Ser Asn Lys His Phe Ser Val Val Leu Arg Gln Asn
                        115                 120                 125

Ser Met Pro Glu Phe Thr Asn His Thr Leu Arg Ser Ile Ser Tyr Asn
                        130                 135                 140

Gln Phe Thr Tyr Leu Phe Phe Phe Leu Gly Glu Ile Ile Leu Ile Ile
        145                 150                 155                 160

Phe Ser Val Tyr His Leu Ile Arg Glu Phe Ser Lys Asn Phe Gln Ala
                        165                 170                 175

Val Gln Lys Ile Ala Leu Lys Met Gly Glu Ile Thr Thr Phe Pro Glu
                        180                 185                 190

Gln Glu Glu Ser Lys Ile Ile Glu Phe Asp Gln Val Leu Asn Asn Leu
                        195                 200                 205

Tyr Ser Lys Ser Lys Glu Leu Ala Phe Leu Ile Glu Ala Glu Arg His
                        210                 215                 220

Glu Lys His Asp Leu Ser Phe Gln Val Ala Ala Leu Ser His Asp Val
        225                 230                 235                 240

Lys Thr Pro Leu Thr Val Leu Lys Gly Asn Ile Glu Leu Leu Glu Met
                        245                 250                 255

Thr Glu Val Asn Glu Gln Gln Ala Asp Phe Ile Glu Ser Met Lys Asn
                        260                 265                 270

Ser Leu Thr Val Phe Asp Lys Tyr Phe Asn Thr Met Ile Ser Tyr Thr
                        275                 280                 285

Lys Leu Leu Asn Asp Glu Asn Asp Tyr Lys Ala Thr Ile Ser Leu Glu
                        290                 295                 300

Asp Phe Leu Ile Asp Leu Ser Val Glu Leu Glu Glu Leu Ser Thr Thr
        305                 310                 315                 320

Tyr Gln Val Asp Tyr Gln Leu Val Lys Lys Thr Asp Leu Thr Thr Phe
                        325                 330                 335

Tyr Gly Asn Thr Leu Ala Leu Ser Arg Ala Leu Ile Asn Ile Phe Val
                        340                 345                 350

Asn Ala Cys Gln Tyr Ala Lys Glu Gly Glu Lys Ile Val Ser Leu Ser
                        355                 360                 365

Ile Tyr Asp Asp Glu Lys Tyr Leu Tyr Phe Glu Ile Trp Asn Asn Gly
                        370                 375                 380

His Pro Phe Ser Glu Gln Ala Lys Lys Asn Ala Gly Lys Leu Phe Phe
        385                 390                 395                 400

Thr Glu Asp Thr Gly Arg Ser Gly Lys His Tyr Gly Ile Gly Leu Ser
                        405                 410                 415

Phe Ala Gln Gly Val Ala Leu Lys His Gln Gly Asn Leu Ile Leu Ser
                        420                 425                 430

Asn Pro Gln Lys Gly Gly Ala Glu Val Ile Leu Lys Ile Lys Lys
                        435                 440                 445

<210> SEQ ID NO 6
<211> LENGTH: 404
<212> TYPE: PRT
<213> ORGANISM: Artificial Sequence
<220> FEATURE:
<223> OTHER INFORMATION: Synthetic Polypeptide

<400> SEQUENCE: 6

```
Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
                100                 105                 110

Phe Leu His Ile Leu Leu Val His Asp Thr Arg Val Met Ala Leu Gln
            115                 120                 125

Ala Leu Phe Ser Val Leu Val Ala Tyr Leu Ala Val Tyr Gly Leu Thr
            130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Gly Ala Glu Arg His Gly Lys His Asp Leu Ser Phe Gln Val Ala Ala
            180                 185                 190

Leu Ser His Asp Val Lys Thr Pro Leu Thr Val Leu Lys Gly Asn Ile
        195                 200                 205

Glu Leu Leu Glu Met Thr Glu Val Asn Glu Gln Gln Ala Asp Phe Ile
210                 215                 220

Glu Ser Met Lys Asn Ser Leu Thr Val Phe Asp Lys Tyr Phe Asn Thr
225                 230                 235                 240

Met Ile Ser Tyr Thr Lys Leu Leu Asn Asp Glu Asn Asp Tyr Lys Ala
                245                 250                 255

Ile Ile Ser Leu Glu Asp Phe Leu Ile Asp Leu Ser Val Glu Leu Glu
            260                 265                 270

Glu Leu Ser Thr Thr Tyr Gln Val Asp Tyr Gln Leu Val Lys Lys Thr
        275                 280                 285

Asp Leu Thr Thr Phe Tyr Gly Asn Thr Leu Ala Leu Ser Arg Ala Leu
        290                 295                 300

Ile Asn Ile Phe Val Asn Ala Cys Gln Tyr Ala Lys Glu Gly Glu Lys
305                 310                 315                 320

Ile Val Ser Leu Ser Ile Tyr Asp Asp Glu Lys Tyr Leu Tyr Phe Glu
                325                 330                 335

Ile Trp Asn Asn Gly His Pro Phe Ser Glu Gln Ala Lys Lys Asn Ala
            340                 345                 350

Gly Lys Leu Phe Phe Thr Glu Asp Thr Gly Arg Ser Gly Lys His Tyr
        355                 360                 365

Gly Ile Gly Leu Ser Phe Ala Gln Gly Val Ala Leu Lys His Gln Gly
    370                 375                 380

Asn Leu Ile Leu Ser Asn Pro Gln Lys Gly Gly Ala Glu Val Ile Leu
385                 390                 395                 400

Lys Ile Lys Lys
```

<210> SEQ ID NO 7
<211> LENGTH: 404
<212> TYPE: PRT
<213> ORGANISM: Artificial Sequence
<220> FEATURE:
<223> OTHER INFORMATION: Synthetic Polypeptide

<400> SEQUENCE: 7

```
Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65              70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
        115                 120                 125

Ala Leu Phe Ser Val Leu Val Ala Tyr Leu Ala Val Tyr Gly Leu Thr
    130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Ala Ala Glu Arg His Gly Lys His Asp Leu Ser Phe Gln Val Ala Ala
            180                 185                 190

Leu Ser His Asp Val Lys Thr Pro Leu Thr Val Leu Lys Gly Asn Ile
        195                 200                 205

Glu Leu Leu Glu Met Thr Glu Val Asn Glu Gln Gln Ala Asp Phe Ile
    210                 215                 220

Glu Ser Met Lys Asn Ser Leu Thr Val Phe Asp Lys Tyr Phe Asn Thr
225                 230                 235                 240

Met Ile Ser Tyr Thr Lys Leu Leu Asn Asp Glu Asn Asp Tyr Lys Ala
                245                 250                 255

Ile Ile Ser Leu Glu Asp Phe Leu Ile Asp Leu Ser Val Glu Leu Glu
            260                 265                 270

Glu Leu Ser Thr Thr Tyr Gln Val Asp Tyr Gln Leu Val Lys Lys Thr
        275                 280                 285

Asp Leu Thr Thr Phe Tyr Gly Asn Thr Leu Ala Leu Ser Arg Ala Leu
    290                 295                 300

Ile Asn Ile Phe Val Asn Ala Cys Gln Tyr Ala Lys Glu Gly Glu Lys
305                 310                 315                 320

Ile Val Ser Leu Ser Ile Tyr Asp Asp Glu Lys Tyr Leu Tyr Phe Glu
                325                 330                 335

Ile Trp Asn Asn Gly His Pro Phe Ser Glu Gln Ala Lys Lys Asn Ala
            340                 345                 350

Gly Lys Leu Phe Phe Thr Glu Asp Thr Gly Arg Ser Gly Lys His Tyr
        355                 360                 365
```

```
Gly Ile Gly Leu Ser Phe Ala Gln Gly Val Ala Leu Lys His Gln Gly
370                 375                 380

Asn Leu Ile Leu Ser Asn Pro Gln Lys Gly Gly Ala Glu Val Ile Leu
385                 390                 395                 400

Lys Ile Lys Lys

<210> SEQ ID NO 8
<211> LENGTH: 404
<212> TYPE: PRT
<213> ORGANISM: Artificial Sequence
<220> FEATURE:
<223> OTHER INFORMATION: Synthetic Polypeptide

<400> SEQUENCE: 8

Met Ile Val Ser Met Asp Val Ile Lys Arg Val Tyr Gln Tyr Ala Glu
1               5                   10                  15

Pro Asn Leu Ser Leu Val Gly Trp Gly Met Leu Gly Phe Pro Ala
            20                  25                  30

Tyr Tyr Phe Ile Trp Glu Tyr Trp Phe Pro Gln Ser Tyr Glu Asn Leu
                35                  40                  45

Gly Leu Arg Cys Ala Ala Val Leu Phe Gly Gly Leu Val Phe Arg
            50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
            115                 120                 125

Ala Leu Phe Ser Val Leu Val Ala Tyr Leu Ala Val Tyr Gly Leu Thr
130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Thr Ala Glu Arg His Gly Lys His Asp Leu Ser Phe Gln Val Ala Ala
            180                 185                 190

Leu Ser His Asp Val Lys Thr Pro Leu Thr Val Leu Lys Gly Asn Ile
            195                 200                 205

Glu Leu Leu Glu Met Thr Glu Val Asn Glu Gln Gln Ala Asp Phe Ile
210                 215                 220

Glu Ser Met Lys Asn Ser Leu Thr Val Phe Asp Lys Tyr Phe Asn Thr
225                 230                 235                 240

Met Ile Ser Tyr Thr Lys Leu Leu Asn Asp Glu Asn Asp Tyr Lys Ala
                245                 250                 255

Ile Ile Ser Leu Glu Asp Phe Leu Ile Asp Leu Ser Val Glu Leu Glu
            260                 265                 270

Glu Leu Ser Thr Thr Tyr Gln Val Asp Tyr Gln Leu Val Lys Lys Thr
            275                 280                 285

Asp Leu Thr Thr Phe Tyr Gly Asn Thr Leu Ala Leu Ser Arg Ala Leu
290                 295                 300

Ile Asn Ile Phe Val Asn Ala Cys Gln Tyr Ala Lys Glu Gly Glu Lys
305                 310                 315                 320

Ile Val Ser Leu Ser Ile Tyr Asp Asp Glu Lys Tyr Leu Tyr Phe Glu
```

```
                    325                 330                 335

Ile Trp Asn Asn Gly His Pro Phe Ser Glu Gln Ala Lys Lys Asn Ala
                340                 345                 350

Gly Lys Leu Phe Phe Thr Glu Asp Thr Gly Arg Ser Gly Lys His Tyr
            355                 360                 365

Gly Ile Gly Leu Ser Phe Ala Gln Gly Val Ala Leu Lys His Gln Gly
        370                 375                 380

Asn Leu Ile Leu Ser Asn Pro Gln Lys Gly Gly Ala Glu Val Ile Leu
385                 390                 395                 400

Lys Ile Lys Lys

<210> SEQ ID NO 9
<211> LENGTH: 404
<212> TYPE: PRT
<213> ORGANISM: Artificial Sequence
<220> FEATURE:
<223> OTHER INFORMATION: Synthetic Polypeptide

<400> SEQUENCE: 9

Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
        115                 120                 125

Ala Leu Phe Ser Val Leu Val Ala Tyr Leu Ala Val Tyr Gly Leu Thr
    130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Lys Ala Glu Arg His Gly Lys His Asp Leu Ser Phe Gln Val Ala Ala
            180                 185                 190

Leu Ser His Asp Val Lys Thr Pro Leu Thr Val Leu Lys Gly Asn Ile
        195                 200                 205

Glu Leu Leu Glu Met Thr Glu Val Asn Glu Gln Ala Asp Phe Ile
    210                 215                 220

Glu Ser Met Lys Asn Ser Leu Thr Val Phe Asp Lys Tyr Phe Asn Thr
225                 230                 235                 240

Met Ile Ser Tyr Thr Lys Leu Leu Asn Asp Glu Asn Asp Tyr Lys Ala
                245                 250                 255

Ile Ile Ser Leu Glu Asp Phe Leu Ile Asp Leu Ser Val Glu Leu Glu
            260                 265                 270

Glu Leu Ser Thr Thr Tyr Gln Val Asp Tyr Gln Leu Val Lys Lys Thr
        275                 280                 285
```

```
Asp Leu Thr Thr Phe Tyr Gly Asn Thr Leu Ala Leu Ser Arg Ala Leu
        290                 295                 300

Ile Asn Ile Phe Val Asn Ala Cys Gln Tyr Ala Lys Glu Gly Glu Lys
305                 310                 315                 320

Ile Val Ser Leu Ser Ile Tyr Asp Asp Glu Lys Tyr Leu Tyr Phe Glu
                325                 330                 335

Ile Trp Asn Asn Gly His Pro Phe Ser Glu Gln Ala Lys Lys Asn Ala
            340                 345                 350

Gly Lys Leu Phe Phe Thr Glu Asp Thr Gly Arg Ser Gly Lys His Tyr
        355                 360                 365

Gly Ile Gly Leu Ser Phe Ala Gln Gly Val Ala Leu Lys His Gln Gly
    370                 375                 380

Asn Leu Ile Leu Ser Asn Pro Gln Lys Gly Gly Ala Glu Val Ile Leu
385                 390                 395                 400

Lys Ile Lys Lys

<210> SEQ ID NO 10
<211> LENGTH: 404
<212> TYPE: PRT
<213> ORGANISM: Artificial Sequence
<220> FEATURE:
<223> OTHER INFORMATION: Synthetic Polypeptide

<400> SEQUENCE: 10

Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
        115                 120                 125

Ala Leu Phe Ser Val Leu Val Ala Tyr Leu Ala Val Tyr Gly Leu Thr
    130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Ser Gly Glu Arg His Gly Lys His Asp Leu Ser Phe Gln Val Ala Ala
            180                 185                 190

Leu Ser His Asp Val Lys Thr Pro Leu Thr Val Leu Lys Gly Asn Ile
        195                 200                 205

Glu Leu Leu Glu Met Thr Glu Val Asn Glu Gln Gln Ala Asp Phe Ile
    210                 215                 220

Glu Ser Met Lys Asn Ser Leu Thr Val Phe Asp Lys Tyr Phe Asn Thr
225                 230                 235                 240
```

Met Ile Ser Tyr Thr Lys Leu Leu Asn Asp Glu Asn Asp Tyr Lys Ala
            245                 250                 255

Ile Ile Ser Leu Glu Asp Phe Leu Ile Asp Leu Ser Val Glu Leu Glu
        260                 265                 270

Glu Leu Ser Thr Thr Tyr Gln Val Asp Tyr Gln Leu Val Lys Lys Thr
        275                 280                 285

Asp Leu Thr Thr Phe Tyr Gly Asn Thr Leu Ala Leu Ser Arg Ala Leu
290                 295                 300

Ile Asn Ile Phe Val Asn Ala Cys Gln Tyr Ala Lys Glu Gly Glu Lys
305                 310                 315                 320

Ile Val Ser Leu Ser Ile Tyr Asp Asp Glu Lys Tyr Leu Tyr Phe Glu
                325                 330                 335

Ile Trp Asn Asn Gly His Pro Phe Ser Glu Gln Ala Lys Lys Asn Ala
            340                 345                 350

Gly Lys Leu Phe Phe Thr Glu Asp Thr Gly Arg Ser Gly Lys His Tyr
        355                 360                 365

Gly Ile Gly Leu Ser Phe Ala Gln Gly Val Ala Leu Lys His Gln Gly
    370                 375                 380

Asn Leu Ile Leu Ser Asn Pro Gln Lys Gly Gly Ala Glu Val Ile Leu
385                 390                 395                 400

Lys Ile Lys Lys

<210> SEQ ID NO 11
<211> LENGTH: 404
<212> TYPE: PRT
<213> ORGANISM: Artificial Sequence
<220> FEATURE:
<223> OTHER INFORMATION: Synthetic Polypeptide

<400> SEQUENCE: 11

Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
        115                 120                 125

Ala Leu Phe Ser Val Leu Val Ala Tyr Leu Ala Val Tyr Gly Leu Thr
    130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Ser Asp Glu Arg His Gly Lys His Asp Leu Ser Phe Gln Val Ala Ala
            180                 185                 190

Leu Ser His Asp Val Lys Thr Pro Leu Thr Val Leu Lys Gly Asn Ile

```
                 195                 200                 205
Glu Leu Leu Glu Met Thr Glu Val Asn Glu Gln Gln Ala Asp Phe Ile
210                 215                 220

Glu Ser Met Lys Asn Ser Leu Thr Val Phe Asp Lys Tyr Phe Asn Thr
225                 230                 235                 240

Met Ile Ser Tyr Thr Lys Leu Leu Asn Asp Glu Asn Asp Tyr Lys Ala
                245                 250                 255

Ile Ile Ser Leu Glu Asp Phe Leu Ile Asp Leu Ser Val Glu Leu Glu
            260                 265                 270

Glu Leu Ser Thr Thr Tyr Gln Val Asp Tyr Gln Leu Val Lys Lys Thr
        275                 280                 285

Asp Leu Thr Thr Phe Tyr Gly Asn Thr Leu Ala Leu Ser Arg Ala Leu
    290                 295                 300

Ile Asn Ile Phe Val Asn Ala Cys Gln Tyr Ala Lys Glu Gly Glu Lys
305                 310                 315                 320

Ile Val Ser Leu Ser Ile Tyr Asp Asp Glu Lys Tyr Leu Tyr Phe Glu
                325                 330                 335

Ile Trp Asn Asn Gly His Pro Phe Ser Glu Gln Ala Lys Lys Asn Ala
            340                 345                 350

Gly Lys Leu Phe Phe Thr Glu Asp Thr Gly Arg Ser Gly Lys His Tyr
        355                 360                 365

Gly Ile Gly Leu Ser Phe Ala Gln Gly Val Ala Leu Lys His Gln Gly
    370                 375                 380

Asn Leu Ile Leu Ser Asn Pro Gln Lys Gly Gly Ala Glu Val Ile Leu
385                 390                 395                 400

Lys Ile Lys Lys

<210> SEQ ID NO 12
<211> LENGTH: 404
<212> TYPE: PRT
<213> ORGANISM: Artificial Sequence
<220> FEATURE:
<223> OTHER INFORMATION: Synthetic Polypeptide

<400> SEQUENCE: 12

Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
                20                  25                  30

Tyr Tyr Phe Ile Trp Glu Tyr Trp Phe Pro Gln Ser Tyr Glu Asn Leu
            35                  40                  45

Gly Leu Arg Cys Ala Ala Ala Val Leu Phe Gly Gly Leu Val Phe Arg
        50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
                100                 105                 110

Phe Leu His Ile Leu Leu Val His Asp Thr Arg Val Met Ala Leu Gln
            115                 120                 125

Ala Leu Phe Ser Val Leu Val Ala Tyr Leu Ala Val Tyr Gly Leu Thr
        130                 135                 140

Asp Phe His Pro Thr Thr Leu Ile Glu Trp Gln Tyr Ile Pro Ile Phe
145                 150                 155                 160
```

```
Leu Phe Thr Tyr Val Phe Gly Asn Leu Cys Phe Phe Arg Asn Gln Ile
                165                 170                 175

Ser Lys Glu Arg His Gly Lys His Asp Leu Ser Phe Gln Val Ala Ala
            180                 185                 190

Leu Ser His Asp Val Lys Thr Pro Leu Thr Val Leu Lys Gly Asn Ile
        195                 200                 205

Glu Leu Leu Glu Met Thr Glu Val Asn Glu Gln Gln Ala Asp Phe Ile
    210                 215                 220

Glu Ser Met Lys Asn Ser Leu Thr Val Phe Asp Lys Tyr Phe Asn Thr
225                 230                 235                 240

Met Ile Ser Tyr Thr Lys Leu Leu Asn Asp Glu Asn Asp Tyr Lys Ala
                245                 250                 255

Ile Ile Ser Leu Glu Asp Phe Leu Ile Asp Leu Ser Val Glu Leu Glu
            260                 265                 270

Glu Leu Ser Thr Thr Tyr Gln Val Asp Tyr Gln Leu Val Lys Lys Thr
        275                 280                 285

Asp Leu Thr Thr Phe Tyr Gly Asn Thr Leu Ala Leu Ser Arg Ala Leu
    290                 295                 300

Ile Asn Ile Phe Val Asn Ala Cys Gln Tyr Ala Lys Glu Gly Glu Lys
305                 310                 315                 320

Ile Val Ser Leu Ser Ile Tyr Asp Asp Glu Lys Tyr Leu Tyr Phe Glu
                325                 330                 335

Ile Trp Asn Asn Gly His Pro Phe Ser Glu Gln Ala Lys Lys Asn Ala
            340                 345                 350

Gly Lys Leu Phe Phe Thr Glu Asp Thr Gly Arg Ser Gly Lys His Tyr
        355                 360                 365

Gly Ile Gly Leu Ser Phe Ala Gln Gly Val Ala Leu Lys His Gln Gly
    370                 375                 380

Asn Leu Ile Leu Ser Asn Pro Gln Lys Gly Gly Ala Glu Val Ile Leu
385                 390                 395                 400

Lys Ile Lys Lys

<210> SEQ ID NO 13
<211> LENGTH: 403
<212> TYPE: PRT
<213> ORGANISM: Artificial Sequence
<220> FEATURE:
<223> OTHER INFORMATION: Synthetic Polypeptide

<400> SEQUENCE: 13

Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Thr Ala Met Ser Phe Met Ala Ser Ile
            100                 105                 110
```

```
Phe Leu His Ile Leu Leu Val His Asp Thr Arg Val Met Ala Leu Gln
            115                 120                 125

Ala Leu Phe Ser Val Leu Val Ala Tyr Leu Ala Val Tyr Gly Leu Thr
        130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Ser Glu Arg His Gly Lys His Asp Leu Ser Phe Gln Val Ala Ala Leu
            180                 185                 190

Ser His Asp Val Lys Thr Pro Leu Thr Val Leu Lys Gly Asn Ile Glu
        195                 200                 205

Leu Leu Glu Met Thr Glu Val Asn Glu Gln Gln Ala Asp Phe Ile Glu
210                 215                 220

Ser Met Lys Asn Ser Leu Thr Val Phe Asp Lys Tyr Phe Asn Thr Met
225                 230                 235                 240

Ile Ser Tyr Thr Lys Leu Leu Asn Asp Glu Asn Asp Tyr Lys Ala Ile
                245                 250                 255

Ile Ser Leu Glu Asp Phe Leu Ile Asp Leu Ser Val Glu Leu Glu Glu
            260                 265                 270

Leu Ser Thr Thr Tyr Gln Val Asp Tyr Gln Leu Val Lys Lys Thr Asp
        275                 280                 285

Leu Thr Thr Phe Tyr Gly Asn Thr Leu Ala Leu Ser Arg Ala Leu Ile
290                 295                 300

Asn Ile Phe Val Asn Ala Cys Gln Tyr Ala Lys Glu Gly Glu Lys Ile
305                 310                 315                 320

Val Ser Leu Ser Ile Tyr Asp Asp Glu Lys Tyr Leu Tyr Phe Glu Ile
                325                 330                 335

Trp Asn Asn Gly His Pro Phe Ser Glu Gln Ala Lys Lys Asn Ala Gly
            340                 345                 350

Lys Leu Phe Phe Thr Glu Asp Thr Gly Arg Ser Gly Lys His Tyr Gly
        355                 360                 365

Ile Gly Leu Ser Phe Ala Gln Gly Val Ala Leu Lys His Gln Gly Asn
370                 375                 380

Leu Ile Leu Ser Asn Pro Gln Lys Gly Gly Ala Glu Val Ile Leu Lys
385                 390                 395                 400

Ile Lys Lys

<210> SEQ ID NO 14
<211> LENGTH: 459
<212> TYPE: PRT
<213> ORGANISM: Artificial Sequence
<220> FEATURE:
<223> OTHER INFORMATION: Synthetic Polypeptide

<400> SEQUENCE: 14

Met Gly Ile Gly Phe Lys Gly Arg Lys Thr Leu Leu Arg Glu Leu Val
1               5                   10                  15

Lys Tyr Met Val Thr Leu Cys Ile Ser Leu Val Val Leu Ala Leu Leu
            20                  25                  30

Tyr Ile Phe Ile Asn Thr Ile Ala Met Asn Thr Gly Phe Ser His Pro
        35                  40                  45

Ala Asn Tyr Asn Glu Arg Glu Ala Glu Lys Leu Ala Pro Lys Leu Glu
    50                  55                  60

Thr Ile Asp Lys Val Thr Ala Asp Met Ile Pro Asp Thr Met Ser Tyr
```

```
                65                  70                  75                  80
Ala Ile Leu Asn Lys Glu Thr Lys Gln Lys Thr Ala Gly Thr Ile Lys
                85                  90                  95

Glu Lys Asp Leu Gln Leu Val Lys Lys Ile Glu Lys Lys Pro Tyr
            100                 105                 110

Val Asn Tyr Lys Gln Lys Gly Tyr Leu Val Ile Glu Arg Asn Asn Glu
            115                 120                 125

Tyr Cys Val Leu Gln Tyr Ser Leu Arg Ala Asp Phe Ser Ser Pro Leu
            130                 135                 140

Leu Arg Lys Tyr Leu Pro Asn Tyr Glu Leu Thr Ser Ile Cys Ile Leu
145                 150                 155                 160

Ile Ile Leu Leu Ile Ile Val Ile Ser Ile Ile Thr Thr Tyr Phe Ala
                165                 170                 175

Asn Arg Leu Arg Lys His Phe Glu Thr Leu Asn Val Ile Thr Arg Tyr
            180                 185                 190

Ile Lys Glu Gln Asn Leu Gln Phe Thr Pro Glu Phe Thr His Ile Lys
            195                 200                 205

Glu Phe Asp Asp Val Ile Asp Ser Leu Ile Glu Met Arg Asp Ala Leu
            210                 215                 220

Gln Ser Ser Leu Glu Ala Gln Trp Arg Leu Glu Lys Asn Lys Lys Glu
225                 230                 235                 240

Gln Ile Gly Ala Leu Ala His Asp Ile Lys Ile Pro Ile Thr Ile Ile
                245                 250                 255

Lys Gly Asn Ala Glu Leu Leu Ser Leu Ser Met Gln Asn Glu Glu Gln
            260                 265                 270

Ala Glu Tyr Thr Lys Tyr Ile Leu Gly Ala Gly Asn Gln Ile Glu Gln
            275                 280                 285

Tyr Ile Tyr Gln Leu Ile His Leu Ser Lys Thr Glu Asp Ala Leu Thr
            290                 295                 300

Ile His Leu Glu Lys Ala Ser Val Asp Glu Leu Thr Glu Thr Leu Val
305                 310                 315                 320

Lys Asp Ile Ser Ala Tyr Lys Gly Asn Lys Asn Ile Asn Ile Ser Phe
                325                 330                 335

Lys Lys Glu Asn Leu Met Lys Glu Ala Lys Ile Asp Trp Gln Leu Leu
            340                 345                 350

His Arg Ala Leu Leu Asn Ile Leu Thr Asn Ala Val Asp Tyr Thr Pro
            355                 360                 365

Glu Gly Gly Thr Val Ser Val His Ala Glu Cys Asp Ser Glu Ile Phe
            370                 375                 380

Tyr Phe Phe Val Lys Asp Thr Gly Asn Gly Phe Ser Glu Met Gly Leu
385                 390                 395                 400

Lys Lys Ala Thr Glu Leu Phe Tyr Met Asp Asp Lys Ser Arg His Ser
                405                 410                 415

Lys Gly His Tyr Gly Met Gly Leu Thr Phe Ala Lys Asn Ala Val Asn
            420                 425                 430

Leu His Asn Gly Glu Leu Thr Leu Gly Asn Thr Ile Ala Gly Gly Ala
            435                 440                 445

Glu Val Arg Val Lys Ile Pro Leu Arg Asn Glu
            450                 455

<210> SEQ ID NO 15
<211> LENGTH: 227
<212> TYPE: PRT
<213> ORGANISM: Artificial Sequence
```

<220> FEATURE:
<223> OTHER INFORMATION: Synthetic Polypeptide

<400> SEQUENCE: 15

```
Ala Glu Arg His Glu Lys His Asp Leu Ser Phe Gln Val Ala Ala Leu
1               5                   10                  15

Ser His Asp Val Lys Thr Pro Leu Thr Val Leu Lys Gly Asn Ile Glu
            20                  25                  30

Leu Leu Glu Met Thr Glu Val Asn Glu Gln Gln Ala Asp Phe Ile Glu
        35                  40                  45

Ser Met Lys Asn Ser Leu Thr Val Phe Asp Lys Tyr Phe Asn Thr Met
50                  55                  60

Ile Ser Tyr Thr Lys Leu Leu Asn Asp Glu Asn Asp Tyr Lys Ala Thr
65                  70                  75                  80

Ile Ser Leu Glu Asp Phe Leu Ile Asp Leu Ser Val Glu Leu Glu Glu
                85                  90                  95

Leu Ser Thr Thr Tyr Gln Val Asp Tyr Gln Leu Val Lys Lys Thr Asp
            100                 105                 110

Leu Thr Thr Phe Tyr Gly Asn Thr Leu Ala Leu Ser Arg Ala Leu Ile
        115                 120                 125

Asn Ile Phe Val Asn Ala Cys Gln Tyr Ala Lys Glu Gly Glu Lys Ile
130                 135                 140

Val Ser Leu Ser Ile Tyr Asp Asp Glu Lys Tyr Leu Tyr Phe Glu Ile
145                 150                 155                 160

Trp Asn Asn Gly His Pro Phe Ser Glu Gln Ala Lys Lys Asn Ala Gly
                165                 170                 175

Lys Leu Phe Phe Thr Glu Asp Thr Gly Arg Ser Gly Lys His Tyr Gly
            180                 185                 190

Ile Gly Leu Ser Phe Ala Gln Gly Val Ala Leu Lys His Gln Gly Asn
        195                 200                 205

Leu Ile Leu Ser Asn Pro Gln Lys Gly Gly Ala Glu Val Ile Leu Lys
210                 215                 220

Ile Lys Lys
225
```

<210> SEQ ID NO 16
<211> LENGTH: 404
<212> TYPE: PRT
<213> ORGANISM: Artificial Sequence
<220> FEATURE:
<223> OTHER INFORMATION: Synthetic Polypeptide

<400> SEQUENCE: 16

```
Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Ala Val Leu Phe Gly Gly Leu Val Phe Arg
50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
```

```
            100                 105                 110
Phe Leu His Ile Leu Leu Val His Asp Thr Arg Val Met Ala Leu Gln
        115                 120                 125
Ala Leu Phe Ser Val Leu Val Ala Tyr Leu Ala Val Tyr Gly Leu Thr
        130                 135                 140
Asp Phe His Pro Thr Thr Leu Ile Glu Trp Gln Tyr Ile Pro Ile Phe
145                 150                 155                 160
Leu Phe Thr Tyr Val Phe Gly Asn Leu Cys Phe Phe Arg Phe Leu Ile
                165                 170                 175
Glu Ala Glu Arg His Glu Lys His Asp Leu Ser Phe Gln Val Ala Ala
            180                 185                 190
Leu Ser His Asp Val Lys Thr Pro Leu Thr Val Leu Lys Gly Asn Ile
        195                 200                 205
Glu Leu Leu Glu Met Thr Glu Val Asn Glu Gln Gln Ala Asp Phe Ile
        210                 215                 220
Glu Ser Met Lys Asn Ser Leu Thr Val Phe Asp Lys Tyr Phe Asn Thr
225                 230                 235                 240
Met Ile Ser Tyr Thr Lys Leu Leu Asn Asp Glu Asn Asp Tyr Lys Ala
                245                 250                 255
Thr Ile Ser Leu Glu Asp Phe Leu Ile Asp Leu Ser Val Glu Leu Glu
            260                 265                 270
Glu Leu Ser Thr Thr Tyr Gln Val Asp Tyr Gln Leu Val Lys Lys Thr
        275                 280                 285
Asp Leu Thr Thr Phe Tyr Gly Asn Thr Leu Ala Leu Ser Arg Ala Leu
        290                 295                 300
Ile Asn Ile Phe Val Asn Ala Cys Gln Tyr Ala Lys Glu Gly Glu Lys
305                 310                 315                 320
Ile Val Ser Leu Ser Ile Tyr Asp Asp Glu Lys Tyr Leu Tyr Phe Glu
                325                 330                 335
Ile Trp Asn Asn Gly His Pro Phe Ser Glu Gln Ala Lys Lys Asn Ala
            340                 345                 350
Gly Lys Leu Phe Phe Thr Glu Asp Thr Gly Arg Ser Gly Lys His Tyr
        355                 360                 365
Gly Ile Gly Leu Ser Phe Ala Gln Gly Val Ala Leu Lys His Gln Gly
        370                 375                 380
Asn Leu Ile Leu Ser Asn Pro Gln Lys Gly Gly Ala Glu Val Ile Leu
385                 390                 395                 400
Lys Ile Lys Lys

<210> SEQ ID NO 17
<211> LENGTH: 404
<212> TYPE: PRT
<213> ORGANISM: Artificial Sequence
<220> FEATURE:
<223> OTHER INFORMATION: Synthetic Polypeptide

<400> SEQUENCE: 17

Met Ile Val Ser Met Asp Val Ile Lys Arg Val Tyr Gln Tyr Ala Glu
1               5                   10                  15
Pro Asn Leu Ser Leu Val Gly Trp Met Gly Met Leu Gly Phe Pro Ala
            20                  25                  30
Tyr Tyr Phe Ile Trp Glu Tyr Trp Phe Pro Gln Ser Tyr Glu Asn Leu
        35                  40                  45
Gly Leu Arg Cys Ala Ala Ala Val Leu Phe Gly Gly Leu Val Phe Arg
    50                  55                  60
```

```
Asp Ser Met Pro Lys Lys Trp Gln Arg Tyr Met Pro Gly Tyr Phe Leu
 65                  70                  75                  80

Phe Thr Ile Gly Phe Cys Leu Pro Phe Phe Ala Phe Met Met Leu
                 85                  90                  95

Met Asn Asp Trp Ser Thr Ile Trp Ala Met Ser Phe Met Ala Ser Ile
                100                 105                 110

Phe Leu His Ile Leu Leu Val His Asp Thr Arg Val Met Ala Leu Gln
            115                 120                 125

Ala Leu Phe Ser Val Leu Val Ala Tyr Leu Ala Val Tyr Gly Leu Thr
            130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Leu Ile
                165                 170                 175

Glu Ala Glu Arg His Glu Lys His Asp Leu Ser Phe Gln Val Ala Ala
            180                 185                 190

Leu Ser His Asp Val Lys Thr Pro Leu Thr Val Leu Lys Gly Asn Ile
            195                 200                 205

Glu Leu Leu Glu Met Thr Glu Val Asn Glu Gln Gln Ala Asp Phe Ile
210                 215                 220

Glu Ser Met Lys Asn Ser Leu Thr Val Phe Asp Lys Tyr Phe Asn Thr
225                 230                 235                 240

Met Ile Ser Tyr Thr Lys Leu Leu Asn Asp Glu Asn Asp Tyr Lys Ala
                245                 250                 255

Thr Ile Ser Leu Glu Asp Phe Leu Ile Asp Leu Ser Val Glu Leu Glu
            260                 265                 270

Glu Leu Ser Thr Thr Tyr Gln Val Asp Tyr Gln Leu Val Lys Lys Thr
            275                 280                 285

Asp Leu Thr Thr Phe Tyr Gly Asn Thr Leu Ala Leu Ser Arg Ala Leu
290                 295                 300

Ile Asn Ile Phe Val Asn Ala Cys Gln Tyr Ala Lys Glu Gly Glu Lys
305                 310                 315                 320

Ile Val Ser Leu Ser Ile Tyr Asp Asp Glu Lys Tyr Leu Tyr Phe Glu
                325                 330                 335

Ile Trp Asn Asn Gly His Pro Phe Ser Glu Gln Ala Lys Lys Asn Ala
                340                 345                 350

Gly Lys Leu Phe Phe Thr Glu Asp Thr Gly Arg Ser Gly Lys His Tyr
            355                 360                 365

Gly Ile Gly Leu Ser Phe Ala Gln Gly Val Ala Leu Lys His Gln Gly
            370                 375                 380

Asn Leu Ile Leu Ser Asn Pro Gln Lys Gly Gly Ala Glu Val Ile Leu
385                 390                 395                 400

Lys Ile Lys Lys

<210> SEQ ID NO 18
<211> LENGTH: 404
<212> TYPE: PRT
<213> ORGANISM: Artificial Sequence
<220> FEATURE:
<223> OTHER INFORMATION: Synthetic Polypeptide

<400> SEQUENCE: 18

Met Ile Val Ser Met Asp Val Ile Lys Arg Val Tyr Gln Tyr Ala Glu
 1               5                  10                  15
```

```
Pro Asn Leu Ser Leu Val Gly Trp Met Gly Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Ala Val Leu Phe Gly Gly Leu Val Phe Arg
        50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
                100                 105                 110

Phe Leu His Ile Leu Leu Val His Asp Thr Arg Val Met Ala Leu Gln
            115                 120                 125

Ala Leu Phe Ser Val Leu Val Ala Tyr Leu Ala Val Tyr Gly Leu Thr
        130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Glu Ala Glu Arg His Glu Lys His Asp Leu Ser Phe Gln Val Ala Ala
                180                 185                 190

Leu Ser His Asp Val Lys Thr Pro Leu Thr Val Leu Lys Gly Asn Ile
        195                 200                 205

Glu Leu Leu Glu Met Thr Glu Val Asn Glu Gln Ala Asp Phe Ile
210                 215                 220

Glu Ser Met Lys Asn Ser Leu Thr Val Phe Asp Lys Tyr Phe Asn Thr
225                 230                 235                 240

Met Ile Ser Tyr Thr Lys Leu Leu Asn Asp Glu Asn Asp Tyr Lys Ala
                245                 250                 255

Thr Ile Ser Leu Glu Asp Phe Leu Ile Asp Leu Ser Val Glu Leu Glu
            260                 265                 270

Glu Leu Ser Thr Thr Tyr Gln Val Asp Tyr Gln Leu Val Lys Lys Thr
        275                 280                 285

Asp Leu Thr Thr Phe Tyr Gly Asn Thr Leu Ala Leu Ser Arg Ala Leu
290                 295                 300

Ile Asn Ile Phe Val Asn Ala Cys Gln Tyr Ala Lys Glu Gly Glu Lys
305                 310                 315                 320

Ile Val Ser Leu Ser Ile Tyr Asp Asp Glu Lys Tyr Leu Tyr Phe Glu
                325                 330                 335

Ile Trp Asn Asn Gly His Pro Phe Ser Glu Gln Ala Lys Lys Asn Ala
                340                 345                 350

Gly Lys Leu Phe Phe Thr Glu Asp Thr Gly Arg Ser Gly Lys His Tyr
        355                 360                 365

Gly Ile Gly Leu Ser Phe Ala Gln Gly Val Ala Leu Lys His Gln Gly
        370                 375                 380

Asn Leu Ile Leu Ser Asn Pro Gln Lys Gly Gly Ala Glu Val Ile Leu
385                 390                 395                 400

Lys Ile Lys Lys

<210> SEQ ID NO 19
<211> LENGTH: 404
<212> TYPE: PRT
<213> ORGANISM: Artificial Sequence
```

<220> FEATURE:
<223> OTHER INFORMATION: Synthetic Polypeptide

<400> SEQUENCE: 19

```
Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
        115                 120                 125

Ala Leu Phe Ser Val Leu Val Ala Tyr Leu Ala Val Tyr Gly Leu Thr
    130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Ser Ala Glu Arg His Glu Lys His Asp Leu Ser Phe Gln Val Ala Ala
            180                 185                 190

Leu Ser His Asp Val Lys Thr Pro Leu Thr Val Leu Lys Gly Asn Ile
        195                 200                 205

Glu Leu Leu Glu Met Thr Glu Val Asn Glu Gln Gln Ala Asp Phe Ile
    210                 215                 220

Glu Ser Met Lys Asn Ser Leu Thr Val Phe Asp Lys Tyr Phe Asn Thr
225                 230                 235                 240

Met Ile Ser Tyr Thr Lys Leu Leu Asn Asp Glu Asn Asp Tyr Lys Ala
                245                 250                 255

Thr Ile Ser Leu Glu Asp Phe Leu Ile Asp Leu Ser Val Glu Leu Glu
            260                 265                 270

Glu Leu Ser Thr Thr Tyr Gln Val Asp Tyr Gln Leu Val Lys Lys Thr
        275                 280                 285

Asp Leu Thr Thr Phe Tyr Gly Asn Thr Leu Ala Leu Ser Arg Ala Leu
290                 295                 300

Ile Asn Ile Phe Val Asn Ala Cys Gln Tyr Ala Lys Glu Gly Glu Lys
305                 310                 315                 320

Ile Val Ser Leu Ser Ile Tyr Asp Asp Glu Lys Tyr Leu Tyr Phe Glu
                325                 330                 335

Ile Trp Asn Asn Gly His Pro Phe Ser Glu Gln Ala Lys Lys Asn Ala
            340                 345                 350

Gly Lys Leu Phe Phe Thr Glu Asp Thr Gly Arg Ser Gly Lys His Tyr
        355                 360                 365

Gly Ile Gly Leu Ser Phe Ala Gln Gly Val Ala Leu Lys His Gln Gly
    370                 375                 380

Asn Leu Ile Leu Ser Asn Pro Gln Lys Gly Gly Ala Glu Val Ile Leu
385                 390                 395                 400
```

Lys Ile Lys Lys

<210> SEQ ID NO 20
<211> LENGTH: 456
<212> TYPE: PRT
<213> ORGANISM: Artificial Sequence
<220> FEATURE:
<223> OTHER INFORMATION: Synthetic Polypeptide

<400> SEQUENCE: 20

```
Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
        115                 120                 125

Ala Leu Phe Ser Val Leu Val Ala Tyr Leu Ala Val Tyr Gly Leu Thr
    130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Arg Glu Phe Ser Lys Asn Phe Gln Ala Val Gln Lys Ile Ala Leu Lys
            180                 185                 190

Met Gly Glu Ile Thr Thr Phe Pro Glu Gln Glu Ser Lys Ile Ile
        195                 200                 205

Glu Phe Asp Gln Val Leu Asn Asn Leu Tyr Ser Lys Ser Lys Glu Leu
    210                 215                 220

Ala Phe Leu Ile Glu Ala Glu Arg His Glu Lys His Asp Leu Ser Phe
225                 230                 235                 240

Gln Val Ala Ala Leu Ser His Asp Val Lys Thr Pro Leu Thr Val Leu
                245                 250                 255

Lys Gly Asn Ile Glu Leu Leu Glu Met Thr Glu Val Asn Glu Gln Gln
            260                 265                 270

Ala Asp Phe Ile Glu Ser Met Lys Asn Ser Leu Thr Val Phe Asp Lys
        275                 280                 285

Tyr Phe Asn Thr Met Ile Ser Tyr Thr Lys Leu Leu Asn Asp Glu Asn
    290                 295                 300

Asp Tyr Lys Ala Thr Ile Ser Leu Glu Asp Phe Leu Ile Asp Leu Ser
305                 310                 315                 320

Val Glu Leu Glu Glu Leu Ser Thr Thr Tyr Gln Val Asp Tyr Gln Leu
                325                 330                 335

Val Lys Lys Thr Asp Leu Thr Thr Phe Tyr Gly Asn Thr Leu Ala Leu
            340                 345                 350
```

Ser Arg Ala Leu Ile Asn Ile Phe Val Asn Ala Cys Gln Tyr Ala Lys
        355                 360                 365

Glu Gly Glu Lys Ile Val Ser Leu Ser Ile Tyr Asp Asp Lys Tyr
    370                 375                 380

Leu Tyr Phe Glu Ile Trp Asn Asn Gly His Pro Phe Ser Gln Ala
385                 390                 395                 400

Lys Lys Asn Ala Gly Lys Leu Phe Phe Thr Glu Asp Thr Gly Arg Ser
            405                 410                 415

Gly Lys His Tyr Gly Ile Gly Leu Ser Phe Ala Gln Gly Val Ala Leu
            420                 425                 430

Lys His Gln Gly Asn Leu Ile Leu Ser Asn Pro Gln Lys Gly Gly Ala
            435                 440                 445

Glu Val Ile Leu Lys Ile Lys Lys
    450                 455

<210> SEQ ID NO 21
<211> LENGTH: 456
<212> TYPE: PRT
<213> ORGANISM: Artificial Sequence
<220> FEATURE:
<223> OTHER INFORMATION: Synthetic Polypeptide

<400> SEQUENCE: 21

Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
                100                 105                 110

Phe Leu His Ile Leu Leu Val His Asp Thr Arg Val Met Ala Leu Gln
            115                 120                 125

Ala Leu Phe Ser Val Leu Val Ala Tyr Leu Ala Val Tyr Gly Leu Thr
    130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Arg Glu Phe Ser Lys Asn Phe Gln Ala Val Gln Lys Ile Ala Leu Lys
            180                 185                 190

Met Gly Glu Ile Thr Thr Phe Pro Glu Gln Glu Glu Ser Lys Ile Ile
        195                 200                 205

Glu Phe Asp Gln Val Leu Asn Asn Leu Tyr Ser Lys Ser Lys Glu Leu
    210                 215                 220

Ala Phe Leu Ile Glu Ala Glu Arg His Glu Lys His Asp Leu Ser Phe
225                 230                 235                 240

Gln Val Ala Ala Leu Ser His Asp Val Lys Thr Pro Leu Thr Val Leu
                245                 250                 255

Lys Gly Asn Ile Glu Leu Leu Glu Met Thr Glu Val Asn Glu Gln Gln
            260                 265                 270

Ala Asp Phe Ile Glu Ser Met Lys Asn Ser Leu Thr Val Phe Asp Lys
        275                 280                 285

Tyr Phe Asn Thr Met Ile Ser Tyr Thr Lys Leu Leu Asn Asp Glu Asn
    290                 295                 300

Asp Tyr Lys Ala Thr Ile Ser Leu Glu Asp Phe Leu Ile Asp Leu Ser
305                 310                 315                 320

Val Glu Leu Glu Leu Ser Thr Thr Tyr Gln Val Asp Tyr Gln Leu
                325                 330                 335

Val Lys Lys Thr Asp Leu Thr Thr Phe Tyr Gly Asn Thr Leu Ala Leu
            340                 345                 350

Ser Arg Ala Leu Ile Asn Ile Phe Val Asn Ala Cys Gln Tyr Ala Lys
        355                 360                 365

Glu Gly Glu Lys Ile Val Ser Leu Ser Ile Tyr Asp Asp Glu Lys Tyr
    370                 375                 380

Leu Tyr Phe Glu Ile Trp Asn Asn Gly His Pro Phe Ser Glu Gln Ala
385                 390                 395                 400

Lys Lys Asn Ala Gly Lys Leu Phe Phe Thr Glu Asp Thr Gly Arg Ser
                405                 410                 415

Gly Lys His Tyr Gly Ile Gly Leu Ser Phe Ala Gln Gly Val Ala Leu
            420                 425                 430

Lys His Gln Gly Asn Leu Ile Leu Ser Asn Pro Gln Lys Gly Gly Ala
        435                 440                 445

Glu Val Ile Leu Lys Ile Lys Lys
    450                 455

<210> SEQ ID NO 22
<211> LENGTH: 456
<212> TYPE: PRT
<213> ORGANISM: Artificial Sequence
<220> FEATURE:
<223> OTHER INFORMATION: Synthetic Polypeptide

<400> SEQUENCE: 22

Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
            85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
        115                 120                 125

Ala Leu Phe Ser Val Leu Val Ala Tyr Leu Ala Val Tyr Gly Leu Thr
    130                 135                 140

Asp Phe His Pro Thr Thr Leu Ile Glu Trp Gln Tyr Ile Pro Ile Phe
145                 150                 155                 160

```
Leu Phe Thr Tyr Val Phe Gly Asn Leu Cys Phe Phe Arg Asn Leu Ile
                165                 170                 175

Arg Glu Phe Ser Lys Asn Phe Gln Ala Val Gln Lys Ile Ala Leu Lys
            180                 185                 190

Met Gly Glu Ile Thr Thr Phe Pro Glu Gln Glu Ser Lys Ile Ile
        195                 200                 205

Glu Phe Asp Gln Val Leu Asn Asn Leu Tyr Ser Lys Ser Lys Glu Leu
    210                 215                 220

Ala Phe Leu Ile Glu Ala Glu Arg His Glu Lys His Asp Leu Ser Phe
225                 230                 235                 240

Gln Val Ala Ala Leu Ser His Asp Val Lys Thr Pro Leu Thr Val Leu
                245                 250                 255

Lys Gly Asn Ile Glu Leu Leu Glu Met Thr Glu Val Asn Glu Gln Gln
            260                 265                 270

Ala Asp Phe Ile Glu Ser Met Lys Asn Ser Leu Thr Val Phe Asp Lys
        275                 280                 285

Tyr Phe Asn Thr Met Ile Ser Tyr Thr Lys Leu Leu Asn Asp Glu Asn
    290                 295                 300

Asp Tyr Lys Ala Thr Ile Ser Leu Glu Asp Phe Leu Ile Asp Leu Ser
305                 310                 315                 320

Val Glu Leu Glu Glu Leu Ser Thr Thr Tyr Gln Val Asp Tyr Gln Leu
                325                 330                 335

Val Lys Lys Thr Asp Leu Thr Thr Phe Tyr Gly Asn Thr Leu Ala Leu
            340                 345                 350

Ser Arg Ala Leu Ile Asn Ile Phe Val Asn Ala Cys Gln Tyr Ala Lys
        355                 360                 365

Glu Gly Glu Lys Ile Val Ser Leu Ser Ile Tyr Asp Asp Glu Lys Tyr
    370                 375                 380

Leu Tyr Phe Glu Ile Trp Asn Asn Gly His Pro Phe Ser Glu Gln Ala
385                 390                 395                 400

Lys Lys Asn Ala Gly Lys Leu Phe Phe Thr Asp Thr Gly Arg Ser
                405                 410                 415

Gly Lys His Tyr Gly Ile Gly Leu Ser Phe Ala Gln Gly Val Ala Leu
            420                 425                 430

Lys His Gln Gly Asn Leu Ile Leu Ser Asn Pro Gln Lys Gly Gly Ala
        435                 440                 445

Glu Val Ile Leu Lys Ile Lys Lys
    450                 455
```

<210> SEQ ID NO 23
<211> LENGTH: 457
<212> TYPE: PRT
<213> ORGANISM: Artificial Sequence
<220> FEATURE:
<223> OTHER INFORMATION: Synthetic Polypeptide

<400> SEQUENCE: 23

```
Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
                20                  25                  30

Tyr Tyr Phe Ile Trp Glu Tyr Trp Phe Pro Gln Ser Tyr Glu Asn Leu
            35                  40                  45

Gly Leu Arg Cys Ala Ala Ala Val Leu Phe Gly Gly Leu Val Phe Arg
        50                  55                  60
```

```
Asp Ser Met Pro Lys Lys Trp Gln Arg Tyr Met Pro Gly Tyr Phe Leu
 65                  70                  75                  80

Phe Thr Ile Gly Phe Cys Leu Pro Phe Phe Ala Phe Met Met Leu
             85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
            115                 120                 125

Ala Leu Phe Ser Val Leu Val Ala Tyr Leu Ala Val Tyr Gly Leu Thr
        130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Leu
                165                 170                 175

Ile Arg Glu Phe Ser Lys Asn Phe Gln Ala Val Gln Lys Ile Ala Leu
            180                 185                 190

Lys Met Gly Glu Ile Thr Thr Phe Pro Glu Gln Glu Ser Lys Ile
        195                 200                 205

Ile Glu Phe Asp Gln Val Leu Asn Asn Leu Tyr Ser Lys Ser Lys Glu
    210                 215                 220

Leu Ala Phe Leu Ile Glu Ala Glu Arg His Glu Lys His Asp Leu Ser
225                 230                 235                 240

Phe Gln Val Ala Ala Leu Ser His Asp Val Lys Thr Pro Leu Thr Val
                245                 250                 255

Leu Lys Gly Asn Ile Glu Leu Leu Glu Met Thr Glu Val Asn Glu Gln
            260                 265                 270

Gln Ala Asp Phe Ile Glu Ser Met Lys Asn Ser Leu Thr Val Phe Asp
        275                 280                 285

Lys Tyr Phe Asn Thr Met Ile Ser Tyr Thr Lys Leu Leu Asn Asp Glu
        290                 295                 300

Asn Asp Tyr Lys Ala Thr Ile Ser Leu Glu Asp Phe Leu Ile Asp Leu
305                 310                 315                 320

Ser Val Glu Leu Glu Glu Leu Ser Thr Thr Tyr Gln Val Asp Tyr Gln
                325                 330                 335

Leu Val Lys Lys Thr Asp Leu Thr Thr Phe Tyr Gly Asn Thr Leu Ala
            340                 345                 350

Leu Ser Arg Ala Leu Ile Asn Ile Phe Val Asn Ala Cys Gln Tyr Ala
        355                 360                 365

Lys Glu Gly Glu Lys Ile Val Ser Leu Ser Ile Tyr Asp Asp Glu Lys
        370                 375                 380

Tyr Leu Tyr Phe Glu Ile Trp Asn Asn Gly His Pro Phe Ser Glu Gln
385                 390                 395                 400

Ala Lys Lys Asn Ala Gly Lys Leu Phe Phe Thr Glu Asp Thr Gly Arg
                405                 410                 415

Ser Gly Lys His Tyr Gly Ile Gly Leu Ser Phe Ala Gln Gly Val Ala
            420                 425                 430

Leu Lys His Gln Gly Asn Leu Ile Leu Ser Asn Pro Gln Lys Gly Gly
        435                 440                 445

Ala Glu Val Ile Leu Lys Ile Lys Lys
        450                 455

<210> SEQ ID NO 24
<211> LENGTH: 455
<212> TYPE: PRT
```

<213> ORGANISM: Artificial Sequence
<220> FEATURE:
<223> OTHER INFORMATION: Synthetic Polypeptide

<400> SEQUENCE: 24

```
Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
            20                  25                  30

Tyr Tyr Phe Ile Trp Glu Tyr Trp Phe Pro Gln Ser Tyr Glu Asn Leu
        35                  40                  45

Gly Leu Arg Cys Ala Ala Val Leu Phe Gly Gly Leu Val Phe Arg
    50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
            100                 105                 110

Phe Leu His Ile Leu Leu Val His Asp Thr Arg Val Met Ala Leu Gln
        115                 120                 125

Ala Leu Phe Ser Val Leu Val Ala Tyr Leu Ala Val Tyr Gly Leu Thr
    130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe His Leu Ile Arg
                165                 170                 175

Glu Phe Ser Lys Asn Phe Gln Ala Val Gln Lys Ile Ala Leu Lys Met
            180                 185                 190

Gly Glu Ile Thr Thr Phe Pro Glu Gln Glu Ser Lys Ile Ile Glu
        195                 200                 205

Phe Asp Gln Val Leu Asn Asn Leu Tyr Ser Lys Ser Lys Glu Leu Ala
    210                 215                 220

Phe Leu Ile Glu Ala Glu Arg His Glu Lys His Asp Leu Ser Phe Gln
225                 230                 235                 240

Val Ala Ala Leu Ser His Asp Val Lys Thr Pro Leu Thr Val Leu Lys
                245                 250                 255

Gly Asn Ile Glu Leu Leu Glu Met Thr Glu Val Asn Glu Gln Gln Ala
            260                 265                 270

Asp Phe Ile Glu Ser Met Lys Asn Ser Leu Thr Val Phe Asp Lys Tyr
        275                 280                 285

Phe Asn Thr Met Ile Ser Tyr Thr Lys Leu Leu Asn Asp Glu Asn Asp
    290                 295                 300

Tyr Lys Ala Thr Ile Ser Leu Glu Asp Phe Leu Ile Asp Leu Ser Val
305                 310                 315                 320

Glu Leu Glu Glu Leu Ser Thr Thr Tyr Gln Val Asp Tyr Gln Leu Val
                325                 330                 335

Lys Lys Thr Asp Leu Thr Thr Phe Tyr Gly Asn Thr Leu Ala Leu Ser
            340                 345                 350

Arg Ala Leu Ile Asn Ile Phe Val Asn Ala Cys Gln Tyr Ala Lys Glu
        355                 360                 365

Gly Glu Lys Ile Val Ser Leu Ser Ile Tyr Asp Asp Glu Lys Tyr Leu
    370                 375                 380

Tyr Phe Glu Ile Trp Asn Asn Gly His Pro Phe Ser Glu Gln Ala Lys
```

```
                385                 390                 395                 400
Lys Asn Ala Gly Lys Leu Phe Phe Thr Glu Asp Thr Gly Arg Ser Gly
                405                 410                 415

Lys His Tyr Gly Ile Gly Leu Ser Phe Ala Gln Gly Val Ala Leu Lys
                420                 425                 430

His Gln Gly Asn Leu Ile Leu Ser Asn Pro Gln Lys Gly Gly Ala Glu
                435                 440                 445

Val Ile Leu Lys Ile Lys Lys
                450                 455

<210> SEQ ID NO 25
<211> LENGTH: 460
<212> TYPE: PRT
<213> ORGANISM: Artificial Sequence
<220> FEATURE:
<223> OTHER INFORMATION: Synthetic Polypeptide

<400> SEQUENCE: 25

Met Ile Val Ser Met Asp Val Ile Lys Arg Val Tyr Gln Tyr Ala Glu
1               5                   10                  15

Pro Asn Leu Ser Leu Val Gly Trp Met Gly Met Leu Gly Phe Pro Ala
                20                  25                  30

Tyr Tyr Phe Ile Trp Glu Tyr Trp Phe Pro Gln Ser Tyr Glu Asn Leu
                35                  40                  45

Gly Leu Arg Cys Ala Ala Val Leu Phe Gly Gly Leu Val Phe Arg
                50                  55                  60

Asp Ser Met Pro Lys Lys Trp Gln Arg Tyr Met Pro Gly Tyr Phe Leu
65                  70                  75                  80

Phe Thr Ile Gly Phe Cys Leu Pro Phe Phe Ala Phe Met Met Leu
                85                  90                  95

Met Asn Asp Trp Ser Thr Ile Trp Ala Met Ser Phe Met Ala Ser Ile
                100                 105                 110

Phe Leu His Ile Leu Leu Val His Asp Thr Arg Val Met Ala Leu Gln
                115                 120                 125

Ala Leu Phe Ser Val Leu Val Ala Tyr Leu Ala Val Tyr Gly Leu Thr
                130                 135                 140

Asp Phe His Pro Thr Thr Leu Ile Glu Trp Gln Tyr Ile Pro Ile Phe
145                 150                 155                 160

Leu Phe Thr Tyr Val Phe Gly Asn Leu Cys Phe Phe Arg Asn Gln Ile
                165                 170                 175

Ser His Leu Ile Arg Glu Phe Ser Lys Asn Phe Gln Ala Val Gln Lys
                180                 185                 190

Ile Ala Leu Lys Met Gly Glu Ile Thr Thr Phe Pro Glu Gln Glu Glu
                195                 200                 205

Ser Lys Ile Ile Glu Phe Asp Gln Val Leu Asn Asn Leu Tyr Ser Lys
                210                 215                 220

Ser Lys Glu Leu Ala Phe Leu Ile Glu Ala Glu Arg His Glu Lys His
225                 230                 235                 240

Asp Leu Ser Phe Gln Val Ala Ala Leu Ser His Asp Val Lys Thr Pro
                245                 250                 255

Leu Thr Val Leu Lys Gly Asn Ile Glu Leu Leu Glu Met Thr Glu Val
                260                 265                 270

Asn Glu Gln Gln Ala Asp Phe Ile Glu Ser Met Lys Asn Ser Leu Thr
                275                 280                 285

Val Phe Asp Lys Tyr Phe Asn Thr Met Ile Ser Tyr Thr Lys Leu Leu
```

```
            290                 295                 300
Asn Asp Glu Asn Asp Tyr Lys Ala Thr Ile Ser Leu Glu Asp Phe Leu
305                 310                 315                 320

Ile Asp Leu Ser Val Glu Leu Glu Glu Leu Ser Thr Thr Tyr Gln Val
                325                 330                 335

Asp Tyr Gln Leu Val Lys Lys Thr Asp Leu Thr Thr Phe Tyr Gly Asn
            340                 345                 350

Thr Leu Ala Leu Ser Arg Ala Leu Ile Asn Ile Phe Val Asn Ala Cys
        355                 360                 365

Gln Tyr Ala Lys Glu Gly Glu Lys Ile Val Ser Leu Ser Ile Tyr Asp
    370                 375                 380

Asp Glu Lys Tyr Leu Tyr Phe Glu Ile Trp Asn Asn Gly His Pro Phe
385                 390                 395                 400

Ser Glu Gln Ala Lys Lys Asn Ala Gly Lys Leu Phe Phe Thr Glu Asp
                405                 410                 415

Thr Gly Arg Ser Gly Lys His Tyr Gly Ile Gly Leu Ser Phe Ala Gln
            420                 425                 430

Gly Val Ala Leu Lys His Gln Gly Asn Leu Ile Leu Ser Asn Pro Gln
        435                 440                 445

Lys Gly Gly Ala Glu Val Ile Leu Lys Ile Lys Lys
    450                 455                 460

<210> SEQ ID NO 26
<211> LENGTH: 238
<212> TYPE: PRT
<213> ORGANISM: Artificial Sequence
<220> FEATURE:
<223> OTHER INFORMATION: Synthetic Polypeptide

<400> SEQUENCE: 26

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
        50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
```

His Asn Glu Asp Tyr Thr Ile Val Glu Gln Tyr Glu Arg Ala Glu Gly
                195                 200                 205

Arg His Ser Thr Gly Gly Met Glu Thr Asp Glu Leu Tyr Lys
    210                 215                 220

225                 230                 235

<210> SEQ ID NO 27
<211> LENGTH: 176
<212> TYPE: DNA
<213> ORGANISM: Artificial Sequence
<220> FEATURE:
<223> OTHER INFORMATION: Synthetic Polynucleotide

<400> SEQUENCE: 27
agtcttataa ctatactgac aatagaaaca ttaacaaatc taaaacagtc ttaattctat      60
cttgagaaag tattggtaat aatattattg tcgataacgc gagcataata aacggctctg     120
attaaattct gaagtttgtt agatacaatg atttcgttcg aaggaactac aaaata        176

<210> SEQ ID NO 28
<211> LENGTH: 120
<212> TYPE: DNA
<213> ORGANISM: Artificial Sequence
<220> FEATURE:
<223> OTHER INFORMATION: Synthetic Polynucleotide

<400> SEQUENCE: 28
ccggctttag gtatagtgtg tatctcaatc cttggtatat tgaaaagaaa gactaaaaat      60
tgatagatta tatttcttca gaatgaatgg tataatgaag taatgagtac taaacaatcg    120

<210> SEQ ID NO 29
<211> LENGTH: 157
<212> TYPE: DNA
<213> ORGANISM: Artificial Sequence
<220> FEATURE:
<223> OTHER INFORMATION: Synthetic Polynucleotide

<400> SEQUENCE: 29
aaaactaaaa aaatattga cactctatca ttgatagagt ataattaaaa taagctccct      60
atcagtgata gagagagaaa acgtataaat tagggataaa ctatggaact tatgaaatag    120
attgaaatgg tttatctgtt accccgtatc aaaattt                            157

<210> SEQ ID NO 30
<211> LENGTH: 286
<212> TYPE: PRT
<213> ORGANISM: Artificial Sequence
<220> FEATURE:
<223> OTHER INFORMATION: Synthetic Polypeptide

<400> SEQUENCE: 30

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
                20                  25                  30

Asp Ala Glu Asp Gln Leu Gly Ala Arg Val Gly Tyr Ile Glu Leu Asp
            35                  40                  45

Leu Asn Ser Gly Lys Ile Leu Glu Ser Phe Arg Pro Glu Glu Arg Phe
        50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
              85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 31
<211> LENGTH: 858
<212> TYPE: DNA
<213> ORGANISM: Artificial Sequence
<220> FEATURE:
<223> OTHER INFORMATION: Synthetic Polynucleotide

<400> SEQUENCE: 31

| | | |
|---|---|---|
| atgagcattc aacatttag agttgcctta attcctttct tcgcggcttt ttgcttgccg | 60 |
| gttttcgctc atccagaaac tttggtaaag gttaagacg cagaagacca gttgggtgca | 120 |
| cgagtcgggt atattgaatt ggatcttaac agtggcaaga tattgagag tttcagaccg | 180 |
| gaagagcgat tcccgatgat gtctaccttc aaggtccttt tgtgtggagc tgttttgagc | 240 |
| cgagttgacg cgggtcaaga acagcttgga agacgaatac attactcaca aaacgattta | 300 |
| gtcgagtaca gcccagtgac agaaaaacat cttaccgatg gtatgacggt ccgagaattg | 360 |
| tgtagcgcgg caataaccat gagtgacaat acggctgcca atcttctttt gacgaccatc | 420 |
| ggaggaccta agaacttac cgcattttta cataatatgg gggaccatgt tactagattg | 480 |
| gatcgttggg aacctgagct taacgaagct attccaaacg acgaaagaga taccacaatg | 540 |
| ccggcggcca tggcgaccac tttacgtaag ctttaactg gtgaactttt gactttggcc | 600 |
| agccgacagc agcttattga ttggatgaa gcggacaaag tagcagggcc gttattacga | 660 |
| tctgcgttac cggcaggatg gtttatagcc gacaaaagcg gtgctggtga acgaggcagc | 720 |
| agaggtataa ttgcggcttt aggaccggac ggcaaaccaa gtagaatcgt agtcatatac | 780 |
| accacgggga gtcaggccac catggatgaa cgtaatcgtc aaatcgcgga aattggagct | 840 |
| tcattgataa agcactgg | 858 |

```
<210> SEQ ID NO 32
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 32

Cys Phe Phe Arg
1

<210> SEQ ID NO 33
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 33

Phe Leu Ile Glu Ala
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 34

Cys Phe Phe Arg Asn
1               5

<210> SEQ ID NO 35
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 35

Leu Ile Glu Ala
1

<210> SEQ ID NO 36
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 36

Cys Phe Phe Arg Asn Gln
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 37

Cys Phe Phe Arg Asn Gln Ile Ser
1               5
```

```
<210> SEQ ID NO 38
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 38

Cys Phe Phe Arg Asn Gln Ile Ser His Glu Thr
1               5                   10

<210> SEQ ID NO 39
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 39

Arg Glu Phe Ser
1

<210> SEQ ID NO 40
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 40

Cys Phe Phe Arg Asn Gln Ile
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 41

Leu Ile Arg Glu Phe Ser
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 42

His Leu Ile Arg Glu Phe Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 43

Cys Phe Phe Arg Asn Gln Ile Ser His
1               5

<210> SEQ ID NO 44
```

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 44

Cys Phe Phe Arg Asn Gln Ile Ser Ala
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 45

Cys Phe Phe Arg Asn Gln Ile Gly Ala
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 46

Cys Phe Phe Arg Asn Gln Ile Ala Ala
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 47

Cys Phe Phe Arg Asn Gln Ile Thr Ala
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 48

Cys Phe Phe Arg Asn Gln Ile Lys Ala
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 49

Cys Phe Phe Arg Asn Gln Ile Ser Gly
1               5

<210> SEQ ID NO 50
<211> LENGTH: 9
```

```
<212> TYPE: PRT
<213> ORGANISM: Artificial Sequence
<220> FEATURE:
<223> OTHER INFORMATION: Synthetic Polypeptide

<400> SEQUENCE: 50

Cys Phe Phe Arg Asn Gln Ile Ser Asp
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 51

Cys Phe Phe Arg Asn Gln Ile Ser Lys
1               5
```

US 10,802,021 B2

SYNTHETIC HYBRID RECEPTOR AND GENETIC CIRCUIT IN BACTERIA TO DETECT ENTERIC PATHOGENIC MICROORGANISMS

RELATED APPLICATIONS

This application is a national stage filing under 35 U.S.C. § 371 of PCT International Application, PCT/US2016/036703, entitled "SYNTHETIC HYBRID RECEPTOR AND GENETIC CIRCUIT IN BACTERIA TO DETECT ENTERIC PATHOGENIC MICROORGANISMS", filed Jun. 9, 2016, and claims the benefit under 35 U.S.C. § 119(e) of U.S. Provisional Application No. 62/172,971, entitled "SYNTHETIC HYBRID RECEPTOR AND GENETIC CIRCUIT IN BACTERIA TO DETECT ENTERIC PATHOGENIC MICROORGANISMS", filed Jun. 9, 2015, each of which are incorporated herein by reference.

FEDERALLY SPONSORED RESEARCH

This invention was made with government support under HDTRA1-15-1-0040 awarded by DTRA. The government has certain rights in the invention.

FIELD OF INVENTION

The present disclosure relates, in some aspects, to the field of biosynthetic engineering of microbes that can detect and/or kill a pathogen, such as Vibrio cholerae.

BACKGROUND OF INVENTION

In 2013, 47 countries reported a total of 129,064 cases of cholera including 2,102 deaths, giving a case-fatality rate (CFR) of 1.63%. Cholera represents an estimated burden of 1.4 to 4.3 million cases, and 28,000 to 142,000 deaths per year worldwide (World Health Organization: Weekly epidemiological record, No. 31, 1 Aug. 2014). A major obstacle to controlling cholera infection is the paucity of safe, efficient, and low cost treatments. Thus, there is a need for additional strategies to combat microbial infections, such as Vibrio cholerae.

SUMMARY OF INVENTION

This disclosure provides non-naturally occurring bacteria that detect the CAI-1 molecule made by Vibrio cholerae. The disclosure also describes coupling Vibrio cholerae detection with transcription modulation, enabling a biological response to pathogen detection, including expression of modules that kill and/or inhibit Vibrio cholerae infection or provide a colorimetric signal that the pathogen has been detected. This enables a rapid response to Vibrio cholerae infection in the human intestine, via the hybrid receptor, allowing clinicians to save the patient's life and/or reduce dissemination of the bacterial pathogen.

The present disclosure is based, at least in part, on unexpected findings showing that a hybrid receptor with a CqsS ligand binding domain and a NisK histidine kinase domain can be used in conjunction with a genetic circuit in an engineered microorganism (e.g., Lactococcus lactis) to express a reporter molecule in response to CAI-1, produced by Vibrio cholerae.

Thus, some aspects of the disclosure provide an engineered microorganism comprising a hybrid receptor with at least the binding portion of a CqsS polypeptide and a heterologous histidine kinase domain of a two-component system, and a genetic circuit responsive to the heterologous histidine kinase.

In some embodiments, the heterologous histidine kinase domain is from NisK or SpaK. In some embodiments, the heterologous histidine kinase domain comprises a glutamic acid to glycine mutation at position 225 relative to full length NisK (SEQ ID NO: 5). In some embodiments, the hybrid receptor comprises amino acids 221-447 of NisK (SEQ ID NO: 15) or amino acids 221-447 of NisK having an E225G mutation (SEQ ID NO: 3). In some embodiments, the hybrid receptor comprises the amino acid sequence of SEQ ID NO: 2. In some embodiments, the hybrid receptor comprises the amino acid sequence of SEQ ID NO: 1. In some embodiments, the hybrid receptor consists of the amino acid sequence of SEQ ID NO: 1.

In some embodiments, the genetic circuit comprises a first promoter that is operably linked to a nucleic acid sequence encoding the hybrid receptor and a second promoter that is responsive to the heterologous histidine kinase domain and is operably linked to a nucleic acid sequence encoding an output molecule. In some embodiments, the first promoter is inducible. In some embodiments, the first promoter is constitutive. In some embodiments, the first promoter is a nisR promoter. In some embodiments, the second promoter is a nisA promoter.

In some embodiments, the genetic circuit comprises a first promoter that is operably linked to a nucleic acid sequence encoding the hybrid receptor, a second promoter that is operably linked to a nucleic acid sequence encoding a repressor molecule, and a third promoter that is operably linked to a nucleic acid sequence encoding an output molecule, wherein the second promoter is responsive to the heterologous histidine kinase domain, and wherein the third promoter is responsive to the repressor molecule, and wherein the repressor molecule binds to the third promoter and represses transcription of the output molecule. In some embodiments, the first promoter is inducible. In some embodiments, the first promoter is constitutive. In some embodiments, the first promoter is a nisR promoter. In some embodiments, the second promoter is a nisA promoter. In some embodiments, the third promoter is a xyltet2 promoter.

In some embodiments, the output molecule is an antimicrobial peptide, a, lysing polypeptide, a reporter polypeptide or a nucleic acid. In some embodiments, the output molecule is mCherry, or β-lactamase. In some embodiments, the mCherry comprises the amino acid sequence as set forth in SEQ ID NO: 26. In some embodiments, the β-lactamase comprises the amino acid sequence as set forth in SEQ ID NO: 30.

Aspects of the disclosure relate to a method of detecting and/or treating a cholera infection comprising administering to a subject having or at risk of having a cholera infection any of the engineered microorganisms, described herein. In some embodiments, the subject having or at risk of having a cholera infection is a subject in an area of cholera outbreak. In some embodiments, the methods further include administering to the subject an antibiotic agent effective for killing Vibrio cholerae when the engineered microorganism expresses a detectable output molecule.

Aspects of the disclosure relate to a method of detecting a cholera infection comprising obtaining a biological sample from a subject having or at risk of having a cholera infection, and contacting the biological sample with any of the engineered microorganisms provided herein. In some embodiments, the biological sample is a fecal sample. In some embodiments, the method further includes contacting a mixture of the biological sample and the microorganism with a substrate. In some embodiments, the substrate is a colorimetric substrate. In some embodiments, the substrate is nitrocefin. In some embodiments, the method further includes detecting a color change of a mixture of the biological sample, the microorganism, and the substrate. In some embodiments, the detecting comprises spectrophotometry.

Aspects of the disclosure relate to a method of detecting and treating a cholera infection in a subject comprising obtaining a biological sample from a subject having or at risk of having a cholera infection, contacting the biological sample with any of the engineered microorganisms provided herein, determining if the subject has a cholera infection, and administering to the subject any of the engineered microorganisms provided herein if it is determined that the subject has a cholera infection.

Aspects of the disclosure relate to a hybrid receptor comprising at least the binding portion of a CqsS polypeptide and a heterol ogous histidine kinase domain of a two-component system. In some embodiments, the heterologous histidine kinase domain is from NisK or SpaK. In some embodiments, the histidine kinase domain comprises a glutamic acid to glycine mutation at position 225 relative to full length NisK (SEQ ID NO: 5). In some embodiments, the hybrid receptor comprises amino acids 221-447 of NisK (SEQ ID NO: 15) or amino acids 221-447 of NisK having an E225G mutation (SEQ ID NO: 3). In some embodiments, the hybrid receptor comprises the amino acid sequence of SEQ ID NO: 2. In some embodiments, the hybrid receptor comprises the amino acid sequence of SEQ ID NO: 1. In some embodiments, the hybrid receptor consists of the amino acid sequence SEQ ID NO: 1. In some embodiments, the hybrid receptor comprises an amino acid sequence selected from the group consisting of (SEQ ID NOs: 6-13). In some embodiments, the hybrid receptor comprises an amino acid sequence selected from the group consisting of (SEQ ID NOs: 16-25).

BRIEF DESCRIPTION OF THE DRAWINGS

The accompanying drawings are not intended to be drawn to scale. For purposes of clarity, not every component may be labeled in every drawing.

FIGS. 3A-3B are schematics of the CAI-I detection circuits. FIG. 3A shows that the recognition of CAI-1 by the hybrid receptor causes repression of the nisA promoter, resulting in decreased expression of the output module that is operably linked to the nisA promoter. FIG. 3B shows the Signal Inverter design, where detection of CAI-1 by the hybrid receptor represses TetR expression from the nisA promoter, thereby allowing increased expression of the output module controlled by the TetR-repressible xyltet2 promoter.

FIG. 10A shows exemplary output results of β-lactamase assay using *L. lactis* that expresses β-lactamase in response to binding the CqsA polypeptide of *V. cholerae* (L.(pHTR)). FIG. 10B shows exemplary spectrophotometer readings of a β-lactamase assay over the course of 30 minutes using the β-lactamase assay shown in FIG. 10A.

DETAILED DESCRIPTION OF DISCLOSURE

Figure 1:
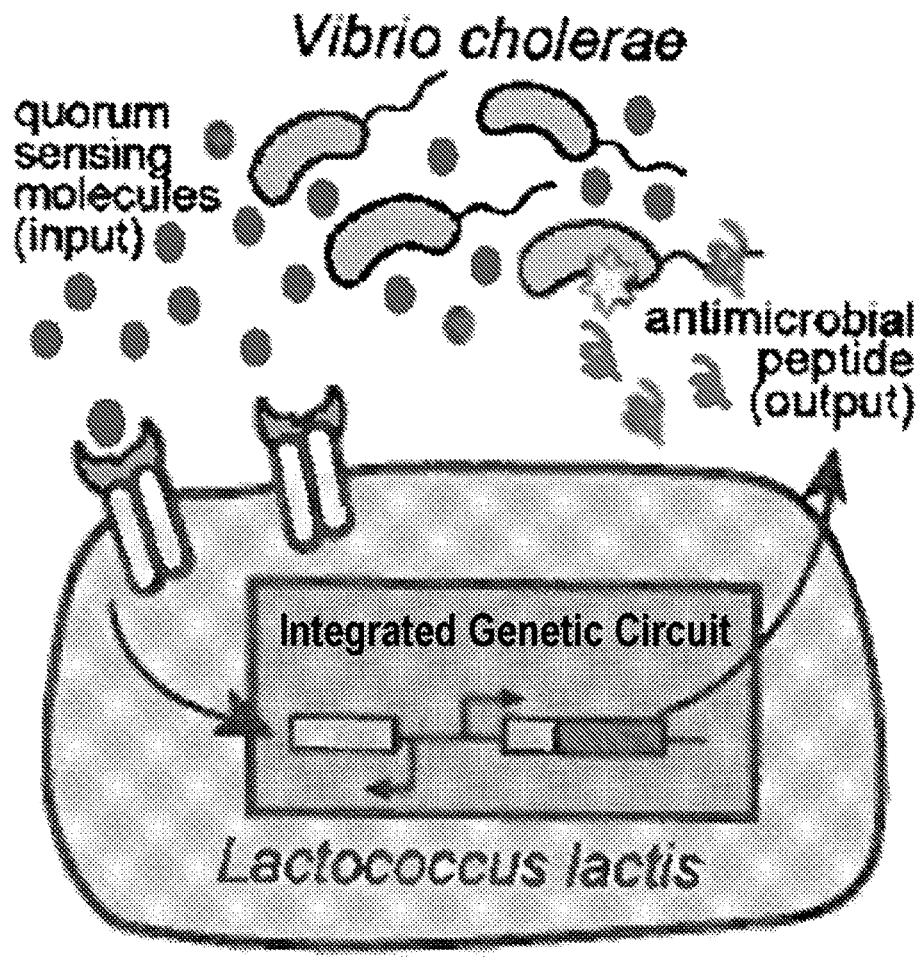
FIG. 1 is a schematic of the genetically engineered (thus, non-naturally occurring) probiotic bacteria *Lactococcus lactis* that is designed to sense and kill the cholera pathogen, *Vibrio cholerae*.

Provided herein are engineered and thus non-naturally occurring microorganisms and hybrid receptors, and methods for detecting and/or killing pathogenic microbes using such microorganisms and receptors.

Engineered Microorganisms

Some aspects of the present disclosure are directed to engineered microorganisms having a hybrid receptor and a genetic circuit responsive to the hybrid receptor. An "engineered microorganism," as used herein, refers to a microorganism that does not occur in nature. Engineered microorganisms of the present disclosure, in some embodiments, contain one or more exogenous nucleic acids (i.e., nucleic acids that the microorganism would not normally contain) or nucleic acids that do not occur in nature (e.g., an engineered nucleic acid encoding a heterologous histidine kinase of a two-component system). Accordingly, an engineered microorganism can be a microorganism that has been designed, produced, prepared, synthesized, manufactured and/or manipulated by a human.

In some embodiments, an engineered microorganism contains an engineered nucleic acid. A "nucleic acid" is at least two nucleotides covalently linked together, which in some instances may contain phosphodiester bonds (e.g., a phosphodiester "backbone"). An "engineered nucleic acid," as used herein, is a nucleic acid that does not occur in nature. It should be understood, however, that while an engineered nucleic acid as a whole is not naturally-occurring, it may include nucleotide sequences that occur in nature. In some embodiments, an engineered nucleic acid comprises nucleotide sequences from different organisms (e.g., from different species). For example, in some embodiments, an engineered nucleic acid includes a bacterial nucleotide sequence, a murine nucleotide sequence, a human nucleotide sequence, and/or a viral nucleotide sequence. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified in vitro or chemically synthesized (e.g., using a nucleic acid automated synthesizer). A synthetic nucleic acid includes nucleic acids that are chemically modified, or otherwise modified, but can base pair with naturally-occurring nucleic acid molecules. Recombinant and synthetic nucleic acids also include nucleic acids that result from the replication of either of the foregoing.

In some embodiments, an engineered microorganism contains one or more mutations in the genome of the microorganism. In some embodiments, an engineered microorganism contains an exogenous independently-replicating nucleic acid (e.g., an engineered nucleic acid present on an episomal vector). In some embodiments, an engineered microorganism is produced by introducing a foreign or exogenous nucleic acid into a cell. A nucleic acid may be introduced into a cell by conventional methods, such as, for example, electroporation (see, e.g., Heiser W. C. Transcription Factor Protocols: Methods in Molecular Biology™ 2000; 130: 117-134), chemical (e.g., calcium phosphate or lipid) transfection (see, e.g., Lewis W. H., et al., Somatic Cell Genet. 1980 May; 6(3): 333-47; Chen C., et al., Mol Cell Biol. 1987 August; 7(8): 2745-2752), fusion with bacterial protoplasts containing recombinant plasmids (see, e.g., Schaffner W. Proc Natl Acad Sci USA. 1980 April; 77(4): 2163-7), transduction, conjugation, or microinjection of purified DNA directly into the nucleus of the cell (see, e.g., Capecchi M. R. Cell. 1980 November; 22(2 Pt 2): 479-88).

In some embodiments, the engineered microorganisms of the present disclosure are prokaryotes (e.g., bacterial cells). In some embodiments, the engineered microorganisms are bacterial cells. Bacterial cells of the present disclosure include bacterial subdivisions of Eubacteria and Archaebacteria. Eubacteria can be further subdivided into gram-positive and gram-negative Eubacteria, which depend upon a difference in cell wall structure. Also included herein are those classified based on gross morphology alone (e.g., cocci, bacilli). In some embodiments, the bacterial cells are Gram-negative cells, and in some embodiments, the bacterial cells are Gram-positive cells. Examples of bacterial cells of the present disclosure include, without limitation, cells from *Lactobacillus* spp., *Lactococcus* spp., *Bacillus* spp., *Enterobacter* spp., *Yersinia* spp., *Escherichia* spp., *Klebsiella* spp., *Acinetobacter* spp., *Bordetella* spp., *Neisseria* spp., *Aeromonas* spp., Franciesella spp., *Corynebacterium* spp., *Citrobacter* spp., *Chlamydia* spp., Hemophilus spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Erysipelothrix* spp., *Salmonella* spp., *Streptomyces* spp., *Bacteroides* spp., *Prevotella* spp., *Clostridium* spp., or *Bifidobacterium* spp.

In some embodiments, the engineered microorganisms are non-pathogenic bacteria that are derived from a normal internal ecosystem such as bacterial flora. In some embodiments, the engineered microorganisms are non-pathogenic bacteria that are derived from a normal internal ecosystem of the gastrointestinal tract. Non-limiting examples of non-pathogenic bacteria that are part of the normal flora in the gastrointestinal tract include bacteria from the genera *Bacteroides, Clostridium, Fusobacterium, Eubacterium, Ruminococcus, Peptococcus, Peptostreptococcus, Bifidobacterium, Escherichia* and *Lactobacillus.*

In some embodiments, bacterial cells of the disclosure are anaerobic bacterial cells (e.g., cells that do not require oxygen for growth). Anaerobic bacterial cells include facultative anaerobic cells such as, for example, *Escherichia coli, Shewanella oneidensis* and *Listeria monocytogenes.* Anaerobic bacterial cells also include obligate anaerobic cells such as, for example, *Bacteroides* and *Clostridium* species. In humans, for example, anaerobic bacterial cells are most commonly found in the gastrointestinal tract.

In some embodiments, the engineered microorganisms are lactic acid bacteria (LAB). "Lactic acid bacteria," as used herein, refer to Gram-positive, non-spore forming cocci, coccobacilli or rods with low GC content (i.e., a DNA base composition of less than 53 mol % G+C). Lactic acid bacteria generally are non-respiratory and lack catalase. Typically, lactic acid bacteria ferment glucose primarily to lactic acid, or to lactic acid, CO2 and ethanol. In some embodiments, the lactic acid bacteria are, without limitation, *Lactococcus lactis, Lactobacillus acidophilus, Lactobacillus gasseri, Leuconostoc lactis, Lactobacillus brevis, Lactobacillus plantarum, Lactobacillus casei, Lactobacillus gasseri, Lactobacillus helveticus, Streptococcus pyogenes, Streptococcus agalactiae, Streptococcus pneumoniae,* or *Streptococcus zooepidemicus.*

In some embodiments, the engineered microorganisms are bacteria in which the *Lactococcus lactis* histidine kinase NisK is functional, or can function. A histidine kinase (e.g., NisK) is considered functional in a bacteria if activation of the histidine kinase (e.g., via ligand binding and phosphorylation) causes a change in transcriptional activity of the bacteria (e.g., via phosphorylation and activation of a response regulator). Such bacteria include, but are not limited to, *Lactococcus lactis, Enterococcus faecalis, Staphylococcus simulans, Bacillus subtilis, Lactobacillus brevis, Lactobacillus helveticus, Lactobacillus plantarum, Streptococcus pyogenes, Streptococcus agalactiae, Streptococcus pneumoniae* and *Streptococcus zooepidemicus.*

Hybrid Receptors

Aspects of the disclosure relate to engineered microorganisms having a cell surface hybrid receptor comprising at least the binding portion of a CqsS polypeptide and a heterologous histidine kinase of a two-component system. A "hybrid receptor," as used herein, refers to a non-naturally occurring protein-based receptor that comprises amino acid sequences from two or more receptors. In some embodiments, the hybrid receptor comprises amino acid sequences that are derived from different organisms. Protein sequences that are derived from different organisms are referred to herein as "heterologous sequences".

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins.

In some embodiments, the hybrid receptor contains at least the binding portion of a CqsS polypeptide. A "CqsS polypeptide", as used herein, refers to a histidine kinase from a *Vibrio* species (e.g., *Vibrio cholerae, Vibrio harveyi* and *Vibrio parahaemolyticus*) that acts as the receptor for a CAI-1 autoinducer. In *Vibrio cholerae*, CAI-1 is (S)-3-hydroxytridecan-4-one (C10-CAI-1), which is produced by the CqsA synthase. Typically, bacteria (e.g., *Vibrio cholerae*) coordinate group behaviors by producing, detecting, and collectively responding to extracellular signaling molecules called autoinducers (e.g., CAI-1). This process is called quorum sensing. Quorum sensing involves detection (e.g., by a CqsS polypeptide) of the density-dependent accumulation of autoinducers that elicit population-wide changes in gene expression. Exemplary CqsS polypeptides are known in the art and have been described previously. For example CqsS polypeptides, without limitation, have been described in Ng W. L., et al., "Signal production and detection specificity in *Vibrio* CqsA/CqsS quorum-sensing systems," *Mol Microbiol*, 2011 March; 79(6):1407-17 and in Xiaobo K., et al., "CqsA-CqsS quorum-sensing signal-receptor specificity in *Photobacterium angustum*," *Mol Microbiol*, 2014 February; 91(4): 821-833, the contents of each of which are hereby incorporated by reference. In some embodiments, the CqsS polypeptide is from *Vibrio cholerae*. In some embodiments, the CqsS polypeptide comprises SEQ ID NO: 4. In some embodiments, the CqsS polypeptide consists of SEQ ID NO: 4. In some embodiments, the CqsS polypeptide consists essentially of SEQ ID NO: 4.

In some embodiments, the hybrid receptor comprises "the binding portion of a CqsS polypeptide." As used herein, "the binding portion of a CqsS polypeptide" refers to a portion of a CqsS polypeptide that is capable of binding an autoinducer (e.g., CAI-1). Thus, in some embodiments, the binding portion of a CqsS polypeptide refers to a portion of a CqsS polypeptide that is capable of binding to a CAI-1-like molecule. Exemplary CAI-1-like molecules include, but are not limited to, C8-CAI-1, Ea-C8-CAI-1 and Ea-C10-CAI-1, which have been described previously (Ng W. L., et al., "Signal production and detection specificity in *Vibrio* CqsA/CqsS quorum-sensing systems," *Mol Microbiol*, 2011 March; 79(6):1407-17; and Xiaobo K., et al., "CqsA-CqsS quorum-sensing signal-receptor specificity in *Photobacterium angustum*," *Mol Microbiol*, 2014 February; 91(4): 821-833). In some embodiments, the binding portion of a CqsS polypeptide refers to a portion of a CqsS polypeptide that is capable of binding to (S)-3-hydroxytridecan-4-one (i.e., C10-CAI-1).

In some embodiments, the binding portion of a CqsS polypeptide comprises a full length CqsS polypeptide, for example the CqsS polypeptide of SEQ ID NO: 4. In some embodiments, the binding portion of a CqsS polypeptide is an N-terminal portion of a CqsS polypeptide. In some embodiments, the binding portion of a CqsS polypeptide includes at least the first 100 amino acids (aa), at least the first 110 aa, at least the first 120 aa, at least the first 130 aa, at least the first 140 aa, at least the first 150 aa, at least the first 160 aa, at least the first 170 aa, at least the first 180 aa, at least the first 190 aa, at least the first 200 aa, at least the first 210 aa, at least the first 220 aa, at least the first 230 aa, at least the first 240 aa, at least the first 250 aa, at least the first 260 aa, at least the first 270 aa, at least the first 280 aa, at least the first 290 aa, or at least the first 300 aa of a CqsS polypeptide or of SEQ ID NO: 4, from the N-terminus. In some embodiments, the binding portion of a CqsS polypeptide includes at least the first 15%, at least the first 20%, at least the first 25%, at least the first 30%, at least the first 35%, at least the first 40%, at least the first 45%, at least the first 50%, at least the first 55%, at least the first 60%, at least the first 65%, or at least the first 70% from the N-terminus of a full length CqsS polypeptide or of SEQ ID NO: 4. In some embodiments, the binding portion of a CqsS polypeptide includes amino acids 1-177 of a CqsS polypeptide or of SEQ ID NO: 2.

In some embodiments, the hybrid receptor of the present disclosure comprises a heterologous histidine kinase domain of a two-component system. A "heterologous histidine kinase domain of a two-component system" or a "heterologous two-component histidine kinase domain," as used herein, refers to a histidine kinase domain from a two-component system that is cloned or derived from an organism other than a *Vibrio* species. In some embodiments, the histidine kinase domain from a two-component system is cloned or derived from an organism other than *Vibrio cholerae*. Two-component regulatory systems serve as a basic stimulus-response coupling mechanism to allow organisms to sense and respond to changes in many different environmental conditions. See e.g., Stock A. M., et al., "Two-component signal transduction," *Annu. Rev. Biochem.*, 2000, 69 (1): 183-215, the contents of which are hereby incorporated by reference. Typically two-component systems include a membrane-hound histidine kinase that senses a specific environmental stimulus (e.g., CAI-I) and a corresponding response regulator that mediates the cellular response (e.g., through differential expression of target genes). Histidine kinases of two-component systems are known in the art and can be identified and classified by virtue of their conserved cytoplasmic kinase domains. For example, a number of histidine kinases of two-component systems have been described in Mascher T., et al., "Stimulus Perception in Bacterial Signal-Transducing Histidine Kinases", Microbiol Mol Biol Rev., 2006 December; 70(4): 910-938, the contents of which are hereby incorporated by reference. It should be appreciated that the histidine kinases disclosed in the cited reference and the instant specification are not meant to be limiting and additional histidine kinases of two-component systems fall within the scope of this disclosure. In some embodiments, the histidine kinase domain of a two-component system is derived from a two-component histidine kinases, such as but not limited to, NisK, SpaK, EnvZ, CheA, NtrB, PhoQ, TorS, VirA, LuxQ, VarS, KdpD, YycF, CpxA and RcsC.

In some embodiments, the heterologous histidine kinase domain comprises the kinase domain of a two-component histidine kinase. In some embodiments, the heterologous histidine kinase domain of a two-component system comprises a histidine kinase domain from the histidine kinase NisK (SEQ ID NO: 5), or the histidine kinase SpaK (SEQ ID NO: 14). In some embodiments, the heterologous histidine kinase domain comprises a C-terminal portion of a two-component histidine kinase. In some embodiments, heterologous histidine kinase domain includes at least the last 150 aa, at least the last 160 aa, at least the last 170 aa, at least the last 180 aa, at least the last 190 aa, at least the last 200 aa, at least the last 210 aa, at least the last 220 aa, at least the last 230 aa, at least the last 240 aa, at least the last 250 aa, at least the last 260 aa, at least the last 270 aa, at least the last 280 aa, at least the last 290 aa, at least the last 300 aa, at least the last 320 aa, at least the last 340 aa, at least the last 360 aa, or at least the last 380 aa of a two-component histidine kinase, or of SEQ ID NO: 5, or of SEQ ID NO: 13, where the last amino acid is the C-terminal amino acid. In some embodiments, the heterologous histidine kinase domain includes at least the last 15%, at least the last 20%, at least the last 25%, at least the last 30%, at least the last 35%, at least the last 40%, at least the last 45%, at least the last 50%, at least the last 55%, at least the last 60%, at least the last 65%, or at least the last 70% of a full length two-component histidine kinase, or of SEQ ID NO: 5, or of SEQ ID NO: 13. In some embodiments, the heterologous histidine kinase domain comprises amino acids 221-447 of NisK (e.g., SEQ ID NO: 15). In some embodiments, the heterologous histidine kinase domain comprises a glutamic acid to glycine mutation. In some embodiments, the heterologous histidine kinase domain comprises amino acids 221-447 of NisK, wherein there is a glycine at position 225, rather than a glutamic acid (e.g., SEQ ID NO: 3).

In some embodiments, the hybrid receptor of the present disclosure comprises at least the binding portion of a CqsS polypeptide and a heterologous histidine kinase domain of a two-component system. In some embodiments, the hybrid receptor comprises SEQ ID NO: 2 and either SEQ ID NO: 3 or SEQ ID NO: 15. In some embodiments, the hybrid receptor comprises any one of SEQ ID NOs: 1, 6-13 and 16-26. In some embodiments, the hybrid receptor consists of any one of SEQ ID NOs: 1, 6-13 and 16-26. In some embodiments, the hybrid receptor consists essentially of any one of SEQ ID NOs: 1, 6-13 and 16-26.

The invention contemplates variants of any of the hybrid receptor amino acid sequences, any of the heterologous histidine kinase amino acid sequences, or any of the CqsS polypeptide amino acid sequences described herein. As used herein, a variant of a hybrid receptor amino acid sequence, a heterologous histidine kinase amino acid sequence or a CqsS polypeptide amino acid sequence is an amino acid sequence that is not identical to, but shares a degree of homology with the hybrid receptor amino acid sequence, the heterologous histidine kinase amino acid sequence or the CqsS polypeptide amino acid sequences respectfully described herein. As used herein, the term "homology" refers to the overall relatedness between proteins. In some embodiments, proteins are considered to be "homologous" to one another if their amino acid sequences are at least 70%, at least 75%, at least 80%, at least 85%, at least 90%, at least 95%, or at least 99% identical. Accordingly, proteins that are homologous to any of the hybrid receptor amino acid sequences, heterologous histidine kinase amino acid sequences or CqsS polypeptide amino acid sequences, described herein, are also within the scope of this disclosure.

Genetic Circuits

In some embodiments, the engineered microorganisms of the present disclosure comprise genetic circuits responsive to any of the heterologous histidine kinases described herein. A "genetic circuit," as used herein, refers to a functional cluster of genes or nucleic acids that impact each other's expression through inducible transcription factors or cis-regulatory elements. A genetic circuit is "responsive to a heterologous histidine kinase" if the histidine kinase modulates the expression of at least one nucleic acid or gene of the genetic circuit. Typically, activation or repression of transcription of a nucleic acid or gene occurs via signal transduction following activation of a heterologous histidine kinase in response to binding a ligand (e.g., CAI-1). For example, phosphorylation of a heterologous histidine kinase (e.g., in response to binding a ligand such as CAI-1) may activate or repress transcription of a nucleic acid or gene of the genetic circuit. Without wishing to be bound by any theory, signal transduction may occur through the transfer of phosphoryl groups from adenosine triphosphate (ATP) to a specific histidine residue in the heterologous histidine kinases (e.g., by an autophosphorylation reaction). Molecules referred to as response regulators may then be phosphorylated on an aspartate residue. Phosphorylation of the response regulators can cause a change in the conformation of the response regulators, typically activating an attached output domain, which then may lead to the activation or repression of expression of target genes or nucleic acids. Accordingly, in some embodiments, a gene circuit comprises a gene that is transcriptionally activated when the hybrid receptor is bound by a ligand (e.g., CAI-1). In some embodiments, a gene circuit comprises a gene that is transcriptionally repressed when a heterologous histidine kinase is bound by a ligand (e.g., CAI-1).

In some embodiments the genetic circuit comprises a first promoter that is operably linked to a nucleic acid sequence encoding the hybrid receptor and a second promoter that is responsive to the heterologous histidine kinase and is operably linked to a nucleic acid sequence encoding an output molecule. As one non-limiting example, in response to binding the hybrid receptor, CAI-1 inhibits (or activates) transcription of an output molecule (see e.g., FIG. 3B). It should be appreciated that the genetic circuits, described herein, may comprise one or more nucleic acids which may or may not be linked.

The genetic circuits of the present disclosure may comprise one or more promoters operably linked to a nucleotide sequence encoding, for example, a hybrid receptor or output molecule. A "promoter" refers to a control region of a nucleic acid sequence at which initiation and rate of transcription of the remainder of a nucleic acid sequence are controlled. A promoter may also contain sub-regions to which regulatory proteins and molecules may bind, such as RNA polymerase and other transcription factors. Promoters may be constitutive, inducible, activatable, repressible, or any combination thereof. In some embodiments, the genetic circuit comprises at least 1 at least 2, at least 3, at least 4, at least 5, at least 6, at least 7, at least 8, at least 9, at least 10, at least 15, at least 20, at least 30 or at least 50 promoters. In some embodiments one or more of the promoters may be a nisA promoter, a nisR promoter and/or a xyltet2 promoter. In some embodiments one or more of the promoters comprises SEQ ID NOs: 27, 28, and/or 29. In some embodiments one or more of the promoters consists of SEQ ID NOs: 27, 28, and/or 29. In some embodiments one or more of the promoters consists essentially of SEQ ID NOs: 27, 28, and/or 29.

A promoter drives expression or transcription of the nucleic acid sequence to which it is operatively linked. In some embodiments, the promoter is operably linked to a nucleic acid encoding a hybrid receptor or an output molecule. A promoter is considered to be "operably linked" when it is in a correct functional location and orientation in relation to the nucleic acid sequence it regulates, thereby resulting in the ability of the promoter to drive transcription initiation or expression of that sequence.

A promoter may be one naturally associated with a gene or sequence, as may be obtained by isolating the 5' non-coding sequences located upstream of the coding segment of a given gene or sequence (e.g., an endogenous promoter).

In some embodiments, a coding nucleic acid sequence may be positioned under the control of a recombinant or heterologous promoter, which refers to a promoter that is not normally associated with the coding sequence in its natural environment. Such promoters may include promoters of other genes; promoters isolated from another cell type; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202 and 5,928,906).

In some embodiments, the promoters described herein are "constitutive promoters," which are promoters that are constitutively active in the cell (i.e., not regulated in response to specific stimuli). Constitutive promoters (e.g., constitutive bacterial promoters) are known in the art and include, without limitation, P32, P57, P59, Pxyl, PclpB, PrepU and PlepA.

In some embodiments, the promoters described herein are "inducible promoters," which are promoters that are active or inactive in response to a particular stimulus, condition, or an inducer signal. An inducer signal may be endogenous or a normally exogenous condition (e.g., light), compound (e.g., chemical or non-chemical compound) or protein that contacts an inducible promoter in such a way as to activate transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve direct activation of or indirect activation of a promoter as may occur by inactivation of a repressor molecule that prevents transcription from the promoter. A "repressor molecule" is any molecule that can bind to a promoter and prevent transcription of a gene or nucleic acid sequence to which the promoter is operably linked. Conversely, deactivation of transcription may involve direct action on a promoter to prevent transcription or indirect action on a promoter by activating a repressor that then acts on the promoter.

The administration or removal of an inducer signal results in a switch between activation and inactivation of the transcription of the operably linked nucleic acid sequence. Thus, the active state of a promoter operably linked to a nucleic acid sequence refers to the state in which the promoter is actively regulating transcription of the nucleic acid sequence (i.e., the linked nucleic acid sequence is expressed). Conversely, the inactive state of a promoter operably linked to a nucleic acid sequence refers to the state when the promoter is not actively regulating transcription of the nucleic acid sequence (i.e., the linked nucleic acid sequence is not expressed).

An inducible promoter of the present disclosure may be induced by (or repressed by) one or more physiological condition(s), such as changes in light, pH, temperature, radiation, osmotic pressure, saline gradients, cell surface binding, and the concentration of one or more extrinsic or intrinsic inducing agent(s). An extrinsic inducer signal may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters of the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (ATc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

Other inducible promoter systems are known in the art and may be used in accordance with the present disclosure.

In some embodiments, inducible promoters of the present disclosure function in prokaryotic cells (e.g., bacterial cells). Examples of inducible promoters for use in prokaryotic cells include, without limitation, bacteriophage promoters (e.g. Pls icon, T3, T7, SP6, PL) and bacterial promoters (e.g., Pbad, PmgrB, Ptrc2, Plac/ara, Ptac, Pm), or hybrids thereof (e.g. PLlacO, PLtetO). Examples of bacterial promoters for use in accordance with the present disclosure include, without limitation, positively regulated $E.$ $coli$ promoters such as positively regulated σ70 promoters (e.g., inducible pBad/araC promoter, Lux cassette right promoter, modified lambda Prm promote, plac Or2-62 (positive), pBad/AraC with extra REN sites, pBad, P(Las) TetO, P(Las) CIO, P(Rh1), Pu, FecA, pRE, cadC, hns, pLas, pLux), GS promoters (e.g., Pdps), 632 promoters (e.g., heat shock) and σ54 promoters (e.g., glnAp2); negatively regulated $E.$ $coli$ promoters such as negatively regulated σ70 promoters (e.g., Promoter (PRM+), modified lamdba Prm promoter, TetR-TetR-4C P(Las) TetO, P(Las) CIO, P(Lac) IQ, RecA_DlexO_D-LacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLaclq, rrnB P1, cadC, hns, PfhuA, pBad/araC, nhaA, OmpF, RcnR), GS promoters (e.g., Lutz-Bujard LacO with alternative sigma factor ∝38), σ32 promoters (e.g., Lutz-Bujard LacO with alternative sigma factor σ32), and σ54 promoters (e.g., glnAp2); negatively regulated $B.$ $subtilis$ promoters such as repressible $B.$ $subtilis$ GA promoters (e.g., Gram-positive IPTG-inducible, Xyl, hyper-spank) and σB promoters. Other inducible microbial promoters may be used in accordance with the present disclosure.

In some embodiments, the genetic circuit includes a first promoter that is operably linked to a nucleic acid sequence encoding a hybrid receptor, a second promoter that is operably linked to a nucleic acid sequence encoding a repressor molecule, and a third promoter that is operably linked to a nucleic acid sequence encoding an output molecule. In some embodiments, the second promoter is responsive to the heterologous histidine kinase. In some embodiments the third promoter is responsive to the repressor molecule. In some embodiments the repressor molecule binds to the third promoter and represses transcription. As one non-limiting example, in response to binding CAI-1, a hybrid receptor inhibits transcription of a tetR repressor molecule, which activates the transcription of an output molecule (see e.g., FIG. 3B).

The term "output molecule," as used herein refers to a nucleic acid or protein that is expressed in response to the state of the hybrid receptor. In some embodiments, the output molecule is expressed when the hybrid receptor is bound to a ligand CAI-1). In some embodiments, the output molecule is expressed when the hybrid receptor is not bound to a ligand.

In some embodiments, the output molecule is an antimicrobial peptide, a lysing polypeptide, a reporter polypeptide or a nucleic acid. In some embodiments, the output molecule is an antimicrobial peptide. In some embodiments, the antimicrobial peptide is a bacteriocin such as a class I bacteriocin (e.g., small peptide inhibitors that include nisin and other lantibiotics), a class II bacteriocin (e.g., small heat-stable proteins such as pediocin-like bacteriocins, two-peptide bacteriocins, cyclic bacteriocins, single-peptide bacteriocins, and non-pediocin like bacteriocins), a class III bacteriocin (e.g., large heat-labile protein bacteriocins such as the bacteriolysin lysostaphin and membrane potential disrupting bacteriocins), or a class IV bacteriocin (e.g., complex bacteriocins containing lipid or carbohydrate moieties). In some embodiments, the output molecule is a bacteriocin that is specific for *Vibrio cholerae*. In some embodiments, the bacteriocin is selected from the group consisting of Morricin 269, Kurstacin 287, Kenyacin 404, Entomocin 420 and Tol-worthcin 524. In some embodiments, the cell produces a secreted factor by cell suicide. In certain embodiments, the secreted factor is a chemokine-derived antimicrobial peptide (CDAP). In some embodiments, the lysin is produced together with an immunity protein that protects the cell that secretes the lysin from being destroyed by the lysin. In some embodiments, the lysin lyses the cell to release the lysin molecules from the cell. It should be appreciated that the antimicrobial peptides, described herein, are not meant to be limiting and that additional antimicrobial peptides are within the scope of this disclosure.

In some embodiments, the output molecule is a lysing polypeptide. In some embodiments, the lysing polypeptide can be any of the lysing antimicrobial peptides described herein. In some embodiments, the lysing peptide is lysozyme, holin, or endolysin. It should be appreciated that the lysing polypeptides, described herein, are not meant to be limiting and that additional lysing polypeptides are within the scope of this disclosure.

In some embodiments, the output molecule is a reporter polypeptide. In some embodiments, the reporter polypeptide is a fluorescent polypeptide. Fluorescent polypeptides include, without limitation cyan fluorescent protein (e.g., AmCyan1), green fluorescent protein (e.g., EGFP, AcGFP1, and ZsGreen1), yellow fluorescent protein (e.g., ZsYellow1 and mBananna), orange fluorescent protein (e.g., mOrange and mOrange2), red fluorescent protein (e.g., DsRed, tdTomato, mStrawberry and mCherry), and far-red fluorescent protein (e.g., HcRed1, mRaspberry and mPlum). In some embodiments, the reporter polypeptide is mCherry. In some embodiments the reporter polypeptide comprises SEQ ID NO: 26.

In some embodiments, the reporter polypeptide is a peptide that acts on, e.g., cleaves, a substrate, e.g., a colorimetric substrate, which may be detected visually or via a spectrophotometer when the colorimetric substrate is cleaved by the peptide. In some embodiments, the reporter polypeptide is β-galactosidase, which can cleave X-gal, a colorless analog of lactose that forms 5-bromo-4-chloro-indoxyl upon cleavage, which then spontaneously dimerizes and oxidizes to form a bright blue insoluble pigment 5,5'-dibromo-4,4'-dichloro-indigo. In some embodiments, the reporter polypeptide is alkaline phosphatase, which can cleave a 5-Bromo-4-Chloro-3-Indolyl Phosphate (BCIP) substrate to produce insoluble NBT that is blue to purple in color. In some embodiments, the reporter polypeptide is β-lactamase, which can cleave the substrate nitrocefin, which changes from a yellowish color to a reddish color upon cleavage. In some embodiments, the β-lactamase comprises the amino acid sequence as set forth in SEQ ID NO: 30. In some embodiments, the β-lactamase is expressed from a nucleic acid comprising the nucleic acid sequence as set forth in SEQ ID NO: 31. It should be appreciated that any of the reporter peptides, described herein, are not meant to be limiting and that additional reporter peptides are within the scope of this disclosure.

In some embodiments, the reporter polypeptide is an antibiotic resistance protein. In some embodiments, the antibiotic resistance protein confers the ability of an engineered microorganism to grow in the presence of an antibiotic such as, but not limited to, chloramphenicol, kanamycin, gentamicin, rifampin, trimethoprim, or tetracycline. Such antibiotic resistance proteins are known in the art and are within the scope of this disclosure. The antibiotics, disclosed herein, represent both naturally occurring and synthetic drugs that target different processes within the microbial cell, including synthesis of RNA (rifampin), synthesis of proteins (chloramphenicol, kanamycin, gentamicin, and tetracycline), and synthesis of folate (trimethoprim).

In some embodiments, the output molecule is a nucleic acid. In some embodiments the output molecule is a ribonucleic acid (RNA). In some embodiments the RNA output molecule is part of a molecular reporting system, such as a reporting system described in Gredell J. A., "Protein and RNA engineering to customize microbial molecular reporting", *Biotechnol J.* 2012 April; 7(4):477-99; the contents of which are hereby incorporated by reference. Additional nucleic acid output molecules are within the scope of this disclosure.

Also provided herein are vectors comprising any of the engineered nucleic acids described herein. In some embodiments vectors comprise any of the hybrid receptors described herein. In some embodiments, vectors comprise any of the genes, nucleic acids, and/or promoters of any of the genetic circuits described herein. In some embodiments, vectors comprise any of the output molecules described herein. A "vector" is a nucleic acid (e.g., DNA) used as a vehicle to artificially carry genetic material (e.g., an engineered nucleic acid) into a cell where, for example, the nucleic acid can be replicated and/or expressed. In some embodiments, a vector is an episomal vector (see, e.g., Van Craenenbroeck K. et al. Eur. J. Biochem. 267, 5665, 2000, incorporated by reference herein). A non-limiting example of a vector is a plasmid. Plasmids are double-stranded generally circular DNA sequences that are capable of automatically replicating in a host cell. Plasmids typically contain an origin of replication that allows for semi-independent replication of the plasmid in the host and also the transgene insert. Plasmids may have more features, including, for example, a "multiple cloning site," which includes nucleotide overhangs for insertion of a nucleic acid insert, and multiple restriction enzyme consensus sites to either side of the insert. Another non-limiting example of a vector is a viral vector.

Applications

Aspects of the disclosure relate to methods for detecting and/or treating an infection of a *Vibrio* species. In some embodiments, the methods are for detecting and/or treating a *Vibrio cholerae* infection. In some embodiments, the methods of the present disclosure include administering to a subject having, or at risk of having, a *Vibrio cholerae* infection (i.e., cholera) any of the engineered microorganisms disclosed herein. The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject is not a normal subject or healthy volunteer.

In some embodiments, the engineered microorganisms are administered to the subject until one or more symptoms are reduced or cleared. In some embodiments, the engineered microorganisms are administered until the subject is free of the *Vibrio* species or until none of the *Vibrio* species is detected in the subject. In some embodiments, the engineered microorganisms are administered until the subject is free of *Vibrio cholerae* or until no *Vibrio cholerae* is detected in the subject. In some embodiments, the engineered microorganisms are administered to the subject until a reduction of at least 10%, at least 20%, at least 30%, at least 40%, at least 50%, at least 60%, at least 70%, at least 80%, at least 90%, at least 95%, at least 99%, or at least 100% of the *Vibrio cholerae* in a subject is achieved as compared to the level of *Vibrio cholerae* detected in the patient prior to administration of any of the engineered microorganisms, described herein.

In some embodiments, the engineered microorganisms of the present disclosure are administered to a subject to treat cholera. The terms "treatment," "treat," and "treating," refer to a clinical intervention aimed to reverse, alleviate, delay the onset of, or inhibit the progress of a disease or disorder (e.g., cholera), or one or more symptoms thereof. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a pathogen outbreak). Treatment may also be continued after symptoms have resolved, for example, to prevent or delay their recurrence.

Accordingly, also within the scope of the disclosure are pharmaceutical compositions comprising any of the engineered microorganisms disclosed herein. The term "pharmaceutical composition," as used herein, refers to a composition that can be administrated to a subject in the context of treatment of a disease or disorder (e.g., cholera). In some embodiments, a pharmaceutical composition comprises any of the engineered microorganisms described herein, and a pharmaceutically acceptable excipient.

In some embodiments the subject having or at risk of having a *Vibrio cholerae* infection is in an area of cholera outbreak. An "area of cholera outbreak," as used herein, refers to a location in proximity to one or more subjects having cholera or a *Vibrio cholerae* infection. In some embodiments, an area of cholera outbreak is an area of up to 0.1 miles, up to 0.5 miles, up to 1 mile, up to 2 miles, up to 5 miles, up to 10 miles, up to 20 miles, up to 40 miles, up to 80 miles, or up to 100 miles from one or more subjects having cholera or a *Vibrio cholerae* infection. In some embodiments, an area of cholera outbreak is an area that has at least 1, at least 2, at least 3, at least 4, at least 5, at least 10, at least 20, at least 50, at least 100, at least 200, at least 500, at least 1000, or at least 5000 subjects having cholera or a *Vibrio cholerae* infection.

In some embodiments, the methods described herein further include administering to a subject an antibiotic that is effective for killing the *Vibrio* species when the engineered bacterium expresses a detectable output molecule. In some embodiments, the methods described herein further include administering to a subject an antibiotic that is effective for killing *Vibrio cholerae* when the engineered bacterium expresses a detectable output molecule. In some embodiments, the antibiotic agent is, without limitation, tetracycline, doxycycline, erythromycin, ofloxacin, trimethoprim-sulfamethoxazole (TMP-SMX), furazolidone, sulfaguanidine, or ciprofloxacin. It should be appreciated, however, that additional antibiotic agents are also within the scope of this disclosure.

In some embodiments, the hybrid receptor and engineered circuits may be used to create engineered probiotic bacteria that inhabits the human intestine and serve to detect and eliminate a *Vibrio* species infection or *Vibrio cholerae* infection (i.e., cholera). *Vibrio cholerae* infections often occur in predictable seasonal and regional outbreaks, so vulnerable populations may be given the engineered bacteria containing the circuit as a prophylaxis. Alternatively, when a cholera outbreak occurs, the engineered bacteria may be given to family members and vulnerable people in the population to prevent any further spread of the disease.

In some embodiments, methods for detecting a *Vibrio* species pathogen are disclosed. In some embodiments, methods for detecting a *Vibrio cholerae* pathogen are disclosed. In some embodiments, methods for detecting a *Vibrio cholerae* pathogen in a subject may include administering any of the engineered microorganisms, described herein, to the subject and obtaining and/or isolating the engineered microorganisms from the subject. For example, from a biological sample (e.g., a stool sample) of the subject. The level of an output molecule expressed in the engineered microorganisms may be detected or measured to determine whether the subject has *Vibrio cholerae*. Alternatively, the engineered microorganisms may be used in a cell-free diagnostic system to detect the presence of CAI-1 produced by *Vibrio cholerae*. For example any of the engineered microorganisms of the present disclosure may be contacted with a sample (e.g., a stool sample or a blood sample) in the presence or absence of cells to determine whether the sample contains *Vibrio cholerae*.

In some embodiments, methods for detecting a cholera infection in a subject comprise obtaining a biological sample from a subject. As used herein, a "biological sample" may be used generally to refer to any biological material which may be obtained from a subject. For example, the biological sample may be whole blood, plasma, tissue (e.g., normal tissue or tumor tissue), urine, feces, or cells. The biological sample typically is a fluid sample. Solid tissues may be made into fluid samples using routine methods in the art.

Some aspects of the disclosure provide methods for detecting a cholera infection in a subject using an in vitro detection assay. In some embodiments, the in vitro detection assay is a colorimetric assay. As used herein, a "colorimetric assay" refers to an assay that includes one or more reagents (e.g., colorimetric substrates) that undergo a measurable color change in the presence of an analyte, such as an output molecule that cleaves a colorimetric substrate to produce a color change. As used herein, a "colorimetric substrate" refers to a molecule that undergoes a measurable color change in the presence of an analyte, such as an enzyme that cleaves the colorimetric substrate. For example, a colorimetric assay may include testing for the presence of β-lactamase by contacting the β-lactamase with a nitrocefin substrate (e.g., a colorimetric substrate), which is cleaved by β-lactamase to produce a reddish colored product. In some embodiments, the colorimetric substrate is nitrocefin, X-gal, or BCIP, which may be cleaved by β-lactamase, β-galactosidase, and alkaline phosphatase, respectively. Colorimetric assays and substrates are widely used in biochemistry to test for the presence of enzymes, compounds, antibodies, hormones in addition to other analytes. Accordingly, a skilled artisan would recognize additional colorimetric assays and substrates that may be used in accordance with the disclosure and those colorimetric assays and substrates provided herein are not meant to be limiting.

In some embodiments, the methods for detecting a cholera infection using an in vitro colorimetric assay include detecting a color change. Detecting a color change in an in vitro colorimetric assay can be done using any suitable method. For example, in some embodiments, detecting a color change is done visually, e.g., by an person that observes a color change in a colorimetric assay. In some embodiments, detecting a color change is done using spectrophotometry, which is a method commonly used to measure (e.g., quantitatively) the reflection or transmission properties of a sample (e.g. a fluid sample containing a colorimetric substrate), which may be used to determine an amount of a substance, for example a colorimetric substrate in a sample. In some embodiments, spectrophotometry is used to quantify a level of a colorimetric substrate that has been cleaved, for example, in a colorimetric assay.

It should be appreciated that a color change observed in a colorimetric assay may be used to determine whether or not a subject has a cholera infection. In some embodiments, a subject is determined to have a cholera infection if a color change is observed when a colorimetric assay is performed using a biological sample from the subject. In some embodiments, a color change of a colorimetric assay using a biological sample from a subject is compared to a color change of a colorimetric assay using a control sample, for example a positive or negative control. In some embodiments, the negative control sample is a biological sample from a subject that does not have a cholera infection. In some embodiments, the negative control sample is a sample that does not comprise a *V. cholerae* pathogen. In some embodiments, the negative control sample is a sample that does not comprise CAI-1. In some embodiments, the negative control sample is a sample that does not comprise ATc. In some embodiments, the positive control sample is a biological sample from a subject that has a cholera infection. In some embodiments, the positive control sample is a sample that comprises a *V. cholerae* pathogen. In some embodiments, the positive control sample is a sample that comprises CAI-1. In some embodiments, the positive control sample is a sample that comprises ATc.

In some embodiments, a subject is determined to have a cholera infection if a color change observed in a colorimetric assay using a biological sample from the subject is greater than a color change observed in a colorimetric assay using a control sample (e.g., a negative control sample). In some embodiments, a subject is determined to have a cholera infection if a color change observed in a colorimetric assay using a biological sample from the subject is at least 5%, 10%, 15%, 20%, 25%, 30%, 35%, 40%, 45%, 50%, 55%, 60%, 65%, 70%, 75%, 80%, 85%, 90%, 95%, or 100% greater than a color change observed in a colorimetric assay using a control sample (e.g., a negative control sample). It should be appreciated, however, that determining whether a subject has a cholera infection using any of the methods provided herein may depend on a number of factors including, but not limited to, the sensitivity of the assay, the severity of the infection, the particular colorimetric assay used, and/or the type of biological sample obtained from the subject.

EXAMPLES

Example 1: Engineering of *Lactococcus lactis* to Detect and Kill *Vibrio cholerae*

The purpose of this technology is to engineer the two-component system of the probiotic bacteria *Lactococcus lactis* to detect and kill the cholera pathogen *Vibrio cholerae*. *L. lactis* is a member of the lactic-acid bacteria family and labeled "generally recognized as safe (GRAS)" by the FDA. Because it can reside in the human intestine with no harm to the body, *L. lactis* can be an ideal candidate for intestinal pathogen sensing and killing. Cholera is an infectious disease that can cause severe diarrhea. There are three to five million cholera cases every year, resulting in 1 00,000-120,000 deaths, mostly in developing countries[1]. The engineered *L. lactis* will promise a safe, efficient and low-cost treatment for the serious infectious disease cholera.

Figure 2:
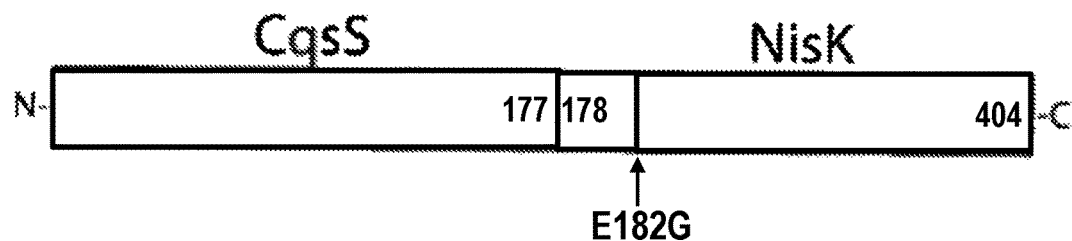
FIG. 2 is a schematic of the primary amino acid sequence of the hybrid CqsS-NisK receptor. The N-terminal region of CqsS (left, amino acids 1-177 of native CqsS) is fused to the C-terminal region of NisK (right, amino acids 221-447 of native NisK) to create the hybrid receptor. The hybrid receptor contains a mutation in the NisK region (E182G), which increases its responsiveness to CAI-1.

A hybrid cell surface receptor that allows *L. lactis* to detect the *Vibrio cholerae* quorum-sensing molecule CAI-1 has been developed[2]. To enable CAI-1 detection, the *Vibrio cholerae* CqsS receptor which has evolved to specifically recognize CAI-1 was used. CqsS is a two component histidine kinase receptor that converts small molecule binding into a phosphorylation signal that is passed from its histidine kinase domain to its aspartate receiver partner, resulting in altered transcription. To incorporate the CqsS receptor into *L. lactis*, the receptor region of CqsS was fused to the signal transduction region of NisK, a well characterized histidine kinase receptor in *L. lactis*[3] (FIG. 2). When this hybrid receptor binds to CAI-1 molecules secreted by *Vibrio cholerae*, it deactivates phosphorylation signaling though the NisK histidine kinase domain, resulting in dephosphorylation of NisR and reduced transcription from the nisA promoter in *L. lactis*. This hybrid receptor also contains a single amino acid change in the NisK region of the protein (E182G) which is important for signal transduction. The full protein sequence of the hybrid receptor (SEQ ID NO: 1) is listed below.

Figure 5:
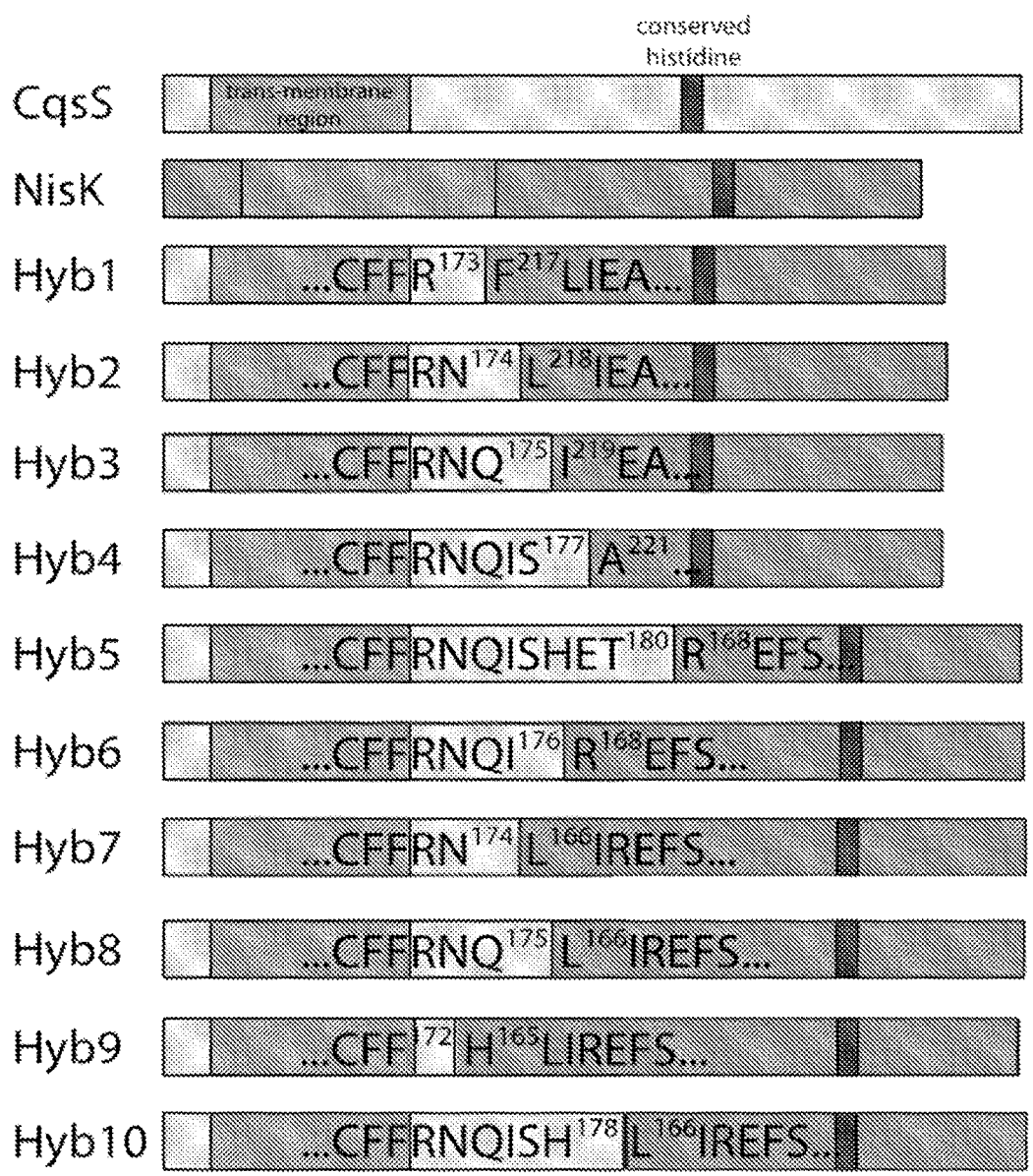
FIG. 5 shows 10 different hybrid receptor fusion strategies. Amino acid sequences at the junctions are shown in detail. Amino acid numbers at each junction indicate their locations in the original CqsS and NisK sequences respectively. The sequences are as follows: Hyb1 (SEQ ID NOs: 32 and 33), Hyb2 (SEQ ID NOs: 34 and 35), Hyb3 (SEQ ID NO: 36), Hyb4 (SEQ ID NO: 37), Hyb5 (SEQ ID NOs: 38 and 39), Hyb6 (SEQ ID NOs: 40 and 39), Hyb1 (SEQ ID NOs: 34 and 41), Hyb8 (SEQ ID NOs: 36 and 41), Hyb9 (SEQ ID NO: 42), and Hyb10 (SEQ ID NOs: 43 and 41)

To make a functional CqsS-NisK hybrid, several CqsS-NisK fusions were made using homology in the cytoplasmic region following the last predicted transmembrane region in CqsS and NisK to find an appropriate fusion point between the two proteins. Ten hybrid designs, labeled Hyb1-Hyb10, were chosen for further study (FIG. 5). It has been shown that the protein expression level of NisK and NisR is important for their activity, as high NisR expression causes NisK-independent activation of gene expression, so a randomized RBS library for each of the 10 hybrid CqsS-NisK gene fusions was generated to test a range of expression levels for each hybrid. Approximately 100 RBS library members of each hybrid CqsS-NisK fusion were tested for CAI-1 dependent expression of mCherry which was placed under control of the nisA promoter regulated by NisR.

The strongest CAI-1 dependent phenotype was seen in a single clone from the Hyb4 library, and full sequence analysis of this clone showed that it contained an unexpected point mutation in the codon coding for amino acid 182, changing it from a glutamate to a glycine (E182G).

Figure 6:
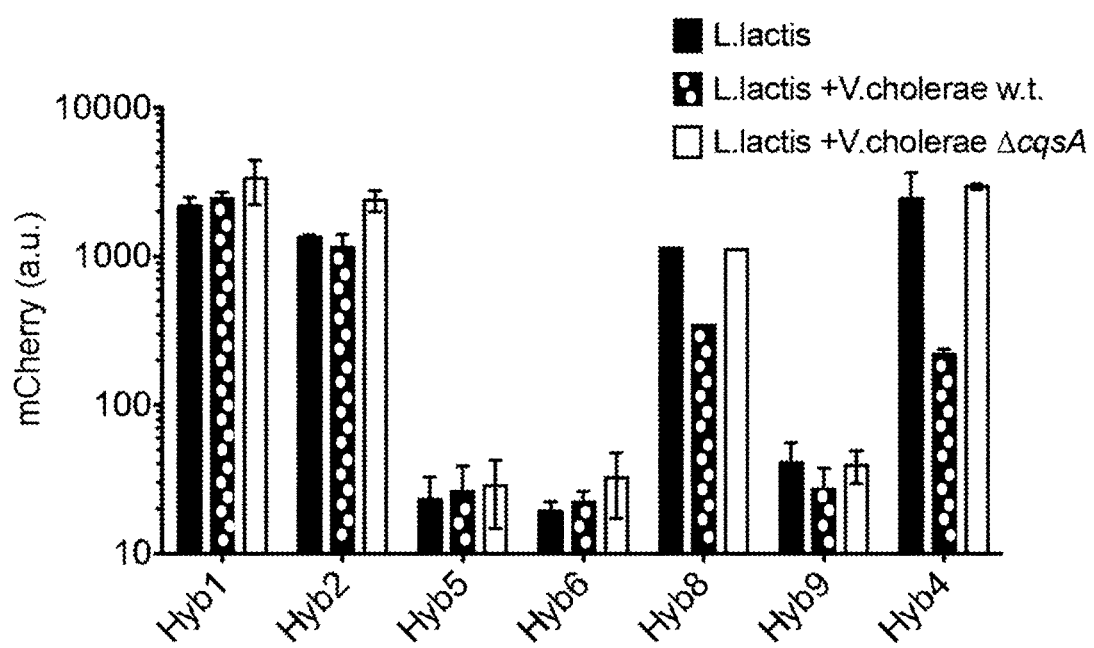
FIG. 6 shows the activity of different hybrid receptor variants, all with the specific E182G mutation, in CAI-1 induction assays in the presence of *Vibrio cholerae* wild-type, *Vibrio cholerae* ΔcqsA, or *E. coli*. In each group of three bars, the left bar represents data obtained with *L. lactis*, the middle bar represents data obtained with *L. lactis*+*V. cholerae* w.t., and the right bar represents data obtained with *L. lactis*+*V. cholerae* ΔcqsA.
Figure 7:
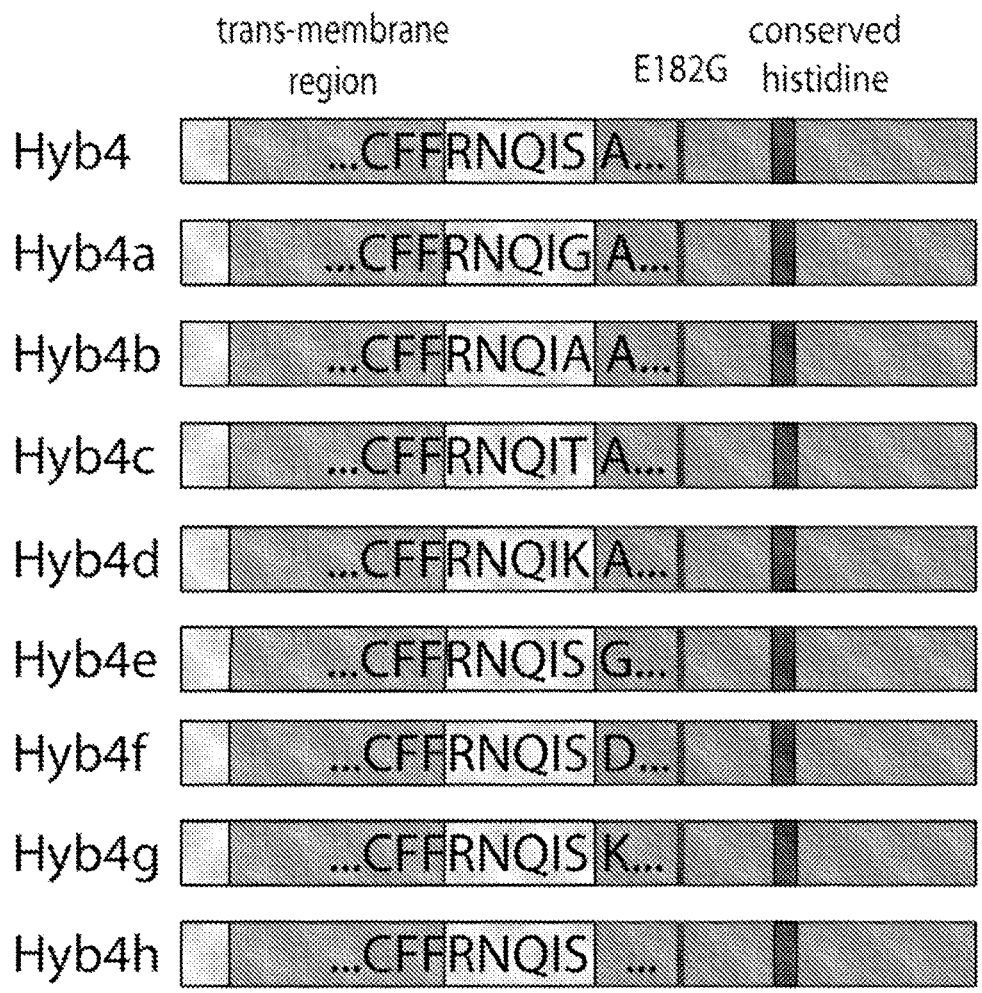
FIG. 7 shows a schematic of the amino acid mutation variants of the hybrid receptors at the Hyb4 junction. The sequences, from top to bottom, correspond to SEQ ID NOs: 44-51, and 37.

To determine if this single amino acid change was required for CAI-1 dependent repression of mCherry expression, the point mutation in the Hyb4 clone was reverted to glutamate and it was found that the clone almost completely lost the ability to respond to CAI-1 expression. In addition, the glutamate to glycine point mutation was cloned into the other hybrids to test if this point mutation would allow the other hybrids to respond to CAI-1. As shown in FIG. 6, Hyb8 and Hyb9 showed some CAI-1 response, suggesting that the point mutation provides some benefit to these hybrids, but Hyb4 showed the strongest CAI-1 dependent response. Data for Hyb3, Hyb1 and Hyb10 are not shown because of the instability of their encoding genes during cloning.

To enable transcriptional activation of an output module, a transcription invertor was integrated into the circuit so that CAI-1 detection by the hybrid receptor results in increased target gene expression (FIG. 3B). In this circuit design, the TetR repressor was placed under control of the nisA promoter and then placed the output module under control of the TetR-repressible xyltet2 promoter which is derived from the *Bacillus subtilis* xylA promoter[4] and contains tetO operator sites.

Figure 8:
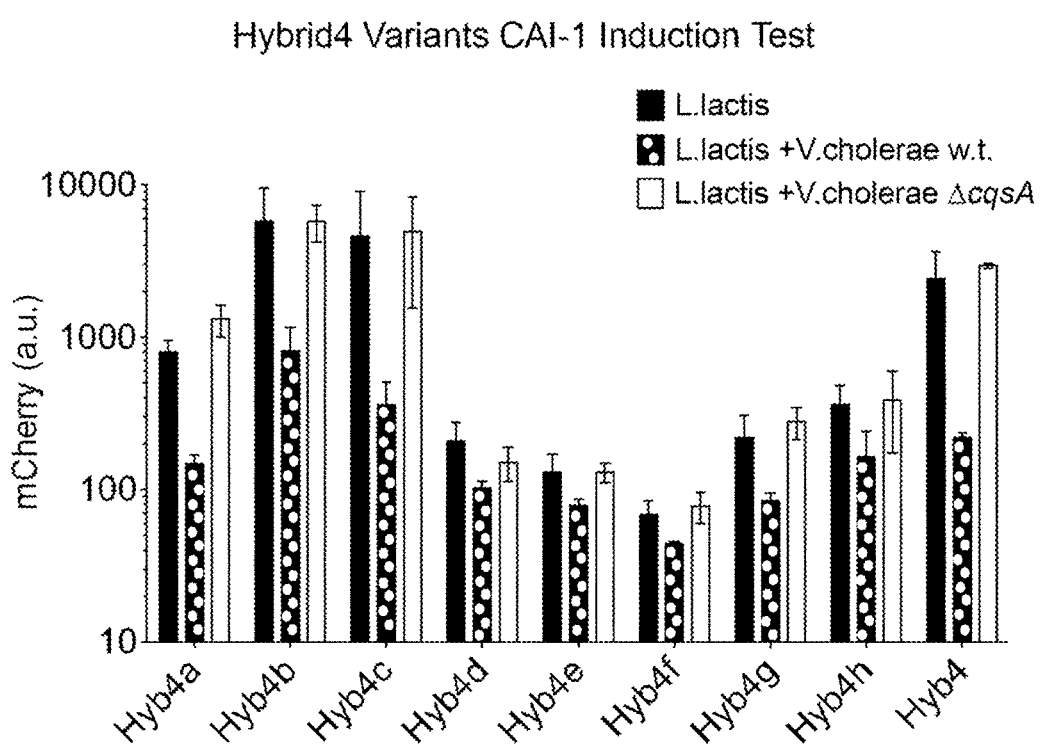
FIG. 8 shows the CAI-1 induction activity of different Hyb4 variants in the presence of *Vibrio cholerae* wild-type, *Vibrio cholerae* ΔcqsA, or *E. coli*. In each group of three bars, the left bar represents data obtained with *L. lactis*, the middle bar represents data obtained with *L. lactis*+*V. cholerae* w.t., and the right bar represents data obtained with *L. lactis*+*V. cholerae* ΔcqsA.

To further optimize the functionality in Hyb4 containing the E182G mutation, targeted point mutations were made in the amino acids that form the junction between CqsS and NisK to look for Hyb4 variants with an increased response to CAI-1 (FIG. 3A). As shown in FIG. 8, Hyb4 variants with the amino acid substitutions tested in alanine 178 (A178) retained some ability to respond to CAI-1, but none showed a stronger response than the original Hyb4. Amino acid substitutions in S177 showed differential responses to CAI-1, with S177A and S177T showing similar response to Hyb4 and S177K showing markedly weaker response. This is perhaps not surprising since the introduction of a large side chain with a positive charge (S177K) is more likely to disrupt the structure than relatively minor amino acid changes such as S177T. Deletion of A176 or S177 had a strong detrimental effect on Hyb4 to respond to CAI-1.

Figure 4:
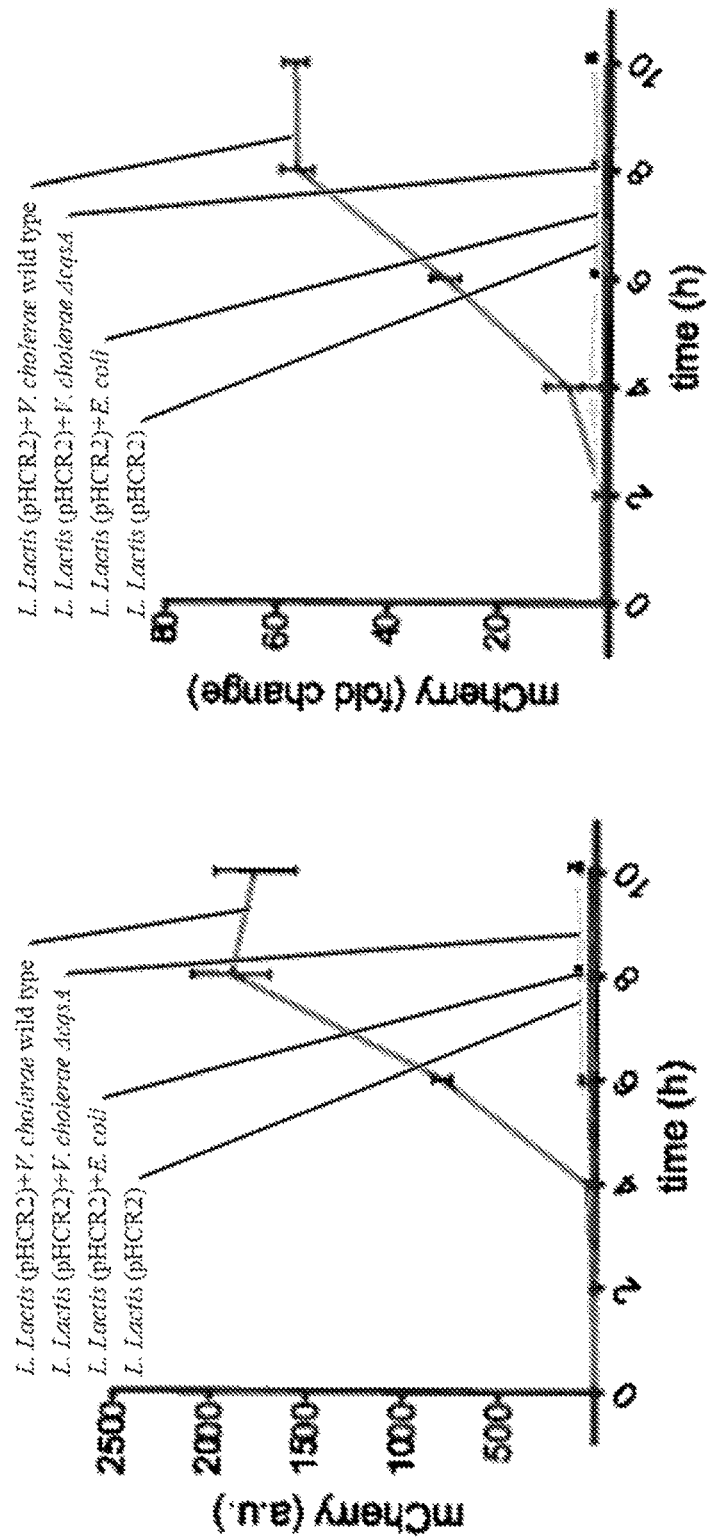
FIG. 4 shows the time response of the output gene expression in absolute measurements (left) and fold change (right). *L. lactis* contains pHCR2, which is the signal inverter circuit containing mCherry as the output module, and is grown in co-culture with either *E. coli* or *Vibrio cholerae* as indicated. *Vibrio cholerae* ΔcqsA is a control strain that is unable to synthesize CAI-I and should therefore not activate the hybrid receptor. All data were collected by flow cytometry and represent the mean±S.D. of three biological replicates.

As shown in FIG. 4, inclusion of this signal inverter circuit in *L. lactis* allows the bacteria to specifically detect *Vibrio cholerae*, producing a nearly 60-fold activation of the target gene expression in the presence of CAI-1 (FIG. 4). In this case, the output module is mCherry, but in other iterations the output module may be antimicrobial agents such as antimicrobial peptides (AMPs) or bacteriophage that can target *Vibrio cholerae* for killing. Other output module iterations include protein fusions of phage tail proteins that specifically bind *Vibrio cholerae* and AMPs that will kill or inhibit the bacteria. Colorimetric output modules such as LacZ (e.g., β-galactosidase) and β-lactamase may also be used to enable visual detection of circuit activation with the naked eye or by instrumentation.

In the absence of CAI-1, Hyb4 causes strong phosphorylation of NisR, resulting in strong mCherry expression from the nisA promoter. In the presence of CAI-1, reduced phosphorylation of NisR causes reduced mCherry expression. This is the same mode of action of CqsS, which autophosphorylates in the absence of CAI-1, and it is the opposite of what is normally seen for NisK where phosphorylation is low in the absence of nisin and is induced upon nisin binding. It appears that in Hyb4, CqsS receptor domain causes autophosphorylation of NisK as it does in its native CqsS context, and CAI-1 binding causes a conformational change that reduces or blocks phosphorylation.

This is a unique hybrid two component system. The creation of a hybrid histidine kinase receptor using a receptor domain from a histidine kinase receptor that autophosphorylates in the absence of the small molecule and a histidine kinase domain from a histidine kinase receptor that autophosphorylates in the presence of the small molecule is novel.

In other iterations, the hybrid receptor may be placed in other genetic constructs or in other bacteria such as Lactobacilli species including *Lactobacillus acidophilus* and *Lactobacillus gasseri*. The CqsS-NisK construct is likely to work in other bacteria where NisRK has been shown to function, including lactic acid bacteria (LAB) such as *Leuconostoc lactis, Lactobacillus brevis, Lactobacillus plantarum, Lactobacillus casei, Lactobacillus gasseri, Lactobacillus helveticus, Streptococcus pyogenes, Streptococcus agalactiae, Streptococcus pneumoniae*, and *Streptococcus zooepidemicus*. NisRK is also functional in other bacteria including *Enterococcus faecalis, Staphylococcus simulans* and *Bacillus subtilis*, suggesting that our CqsS-NisK fusion protein would also be functional.

Other histidine kinase proteins could be used in place of NisK to couple the CqsS CAI-1 receptor domain with phosphorylation dependent signaling, including other well studied two component systems such as the SpaRK two-component system in *Bacillus subtilis*. Two component systems are found in nearly all sequenced bacteria and contain well defined histidine kinase domains that may be used to identify an appropriate site to fuse the receptor domain from CqsS to the histidine kinase domain to enable CAI-1-dependent phosphorylation or dephosphorylation.

Figure 9:
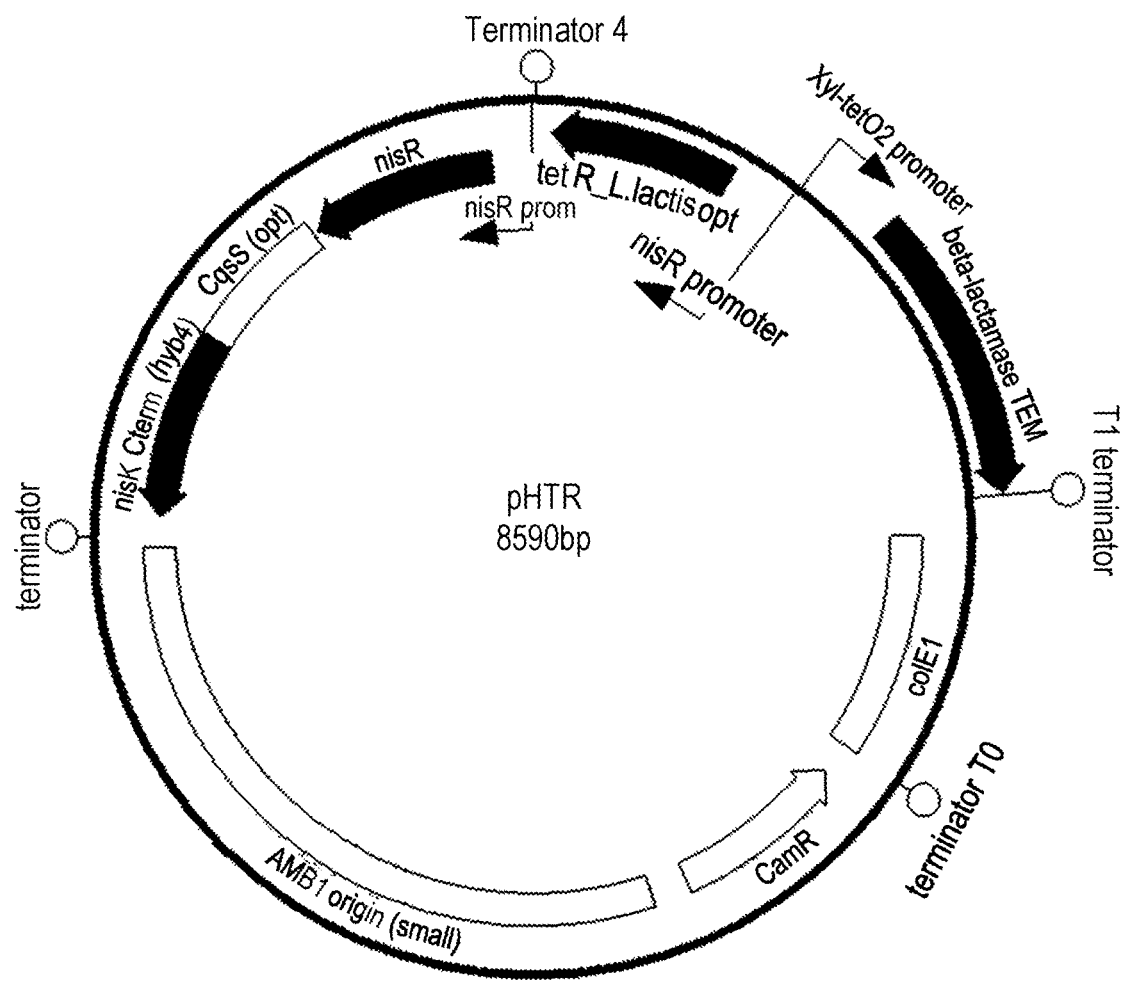
FIG. 9 is a schematic representation of pHTR plasmid map.

Example 2: Engineering of *Lactococcus lactis* to Detect *Vibrio cholerae* Using a Colorimetric Based Assay The present example describes an engineered *Lactococcus lactis* (*L. lactis*) microorganism that can be used to detect (e.g., in vitro) a *V. choerae* microorganism in a colorimetric assay. *L. lactis* was engineered to produce ß-lactamase in response to detecting CAI-1 secreted by *V. cholerae*, which turns a yellow substrate (nitrocefin) red when *V. cholerae* is detected. β-lactamase is a robust enzyme with a high catalytic efficacy and a small size that makes it easy to diffuse. Wild-type (w.t.) *L. lactis* were transformed with pHTR plasmid, a schematic of which is shown in FIG. 9. The pHTR plasmid is a derivation of the pHCR2 plasmid, with the mCherry gene replaced by β-lactamase gene. *L. lactis* transformed with pHTR express ß-lactamase in response to detecting CAI-1 secreted by *V. cholerae*. The pHTR construct has β-lactamase repressed by TetR, where anhydrotetracycline (ATc) is an inducer that can be used to release TetR from binding the xyltet promoter and thus activate the expression of the β-lactamase gene. Accordingly, adding ATc to *L. lactis* harboring the pHTR plasmid can be used as a positive control for β-lactamase expression, for example in the absence of CAI-1 secreted by *V. cholerae*.

Figure 10A:
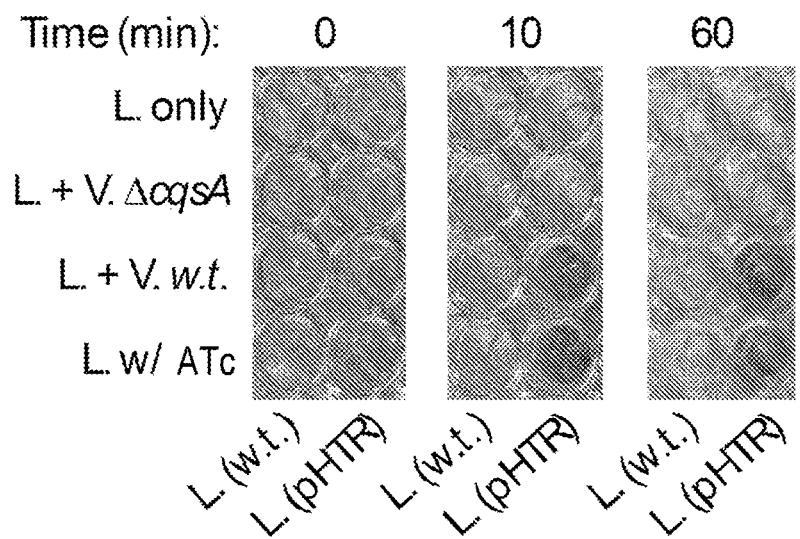
FIGS. 10A-10B are exemplary data demonstrating that *L. lactis* detects wild-type *V. cholerae* via CAI-1 molecules.
Figure 10B:
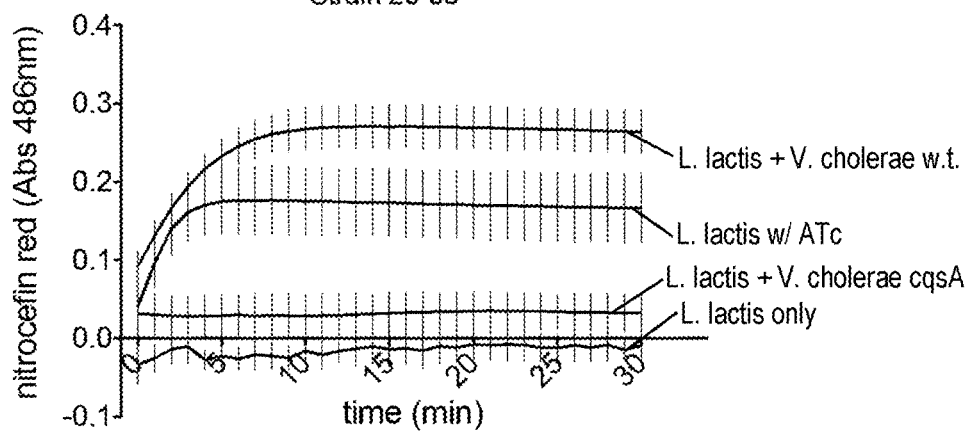

To test the diagnostic functionality of *L. lactis* (pHTR) to detect *V. cholerae*, *L. lactis* transfected with pHTR, "L. (pHTR)", were co-cultured with wild-type *V. cholerae*, "V. w.t.", in media. After 8 hours of co-culture, L.(pHTR) cells were fully induced to produce and secrete abundant ß-lactamase. The whole culture was sampled to test with nitrocefin substrate (0.1 µM final concentration), which changes color from yellow to red in the presence of β-lactamase. Within 10 minutes, the cultures that have CAI-1 present turned red and were distinguishable from the yellow color of CAI-1 negative cultures. See third row from the top of FIG. 10A, showing the color change over the course of 60 minutes, and the spectrophotometer readings in FIG. 10B, which represent the color change over the course of 30 minutes. Controls where wild-type *L. lactis* "L. (w.t.)" or *L. lactis* expressing pHTR "L.(pHTR)" are cultured alone (L. only), or in the presence of *V. cholerae* that do not express CAI-1 (L-FV.ΔcqsA) did not change the yellow color of the nitrocefin substrate to red. See top two rows of FIG. 10A, and the spectrophotometer readings in FIG. 10B. As a positive control, L.(w.t.) and L.(pHTR) were cultured in the presence of anhydrotetracycline (L. w/ATc). See bottom row of FIG. 10A, and the spectrophotometer readings in FIG. 10B. The L.(pHTR) cells, but not the L.(w.t.) cells were capable of changing the nitrocefin substrate in the media from yellow to red in the presence of ATc.

Figure 11:
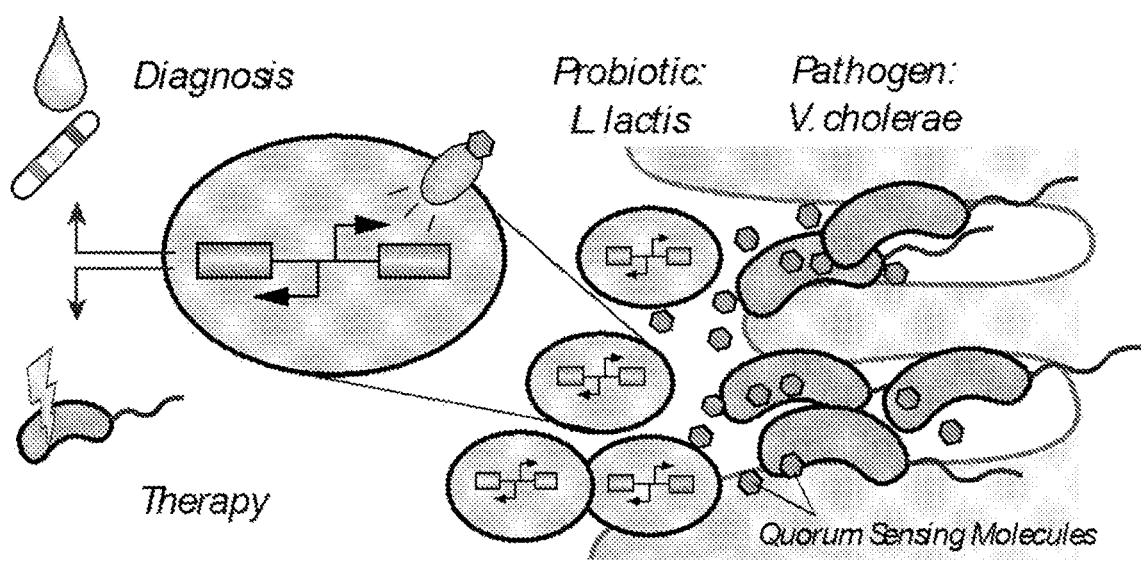
FIG. 11 is an exemplary schematic showing an engineered probiotic bacteria (e.g., *Lactococcus lactis*) are able to detect the presence of a pathogenic bacteria (e.g., *Vibrio cholerae*) and initiate both diagnostic and therapeutic functions.

Accordingly, this example demonstrates that engineered microorganisms provided herein, for example *L. lactis*, can be used to detect the presence of other microorganisms, such as pathogenic *V. cholerae*, for example using an in vitro colorimetric assay. A schematic representation demonstrating how engineered probiotic bacteria, e.g., *Lactococcus lactis* are able to detect the presence of pathogenic bacteria, e.g., *Vibrio cholerae* and initiate diagnostic and/or therapeutic functions is shown in FIG. 11.

```
Hybrid Receptor Protein Sequence
                                            (SEQ ID NO: 1)
MIVSMDVIKRVYQYAEPNLSLVGWMGMLGFPAYYFIWEYWFPQSYENLGL

RCAAAVLFGGLVFRDSMPKKWQRYMPGYFLFTIGFCLPFFFAFMMLMNDW

STIWAMSFMASIFLHILLVHDTRVMALQALFSVLVAYLAVYGLTDFHPTT

LIEWQYIPIFLFTYVFGNLCFFRNQISAERHGKHDLSFQVAALSHDVKTP

LTVLKGNIELLEMTEVNEQQADFIESMKNSLTVFDKYFNTMISYTKLLND

ENDYKAIISLEDFLIDLSVELEELSTTYQVDYQLVKKTDLTTFYGNTLAL

SRALINIFVNACQYAKEGEKIVSLSIYDDEKYLYFEIWNNGHPFSEQAKK

NAGKLFFTEDTGRSGKHYGIGLSFAQGVALKHQGNLILSNPQKGGAEVIL

KIKK

Amino Acids 1-177 of CqsS and of a Hybrid Receptor
                                            (SEQ ID NO: 2)
MIVSMDVIKRVYQYAEPNLSLVGWMGMLGFPAYYFIWEYWFPQSYENLGL

RCAAAVLFGGLVFRDSMPKKWQRYMPGYFLFTIGFCLPFFFAFMMLMNDW

STIWAMSFMASIFLHILLVHDTRVMALQALFSVLVAYLAVYGLTDFHPTT

LIEWQYIPIFLFTYVFGNLCFFRNQIS

Amino Acids 178-404 of a Hybrid Receptor
                                            (SEQ ID NO: 3)
AERHGKHDLSFQVAALSHDVKTPLTVLKGNIELLEMTEVNEQQADFIESM

KNSLTVFDKYFNTMISYTKLLNDENDYKAIISLEDFLIDLSVELEELSTT

YQVDYQLVKKTDLTTFYGNTLALSRALINIFVNACQYAKEGEKIVSLSIY

DDEKYLYFEIWNNGHPFSEQAKKNAGKLFFTEDTGRSGKHYGIGLSFAQG

VALKHQGNLILSNPQKGGAEVILKIKK

CqsS of Vibrio cholerae (gi|669353531|gb|
KFD83389.1|CAI-1 autoinducer sensor kinase/
phosphatase)
                                            (SEQ ID NO: 4)
MIVSMDVIKRVYQYAEPNLSLVGWMGMLGFPAYYFIWEYWFPQSYENLGL

RCAAAVLFGGLVFRDSMPKKWQRYMPGYFLFTIGFCLPFFFAFMMLMNDW

STIWAMSFMASIFLHILLVHDTRVMALQALFSVLVAYLAVYGLTDFHPTT

LIEWQYIPIFLFTYVFGNLCFFRNQISHETKVSIAKTFGAGIAHEMRNPL

SALKTSIDVVRTMIPKPQTAAHTDYSLDAQELDLLHQILNEADDVIYSGN

NAIDLLLTSIDENRVSPASFKKHSVVDVIEKAVKTFPYKNAADQHSVELE

VHQPFDFFGSDTLLTYALFNLLKNAFYYQKEHFSVRISIEQTIEYNLIRV

RDNGVGIAPEMLEDIFRDFYTFGKNGSYGLGLPFCRKVMTAFGGTIRCAS

QQGQWTEFVLSFPRYDSDTVNEIKTELLKTKSLIYIGSNQAIVRELNQLA

VEDEFGFTAISAQQAVRRQDYEFEFDLILLDLDDATAQGELLPKLEGTLS

FAEGCIGYVYDPGKTYAVNINRYLRIQPISIHSILRKPRKIIERLLFEQE

SLSMNRNVIPLQKSRHERRILVVDDNQSIRTFTAILLEQQGYEVVQANDG

SEVLKHMESQNIDLVLMDIEMPNVGGLEATRLIRDSEHEYKNIPIIGYTG

DNSPKTLALVQTSGMNDFIVKPADRDVLLNKVAAWV

NisK of Lactococcus lactis (gi|504383310|ref|
WP_014570412.1|nisin biosynthesis sensor protein)
                                            (SEQ ID NO: 5)
MGKKYSMRRRIWQAVIEIIIGTCLLILLLLGLTFFLRQIGQISGSETIRL

SLDSDNLTISDIERDMKHYPYDYIIFDNDTSKILGGHYVKSDVPSFVASK

QSSHNITEGEITYTYSSNKHFSVVLRQNSMPEFTNHTLRSISYNQFTYLF

FFLGEIILIIFSVYHLIREFSKNFQAVQKIALKMGEITTFPEQEESKIIE

FDQVLNNLYSKSKELAFLIEAERHEKHDLSFQVAALSHDVKTPLTVLKGN

IELLEMTEVNEQQADFIESMKNSLTVFDKYFNTMISYTKLLNDENDYKAT

ISLEDFLIDLSVELEELSTTYQVDYQLVKKTDLTTFYGNTLALSRALINI

FVNACQYAKEGEKIVSLSIYDDEKYLYFEIWNNGHPFSEQAKKNAGKLFF

TEDTGRSGKHYGIGLSFAQGVALKHQGNLILSNPQKGGAEVILKIKK

Hyb4a
                                            (SEQ ID NO: 6)
MIVSMDVIKRVYQYAEPNLSLVGWMGMLGFPAYYFIWEYWFPQSYENLGL

RCAAAVLFGGLVFRDSMPKKWQRYMPGYFLFTIGFCLPFFFAFMMLMNDW
```

STIWAMSFMASIFLHILLVHDTRVMALQALFSVLVAYLAVYGLTDFHPTT

LIEWQYIPIFLFTYVFGNLCFFRNQIGAERHGKHDLSFQVAALSHDVKTP

LTVLKGNIELLEMTEVNEQQADFIESMKNSLTVFDKYFNTMISYTKLLND

ENDYKAIISLEDFLIDLSVELEELSTTYQVDYQLVKKTDLTTFYGNTLAL

SRALINIFVNACQYAKEGEKIVSLSIYDDEKYLYFEIWNNGHPFSEQAKK

NAGKLFFTEDTGRSGKHYGIGLSFAQGVALKHQGNLILSNPQKGGAEVIL

KIKK

Hyb4b (SEQ ID NO: 7)
MIVSMDVIKRVYQYAEPNLSLVGWMGMLGFPAYYFIWEYWFPQSYENLGL

RCAAAVLFGGLVFRDSMPKKWQRYMPGYFLFTIGFCLPFFFAFMMLMNDW

STIWAMSFMASIFLHILLVHDTRVMALQALFSVLVAYLAVYGLTDFHPTT

LIEWQYIPIFLFTYVFGNLCFFERNQIAAERHGKHDLSFQVAALSHDVKTP

LTVLKGNIELLEMTEVNEQQADFIESMKNSLTVFDKYFNTMISYTKLLND

ENDYKAIISLEDFLIDLSVELEELSTTYQVDYQLVKKTDLTTFYGNTLAL

SRALINIFVNACQYAKEGEKIVSLSIYDDEKYLYFEIWNNGHPFSEQAKK

NAGKLFFTEDTGRSGKHYGIGLSFAQGVALKHQGNLILSNPQKGGAEVIL

KIKK

Hyb4c (SEQ ID NO: 8)
MIVSMDVIKRVYQYAEPNLSLVGWMGMLGFPAYYFIWEYWFPQSYENLGL

RCAAAVLFGGLVFRDSMPKKWQRYMPGYFLFTIGFCLPFFFAFMMLMNDW

STIWAMSFMASIFLHILLVHDTRVMALQALFSVLVAYLAVYGLTDFHPTT

LIEWQYIPIFLFTYVFGNLCFFRNQITAERHGKHDLSFQVAALSHDVKTP

LTVLKGNIELLEMTEVNEQQADFIESMKNSLTVFDKYFNTMISYTKLLND

ENDYKAIISLEDFLIDLSVELEELSTTYQVDYQLVKKTDLTTFYGNTLAL

SRALINIFVNACQYAKEGEKIVSLSIYDDEKYLYFEIWNNGHPFSEQAKK

NAGKLFFTEDTGRSGKHYGIGLSFAQGVALKHQGNLILSNPQKGGAEVIL

KIKK

Hyb4d (SEQ ID NO: 9)
MIVSMDVIKRVYQYAEPNLSLVGWMGMLGFPAYYFIWEYWFPQSYENLGL

RCAAAVLFGGLVFRDSMPKKWQRYMPGYFLFTIGFCLPFFFAFMMLMNDW

STIWAMSFMASIFLHILLVHDTRVMALQALFSVLVAYLAVYGLTDFHPTT

LIEWQYIPIFLFTYVFGNLCFFRNQIKAERHGKHDLSFQVAALSHDVKTP

LTVLKGNIELLEMTEVNEQQADFIESMKNSLTVFDKYFNTMISYTKLLND

ENDYKAIISLEDFLIDLSVELEELSTTYQVDYQLVKKTDLTTFYGNTLAL

SRALINIFVNACQYAKEGEKIVSLSIYDDEKYLYFEIWNNGHPFSEQAKK

NAGKLFFTEDTGRSGKHYGIGLSFAQGVALKHQGNLILSNPQKGGAEVIL

KIKK

Hyb4e (SEQ ID NO: 10)
MIVSMDVIKRVYQYAEPNLSLVGWMGMLGFPAYYFIWEYWFPQSYENLGL

RCAAAVLFGGLVFRDSMPKKWQRYMPGYFLFTIGFCLPFFFAFMMLMNDW

STIWAMSFMASIFLHILLVHDTRVMALQALFSVLVAYLAVYGLTDFHPTT

LIEWQYIPIFLFTYVFGNLCFFRNQISGERHGKHDLSFQVAALSHDVKTP

LTVLKGNIELLEMTEVNEQQADFIESMKNSLTVFDKYFNTMISYTKLLND

ENDYKAIISLEDFLIDLSVELEELSTTYQVDYQLVKKTDLTTFYGNTLAL

SRALINIFVNACQYAKEGEKIVSLSIYDDEKYLYFEIWNNGHPFSEQAKK

NAGKLFFTEDTGRSGKHYGIGLSFAQGVALKHQGNLILSNPQKGGAEVIL

KIKK

Hyb4f (SEQ ID NO: 11)
MIVSMDVIKRVYQYAEPNLSLVGWMGMLGFPAYYFIWEYWFPQSYENLGL

RCAAAVLFGGLVFRDSMPKKWQRYMPGYFLFTIGFCLPFFFAFMMLMNDW

STIWAMSFMASIFLHILLVHDTRVMALQALFSVLVAYLAVYGLTDFHPTT

LIEWQYIPIFLFTYVFGNLCFFRNQISDERHGKHDLSFQVAALSHDVKTP

LTVLKGNIELLEMTEVNEQQADFIESMKNSLTVFDKYFNTMISYTKLLND

ENDYKAIISLEDFLIDLSVELEELSTTYQVDYQLVKKTDLTTFYGNTLAL

SRALINIFVNACQYAKEGEKIVSLSIYDDEKYLYFEIWNNGHPFSEQAKK

NAGKLEFTEDTGRSGKHYGIGLSFAQGVALKHQGNLILSNPQKGGAEVIL

KIKK

Hyb4g (SEQ ID NO: 12)
MIVSMDVIKRVYQYAEPNLSLVGWMGMLGFPAYYFIWEYWFPQSYENLGL

RCAAAVLEGGLVERDSMPKKWQRYMPGYFLFTIGFCLPFFFAFMMLMNDW

STIWAMSFMASIFLHILLVHDTRVMALQALFSVLVAYLAVYGLTDFHPTT

LIEWQYIPIFLFTYVFGNLCFERNQISKERHGKHDLSFQVAALSHDVKTP

LTVLKGNIELLEMTEVNEQQADFIESMKNSLTVFDKYFNTMISYTKLLND

ENDYKAIISLEDFLIDLSVELEELSTTYQVDYQLVKKTDLTTFYGNTLAL

SRALINIFVNACQYAKEGEKIVSLSIYDDEKYLYFEIWNNGHPFSEQAKK

NAGKLEFTEDTGRSGKHYGIGLSFAQGVALKHQGNLILSNPQKGGAEVIL

KIKK

Hyb4h (SEQ ID NO: 13)
MIVSMDVIKRVYQYAEPNLSLVGWMGMLGFPAYYFIWEYWFPQSYENLGL

RCAAAVLFGGLVFRDSMPKKWQRYMPGYFLFTIGFCLPFFFAFMMLMNDW

STIWAMSFMASIFLHILLVHDTRVMALQALFSVLVAYLAVYGLTDFHPTT

LIEWQYIPIFLFTYVFGNLCFFRNQISERHGKHDLSFQVAALSHDVKTPL

TVLKGNIELLEMTEVNEQQADFIESMKNSLTVFDKYFNTMISYTKLLNDE

NDYKATISLEDFLIDLSVELEELSTTYQVDYQLVKKTDLTTFYGNTLALS

RALINIFVNACQYAKEGEKIVSLSIYDDEKYLYFEIWNNGHPFSEQAKKN

AGKLEFTEDTGRSGKHYGIGLSFAQGVALKHQGNLILSNPQKGGAEVILK

IKK

Spak (gi|489312641|ref|WP_003220038.1|MULTI-
SPECIES: histidine kinase [Bacillus])
(SEQ ID NO: 14)
MGIGFKGRKTLLRELVKYMVTLCISLVVLALLYIFINTIAMNTGFSHPAN

YNEREAEKLAPKLETIDKVTADMIPDTMSYAILNKETKQKTAGTIKEKDL

QLVKKKIEKKPYVNYKQGYLVIERNNEYCVLQYSLRADFSSPLLRKYLP
NYELTSICILIILLIIVISIITTYFANRLRKHFETLNVITRYIKEQNLQF
TPEFTHIKEFDDVIDSLIEMRDALQSSLEAQWRLEKNKKEQIGALAHDIK
IPITIIKGNAELLSLSMQNEEQAEYTKYILGAGNQIEQYIYQUHLSKTED
ALTIHLEKASVDELTETLVKDISAYKGNKNINISFKKENLMKEAKIDWQL
LHRALLNILTNAVDYTPEGGTVSVHAECDSEIFYFFVKDTGNGESEMGLK
KATELFYMDDKSRHSKGHYGMGLTFAKNAVNLHNGELTLGNTIAGGAEVR
VKIPLRNE

NisK Amino Acids 221-447
(SEQ ID NO: 15)
AERHEKHDLSFQVAALSHDVKTPLTVLKGNIELLEMTEVNEQQADFIESM
KNSLTVFDKYFNTMISYTKLLNDENDYKATISLEDFLIDLSVELEELSTT
YQVDYQLVKKTDLTTFYGNTLALSRALINIFVNACQYAKEGEKIVSLSIY
DDEKYLYFEIWNNGHPFSEQAKKNAGKLFFTEDTGRSGKHYGIGLSFAQG
VALKHQGNLILSNPQKGGAEVILKIKK Hyb1
(SEQ ID NO: 16)
MIVSMDVIKRVYQYAEPNLSLVGWMGMLGFPAYYFIWEYWFPQSYENLGL
RCAAAVLFGGLVFRDSMPKKWQRYMPGYFLFTIGFCLPFFFAFMMLMNDW
STIWAMSFMASIFLHILLVHDTRVMALQALFSVLVAYLAVYGLTDFHPTT
LIEWQYIPIFLFTYVFGNLCFFRRFLIEAERHEKHDLSFQVAALSHDVKTP
LTVLKGNIELLEMTEVNEQQADFIESMKNSLTVFDKYFNTMISYTKLLND
ENDYKATISLEDFLIDLSVELEELSTTYQVDYQLVKKTDLTTFYGNTLAL
SRALINIFVNACQYAKEGEKIVSLSIYDDEKYLYFEIWNNGHPFSEQAKK
NAGKLFFTEDTGRSGKHYGIGLSFAQGVALKHQGNLILSNPQKGGAEVIL
KIKK Hyb2
(SEQ ID NO: 17)
MIVSMDVIKRVYQYAEPNLSLVGWMGMLGFPAYYFIWEYWFPQSYENLGL
RCAAAVLFGGLVFRDSMPKKWQRYMPGYFLFTIGFCLPFFFAFMMLMNDW
STIWAMSFMASIFLHILLVHDTRVMALQALFSVLVAYLAVYGLTDFHPTT
LIEWQYIPIFLFTYVFGNLCFFRNLIEAERHEKHDLSFQVAALSHDVKTP
LTVLKGNIELLEMTEVNEQQADFIESMKNSLTVFDKYFNTMISYTKLLND
ENDYKATISLEDFLIDLSVELEELSTTYQVDYQLVKKTDLTTFYGNTLAL
SRALINIFVNACQYAKEGEKIVSLSIYDDEKYLYFEIWNNGHPFSEQAKK
NAGKLFFTEDTGRSGKHYGIGLSFAQGVALKHQGNLILSNPQKGGAEVIL
KIKK Hyb3
(SEQ ID NO: 18)
MIVSMDVIKRVYQYAEPNLSLVGWMGMLGFPAYYFIWEYWFPQSYENLGL
RCAAAVLFGGLVFRDSMPKKWQRYMPGYFLFTIGFCLPFFFAFMMLMNDW
STIWAMSFMASIFLHILLVHDTRVMALQALFSVLVAYLAVYGLTDFHPTT
LIEWQYIPIFLFTYVFGNLCFFRNQIEAERHEKHDLSFQVAALSHDVKTP
LTVLKGNIELLEMTEVNEQQADFIESMKNSLTVFDKYFNTMISYTKLLND
ENDYKATISLEDFLIDLSVELEELSTTYQVDYQLVKKTDLTTFYGNTLAL
SRALINIFVNACQYAKEGEKIVSLSIYDDEKYLYFEIWNNGHPFSEQAKK
NAGKLFFTEDTGRSGKHYGIGLSFAQGVALKHQGNLILSNPQKGGAEVIL
KIKK Hyb4
(SEQ ID NO: 19)
MIVSMDVIKRVYQYAEPNLSLVGWMGMLGFPAYYFIWEYWFPQSYENLGL
RCAAAVLFGGLVFRDSMPKKWQRYMPGYFLFTIGFCLPFFFAFMMLMNDW
STIWAMSFMASIFLHILLVHDTRVMALQALFSVLVAYLAVYGLTDFHPTT
LIEWQYIPIFLFTYVFGNLCFFRNQISAERHEKHDLSFQVAALSHDVKTP
LTVLKGNIELLEMTEVNEQQADFIESMKNSLTVFDKYFNTMISYTKLLND
ENDYKATISLEDFLIDLSVELEELSTTYQVDYQLVKKTDLTTFYGNTLAL
SRALINIFVNACQYAKEGEKIVSLSIYDDEKYLYFEIWNNGHPFSEQAKK
NAGKLFFTEDTGRSGKHYGIGLSFAQGVALKHQGNLILSNPQKGGAEVIL
KIKK Hyb5
(SEQ ID NO: 20)
MIVSMDVIKRVYQYAEPNLSLVGWMGMLGFPAYYFIWEYWFPQSYENLGL
RCAAAVLFGGLVFRDSMPKKWQRYMPGYFLFTIGFCLPFFFAFMMLMNDW
STIWAMSFMASIFLHILLVHDTRVMALQALFSVLVAYLAVYGLTDFHPTT
LIEWQYIPIFLFTYVFGNLCFFRNQIREFSKNFQAVQKIALKMGEITTFP
EQEESKIIEFDQVLNNLYSKSKELAFLIEAERHEKHDLSFQVAALSHDVK
TPLTVLKGNIELLEMTEVNEQQADFIESMKNSLTVFDKYFNTMISYTKLL
NDENDYKATISLEDFLIDLSVELEELSTTYQVDYQLVKKTDLTTFYGNTL
ALSRALINIFVNACQYAKEGEKIVSLSIYDDEKYLYFEIWNNGHPFSEQA
KKNAGKLFFTEDTGRSGKHYGIGLSFAQGVALKHQGNLILSNPQKGGAEV
ILKIKK Hyb6
(SEQ ID NO: 21)
MIVSMDVIKRVYQYAEPNLSLVGWMGMLGFPAYYFIWEYWFPQSYENLGL
RCAAAVLFGGLVFRDSMPKKWQRYMPGYFLFTIGFCLPFFFAFMMLMNDW
STIWAMSFMASIFLHILLVHDTRVMALQALFSVLVAYLAVYGLTDFHPTT
LIEWQYIPIFLFTYVFGNLCFFRNQIREFSKNFQAVQKIALKMGEITTFP
EQEESKIIEFDQVLNNLYSKSKELAFLIEAERHEKHDLSFQVAALSHDVK
TPLTVLKGNIELLEMTEVNEQQADFIESMKNSLTVFDKYFNTMISYTKLL
NDENDYKATISLEDFLIDLSVELEELSTTYQVDYQLVKKTDLTTFYGNTL
ALSRALINIFVNACQYAKEGEKIVSLSIYDDEKYLYFEIWNNGHPFSEQA
KKNAGKLFFTEDTGRSGKHYGIGLSFAQGVALKHQGNLILSNPQKGGAEV
ILKIKK Hyb7
(SEQ ID NO: 22)
MIVSMDVIKRVYQYAEPNLSLVGWMGMLGFPAYYFIWEYWFPQSYENLGL
RCAAAVLFGGLVFRDSMPKKWQRYMPGYFLFTIGFCLPFFFAFMMLMNDW
STIWAMSFMASIFLHILLVHDTRVMALQALFSVLVAYLAVYGLTDFHPTT
LIEWQYIPIFLFTYVFGNLCFFRNLIREFSKNFQAVQKIALKMGEITTFP EQEESKIIEFDQVLNNLYSKSKELAFLIEAERHEKHDLSFQVAALSHDVK
TPLTVLKGNIELLEMTEVNEQQADFIESMKNSLTVFDKYFNTMISYTKLL
NDENDYKATISLEDFLIDLSVELEELSTTYQVDYQLVKKTDLTTFYGNTL
ALSRALINIFVNACQYAKEGEKIVSLSIYDDEKYLYFEIWNNGHPFSEQA
KKNAGKLFFTEDTGRSGKHYGIGLSFAQGVALKHQGNLILSNPQKGGAEV
ILKIKK Hyb8
(SEQ ID NO: 23)
MIVSMDVIKRVYQYAEPNLSLVGWMGMLGFPAYYFIWEYWFPQSYENLGL
RCAAAVLFGGLVFRDSMPKKWQRYMPGYFLFTIGFCLPFFFAFMMLMNDW
STIWAMSFMASIFLHILLVHDTRVMALQALFSVLVAYLAVYGLTDFHPTT
LIEWQYIPIFLFTYVFGNLCFFRNQLIREFSKNFQAVQKIALKMGEITTF
PEQEESKIIEFDQVLNNLYSKSKELAFLIEAERHEKHDLSFQVAALSHDV
KTPLTVLKGNIELLEMTEVNEQQADFIESMKNSLTVFDKYFNTMISYTKL
LNDENDYKATISLEDFLIDLSVELEELSTTYQVDYQLVKKTDLTTFYGNT
LALSRALINIFVNACQYAKEGEKIVSLSIYDDEKYLYFEIWNNGHPFSEQ
AKKNAGKLFFTEDTGRSGKHYGIGLSFAQGVALKHQGNLILSNPQKGGAE
VILKIKK Hyb9
(SEQ ID NO: 24)
MIVSMDVIKRVYQYAEPNLSLVGWMGMLGFPAYYFIWEYWFPQSYENLGL
RCAAAVLFGGLVFRDSMPKKWQRYMPGYFLFTIGFCLPFFFAFMMLMNDW
STIWAMSFMASIFLHILLVHDTRVMALQALFSVLVAYLAVYGLTDFHPTT
LIEWQYIPIFLFTYVFGNLCFFHLIREFSKNFQAVQKIALKMGEITTFPE
QEESKIIEFDQVLNNLYSKSKELAFLIEAERHEKHDLSFQVAALSHDVKT
PLTVLKGNIELLEMTEVNEQQADFIESMKNSLTVFDKYFNTMISYTKLLN
DENDYKATISLEDFLIDLSVELEELSTTYQVDYQLVKKTDLTTFYGNTLA
LSRALINIFVNACQYAKEGEKIVSLSIYDDEKYLYFEIWNNGHPFSEQAK
KNAGKLFFTEDTGRSGKHYGIGLSFAQGVALKHQGNLILSNPQKGGAEVI
LKIKK Hyb10
(SEQ ID NO: 25)
MIVSMDVIKRVYQYAEPNLSLVGWMGMLGFPAYYFINVEYWFPQSYENLG
LRCAAAVLFGGLVFRDSMPKKWQRYMPGYFLFTIGFCLPFFFAFMMLMND
WSTIWAMSFMASIFLHILLVHDTRVMALQALFSVLVAYLAVYGLTDFHPT
TLIEWQYIPIFLFTYVFGNLCFFRNQISHLIREFSKNFQAVQKIALKMGE
ITTFPEQEESKIIEFDQVLNNLYSKSKELAFLIEAERHEKHDLSFQVAAL
SHDVKTPLTVLKGNIELLEMTEVNEQQADFIESMKNSLTVEDKYENTMIS
YTKLLNDENDYKATISLEDFLIDLSVELEELSTTYQVDYQLVKKTDLTTF
YGNTLALSRALINIFVNACQYAKEGEKIVSLSIYDDEKYLYFEIWNNGHP
FSEQAKKNAGKLFFTEDTGRSGKHYGIGLSFAQGVALKHQGNLILSNPQK
GGAEVILKIKK mCherry Amino Acid Sequence
(SEQ ID NO: 26)
MVSKGEEDNMAIIKEFMRFKVHMEGSVNGHEFEIEGEGEGRPYEGTQTAK
LKVTKGGPLPFAWDILSPQFMYGSKAYVKHPADIPDYLKLSFPEGFKWER
VMNFEDGGVVTVTQDSSLQDGEFIYKVKLRGTNFPSDGPVMQKKTMGWEA
SSERMYPEDGALKGEIKQRLKLKDGGHYDAEVKTTYKAKKPVQLPGAYNV
NIKLDITSHNEDYTIVEQYERAEGRHSTGGMETDELYK nisA promoter
(SEQ ID NO: 27)
AGTCTTATAACTATACTGACAATAGAAACATTAACAAATCTAAAACAGTC
TTAATTCTATCTTGAGAAAGTATTGGTAATAATATTATTGTCGATAACGC
GAGCATAATAAACGGCTCTGATTAAATTCTGAAGTTTGTTAGATACAATG
ATTTCGTTCGAAGGAACTACAAAATA nisR promoter
(SEQ ID NO: 28)
CCGGCTTTAGGTATAGTGTGTATCTCAATCCTTGGTATATTGAAAAGAAA
GACTAAAAATTGATAGATTATATTTCTTCAGAATGAATGGTATAATGAAG
TAATGAGTACTAAACAATCG xyltet2 promoter
(SEQ ID NO: 29)
AAAACTAAAAAAAATATTGACACTCTATCATTGATAGAGTATAATTAAAA
TAAGCTCCCTATCAGTGATAGAGAGAGAAAACGTATAAATTAGGGATAAA
CTATGGAACTTATGAAATAGATTGAAATGGTTTATCTGTTACCCCGTATC
AAAATTT β-lactamase Amino Acid Sequence
(SEQ ID NO: 30)
MSIQHFRVALIPFFAAFCLPVFAHPETLVKVKDAEDQLGARVGYIELDLN
SGKILESFRPEERFPMMSTFKVLLCGAVLSRVDAGQEQLGRRIHYSQNDL
VEYSPVTEKHLTDGMTVRELCSAAITMSDNTAANLLLTTIGGPKELTAFL
HNMGDHVTRLDRWEPELNEAIPNDERDTTMPAAMATTLRKLLTGELLTLA
SRQQLIDWMEADKVAGPLLRSALPAGWFIADKSGAGERGSRGIIAALGPD
GKPSRIVVIYTTGSQATMDERNRQIAEIGASLIKHW β-lactamase Nucleic Acid Sequence
(SEQ ID NO: 31)
ATGAGCATTCAACATTTTAGAGTTGCCTTAATTCCTTTCTTCGCGGCTTT
TTGCTTGCCGGTTTTCGCTCATCCAGAAACTTTGGTAAAGGTTAAAGACG
CAGAAGACCAGTTGGGTGCACGAGTCGGGTATATTGAATTGGATCTTAAC
AGTGGCAAGATATTGGAGAGTTTCAGACCGGAAGAGCGATTCCCGATGAT
GTCTACCTTCAAGGTCCTTTTGTGTGGAGCTGTTTTGAGCCGAGTTGACG
CGGGTCAAGAACAGCTTGGAAGACGAATACATTACTCACAAAACGATTTA
GTCGAGTACAGCCCAGTGACAGAAAAACATCTTACCGATGGTATGACGGT
CCGAGAATTGTGTAGCGCGGCAATAACCATGAGTGACAATACGGCTGCCA
ATCTTCTTTTGACGACCATCGGAGGACCTAAAGAACTTACCGCATTTTTA
CATAATATGGGGGACCATGTTACTAGATTGGATCGTTGGGAACCTGAGCT
TAACGAAGCTATTCCAAACGACGAAAGAGATACCACAATGCCGGCGGCCA
TGGCGACCACTTTACGTAAGCTTTTAACTGGTGAACTTTTGACTTTGGCC
AGCCGACAGCAGCTTATTGATTGGATGGAAGCGGACAAAGTAGCAGGGCC
GTTATTACGATCTGCGTTACCGGCAGGATGGTTTATAGCCGACAAAAGCG -continued

```
GTGCTGGTGAACGAGGCAGCAGAGGTATAATTGCGGCTTTAGGACCGGAC

GGCAAACCAAGTAGAATCGTAGTCATATACACCACGGGGAGTCAGGCCAC

CATGGATGAACGTAATCGTCAAATCGCGGAAATTGGAGCTTCATTGATAA

AGCACTGG
```

REFERENCES

1. Cholera. World Health Organization. http://www.who.int/mediacentre/factsheets/fs107/en/Retrieved Oct. 19, 2014.
2. Higgins, D. A., et al., *The major Vibrio cholerae autoinducer and its role in virulence factor production*. Nature, 2007. 450(7171): p. 883-6.
3. Mierau, I. and M. Kleerebezern, 10 *years of the nisin-controlled gene expression system (NICE) in Lactococcus lactis*. Appl Microbiol Biotechnol, 2005. 68(6): p. 705-17.
4. Geissendörfer, M., and W. Hillen. 1990. Regulated expression of heterologous genes in *Bacillus subtilis* using the Tn10 encoded tet regulatory elements. Appl. Microbiol. Biotechnol. 33:657-663.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An engineered microorganism comprising
   a hybrid receptor comprising at least the binding portion of a CqsS polypeptide and a heterologous histidine kinase domain of a two-component system; and
   a genetic circuit responsive to the heterologous histidine kinase.

2. The engineered microorganism of claim 1, wherein the heterologous histidine kinase domain is from NisK or SpaK.

3. The engineered microorganism of claim 2, wherein the heterologous histidine kinase domain comprises a glutamic acid to glycine mutation at position 225 relative to full length NisK (SEQ ID NO: 5).

4. The engineered microorganism of claim 1, wherein the hybrid receptor comprises
   (i) amino acids 221-447 of NisK (SEQ ID NO: 15),
   (ii) amino acids 221-447 of NisK having an E225G mutation (SEQ ID NO: 3),
   (iii) the amino acid sequence of SEQ ID NO: 2, or
   (iv) the amino acid sequence of SEQ ID NO: 1.

5. The engineered microorganism of claim 1, wherein the genetic circuit comprises a first promoter that is operably linked to a nucleic acid sequence encoding the hybrid receptor and a second promoter that is responsive to the heterologous histidine kinase domain and is operably linked to a nucleic acid sequence encoding an output molecule.

6. The engineered microorganism of claim 5, wherein the first promoter is inducible or constitutive, optionally wherein the first promoter is a nisR promoter.

7. The engineered microorganism of claim 1, wherein the genetic circuit comprises a first promoter that is operably linked to a nucleic acid sequence encoding the hybrid receptor, a second promoter that is operably linked to a nucleic acid sequence encoding a repressor molecule, and a third promoter that is operably linked to a nucleic acid sequence encoding an output molecule;
   wherein the second promoter is responsive to the heterologous histidine kinase domain, and
   wherein the third promoter is responsive to the repressor molecule, and wherein the repressor molecule binds to the third promoter and represses transcription of the output molecule.

8. The engineered microorganism of claim 7, wherein the first promoter is inducible or constitutive.

9. The engineered microorganism of claim 7, wherein the first promoter is a nisR promoter, the second promoter is a nisA promoter, and/or wherein the third promoter is a xyltet2 promoter.

10. The engineered microorganism of claim 5, wherein the output molecule is an antimicrobial peptide, a, lysing polypeptide, a reporter polypeptide, a peptide that acts on a substrate, or a nucleic acid, optionally wherein the output molecule is mCherry, or β-lactamase.

11. A method of detecting and/or treating a cholera infection, comprising administering to a subject having or at risk of having a cholera infection the engineered microorganism of claim 1.

12. The method of claim 11, further comprising administering to the subject an antibiotic agent effective for killing *Vibrio cholerae* when the engineered microorganism expresses a detectable output molecule.

13. A method of detecting a cholera infection, comprising
   (i) obtaining a biological sample from a subject having or at risk of having a cholera infection, and
   (ii) contacting the biological sample with the engineered microorganism of claim 1, thereby creating a reaction mixture.

14. The method of claim 13, wherein the biological sample is a fecal sample.

15. The method of claim 13, further comprising (iii) contacting the reaction mixture of (ii) with a substrate, and/or wherein the substrate is a colorimetric substrate, optionally, wherein the substrate is nitrocefin.

16. The method of claim 15, further comprising (iv), detecting a color change of the reaction mixture of (iii), optionally wherein the detecting comprises spectrophotometry.

17. A method of detecting and treating a cholera infection in a subject, comprising
   (a) obtaining a biological sample from a subject having or at risk of having a cholera infection, and
   (b) contacting the biological sample with the engineered microorganism of claim 1, thereby creating a reaction mixture,
   (c) determining if the subject has a cholera infection based on (a) and (b), and
   (d) administering to the subject the engineered microorganism if it is determined in (c) that the subject has a cholera infection.

18. A hybrid receptor comprising
at least the binding portion of a CqsS polypeptide and a heterologous histidine kinase domain of a two-component system.

19. The hybrid receptor of claim 18 wherein the heterologous histidine kinase domain is from NisK or SpaK, and/or wherein the histidine kinase domain comprises a glutamic acid to glycine mutation at position 225 relative to full length NisK (SEQ ID NO: 5).

20. The hybrid receptor of claim 18, wherein the hybrid receptor comprises
   (i) amino acids 221-447 of NisK (SEQ ID NO: 15),
   (ii) amino acids 221-447 of NisK having an E225G mutation (SEQ ID NO: 3),
   (iii) the amino acid sequence of SEQ ID NO: 2,
   (iv) the amino acid sequence of SEQ ID NO: 1,
   (v) an amino acid sequence selected from the group consisting of SEQ ID NOs: 6-13, or
   (vi) an amino acid sequence selected from the group consisting of SEQ ID NOs: 16-25.

* * * * *